US008019199B2

(12) United States Patent
Hamada et al.

(10) Patent No.: US 8,019,199 B2
(45) Date of Patent: Sep. 13, 2011

(54) REPRODUCTION DEVICE, REPRODUCTION METHOD, REPRODUCTION PROGRAM, RECORDING MEDIUM, AND DATA STRUCTURE

(75) Inventors: Toshiya Hamada, Saitama (JP); Tatsuya Kakumu, Tokyo (JP); Yasushi Fujinami, Tokyo (JP)

(73) Assignees: Sony Corporation, Tokyo (JP); Sony Computer Entertainment Inc., Tokyo (JP)

(*) Notice: Subject to any disclaimer, the term of this patent is extended or adjusted under 35 U.S.C. 154(b) by 1201 days.

(21) Appl. No.: 11/573,696

(22) PCT Filed: Aug. 2, 2005

(86) PCT No.: PCT/JP2005/014491
§ 371 (c)(1), (2), (4) Date: Feb. 14, 2007

(87) PCT Pub. No.: WO2006/019000
PCT Pub. Date: Feb. 23, 2006

(65) Prior Publication Data
US 2008/0063373 A1    Mar. 13, 2008

(30) Foreign Application Priority Data
Aug. 19, 2004    (JP) .................................. 2004-239347

(51) Int. Cl.
*H04N 9/80*    (2006.01)
(52) U.S. Cl. ........................................ 386/262; 386/248
(58) Field of Classification Search .......... 386/1, 45–46, 386/125–126, 148, 162
See application file for complete search history.

(56) References Cited

U.S. PATENT DOCUMENTS

| | | | | |
|---|---|---|---|---|
| 6,393,201 B1 * | 5/2002 | Sakuramoto et al. | ......... | 386/240 |
| 6,424,794 B1 * | 7/2002 | Cookson et al. | .............. | 386/201 |
| 6,442,333 B1 * | 8/2002 | Izawa | ........................... | 386/240 |
| 6,542,200 B1 * | 4/2003 | Barcy et al. | ................... | 348/468 |
| 2006/0210245 A1 * | 9/2006 | McCrossan et al. | ............ | 386/95 |

FOREIGN PATENT DOCUMENTS

| | | |
|---|---|---|
| JP | 9-50675 | 2/1997 |
| JP | 2004-23646 | 1/2004 |
| JP | 2004-112207 | 4/2004 |
| JP | 2004-207904 | 7/2004 |

* cited by examiner

*Primary Examiner* — Thai Tran
*Assistant Examiner* — Nigar Chowdhury
(74) *Attorney, Agent, or Firm* — Oblon, Spivak, McClelland, Maier & Neustadt, L.L.P.

(57) ABSTRACT

When content is reproduced from a disc, audio and a subtitle can be properly and automatically selected. An original language can be set as a language of an audio stream to be reproduced on a player side. An audio stream of the original language is described at a position that comes first in a clip information file. When audio and a subtitle are automatically set, if their languages match, the subtitle is not displayed. When player setting 500 denotes that audio is an original language and subtitle Japanese and streams 501 contained in a disc are an audio stream of Japanese (original language), an audio stream of English, a subtitle stream of English, and a subtitle stream of Japanese, the audio stream of Japanese as the original language and the subtitle stream of Japanese are selected according to the automatic setting. Since their languages match, although streams 502 finally selected are the audio stream of Japanese and the subtitle stream of Japanese, the subtitle stream of Japanese is not displayed.

14 Claims, 51 Drawing Sheets

*Fig. 4*

| STATE | DESCRIPTION |
|---|---|
| PLAY | REPRESENTS THAT PLAY LIST IS BEING REPRODUCED AND TIME HAS ELAPSED. INCLUDES NORMAL REPRODUCTION, VARIABLE SPEED REPRODUCTION, FAST FORWARD, REWIND. FRAME FORWARD AND FRAME REVERSE ARE STATE OF WHICH PAUSE AND PLAY ARE REPEATED. |
| PAUSE | REPRESENTS THAT PLAY LIST IS BEING REPRODUCED AND TIME AXIS STOPS. |
| STOP | STATE THAT PLAY LIST IS NOT BEING REPRODUCED. |

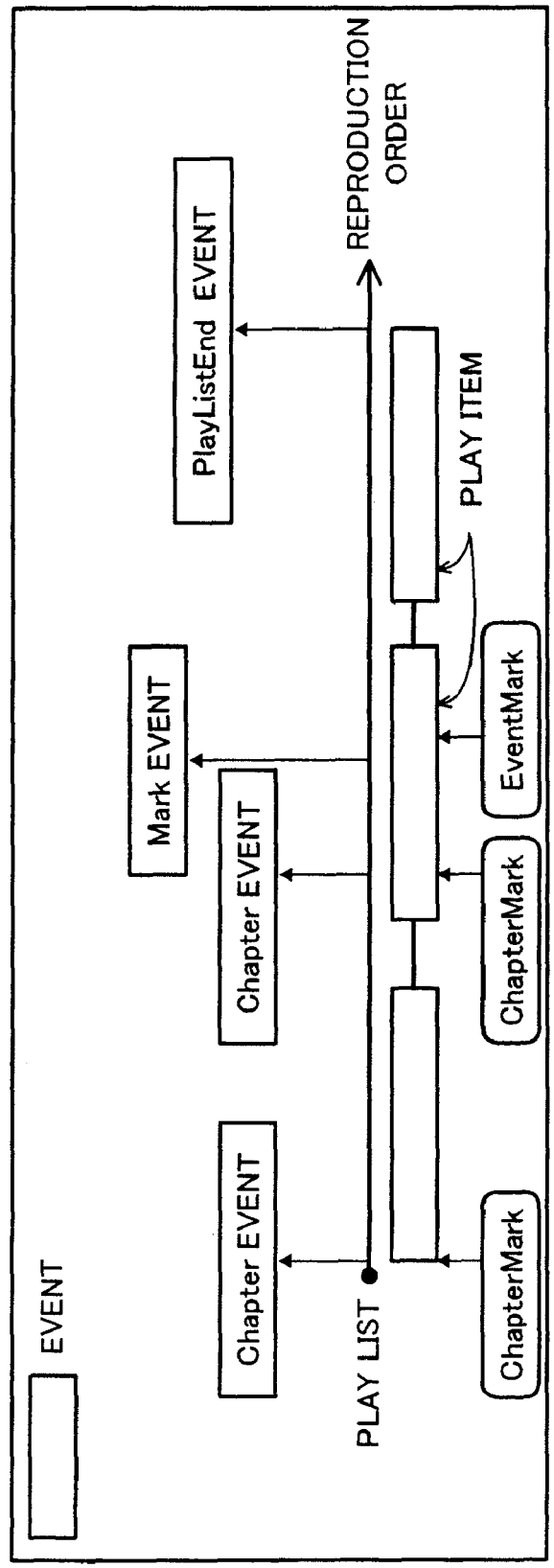

Fig. 7

| NAME | DESCRIPTION |
|---|---|
| scriptVersion | VERSION OF UMD VIDEO SCRIPT |
| languageCode | MENU DISPLAY LANGUAGE CODE THAT IS SET TO UMD VIDEO PLAYER |
| audioLanguageCode | AUDIO LANGUAGE CODE THAT IS SET TO UMD VIDEO PLAYER |
| subtitleLanguageCode | SUBTITLE LANGUAGE CODE THAT IS SET TO UMD VIDEO PLAYER |
| playListNumber | PLAY LIST NUMBER OF PLAY LIST BEING CURRENTLY REPRODUCED |
| chapterNumber | CHAPTER NUMBER OF CHAPTER BEING CURRENTLY REPRODUCED |
| videoNumber | VIDEO STREAM NUMBER OF VIDEO STREAM BEING CURRENTLY REPRODUCED |
| audioNumber | AUDIO STREAM NUMBER OF AUDIO STREAM BEING CURRENTLY REPRODUCED |
| subtitleNumber | SUBTITLE STREAM NUMBER OF SUBTITLE STREAM BEING CURRENTLY REPRODUCED |
| playListTime | TIME OF PLAY LIST WHEN BEGINNING IS 0 |
| audioFlag | DESIGNATION OF ON/OFF OF AUDIO REPRODUCTION AND DUAL MONO LR |
| subtitleFlag | SUBTITLE DISPLAY ON/OFF |

READ-ONLY PARAMETERS: scriptVersion, languageCode, audioLanguageCode, subtitleLanguageCode PLAYER STATUSES: playListNumber, chapterNumber, videoNumber, audioNumber, subtitleNumber, playListTime, audioFlag, subtitleFlag

Fig. 8

| NAME | DESCRIPTION |
|---|---|
| play() | REPRODUCE VIDEO DATA |
| playChapter() | DESIGNATE CHAPTER AND REPRODUCE VIDEO DATA OF DESIGNATED CHAPTER |
| stop() | STOP REPRODUCING VIDEO DATA |
| pause() | PAUSE REPRODUCTION OF VIDEO DATA |
| playStep() | REPRODUCE VIDEO DATA STEP BY STEP |
| changeStream() | CHANGE VIDEO STREAM, AUDIO STREAM, AND/OR SUBTITLE STREAM |
| getPlayerStatus() | OBTAIN STATE OF PLAY, STOP, PAUSE, OR THE LIKE OF MOVIE PLAYER |
| reset() | STOP REPRODUCING VIDEO DATA AND CLEAR RESUME INFORMATION |
| setPos() | SET DISPLAY POSITION OF VIDEO DATA |
| getPos() | OBTAIN DISPLAY POSITION OF VIDEO DATA |
| setSize() | SET DISPLAY SIZE OF VIDEO DATA |
| getSize() | OBTAIN DISPLAY SIZE OF VIDEO DATA |

Fig. 9

| KEY NAME | DESCRIPTION |
|---|---|
| VK_POWER | POWER KEY |
| VK_POWER_ON | POWER ON KEY |
| VK_POWER_OFF | POWER OFF KEY |
| VK_MENU | NEMU |
| VK_ENTER | ENTER |
| VK_RETURN | RETURN |
| VK_PLAY | PLAY |
| VK_STOP | STOP |
| VK_PAUSE | PAUSE |
| VK_FAST_FORWARD | FAST FORWARD |
| VK_FAST_REVERSE | FAST REVERSE |
| VK_SLOW_FORWARD | SLOW (FORWARD) |
| VK_SLOW_REVERSE | SLOW (REVERSE) |
| VK_STEP_FORWARD | STEP REPRODUCTION (FORWARD) |
| VK_STEP_REVERSE | STEP REPRODUCTION (REVERSE) |

Fig. 10

| KEY NAME | DESCRIPTION |
|---|---|
| VK_NEXT | NEXT |
| VK_PREVIOUS | PREVIOUS |
| VK_UP | UP |
| VK_DOWN | DOWN |
| VK_RIGHT | RIGHT |
| VK_LEFT | LEFT |
| VK_UP_RIGHT | UP RIGHT |
| VK_UP_LEFT | UP LEFT |
| VK_DOWN_RIGHT | DOWN RIGHT |
| VK_DOWN_LEFT | DOWN LEFT |
| VK_ANGLE | CHANGE ANGLE |
| VK_SUBTITLE | CHANGE SUBTITLE |
| VK_AUDIO | CHANGE AUDIO |
| VK_VIDEO_ASPECT | CHANGE ASPECT RATIO OF VIDEO |
| VK_COLORED_KEY_1 | COLORED FUNCTION KEY 1 |
| VK_COLORED_KEY_2 | COLORED FUNCTION KEY 2 |
| VK_COLORED_KEY_3 | COLORED FUNCTION KEY 3 |
| VK_COLORED_KEY_4 | COLORED FUNCTION KEY 4 |
| VK_COLORED_KEY_5 | COLORED FUNCTION KEY 5 |
| VK_COLORED_KEY_6 | COLORED FUNCTION KEY 6 |

Fig.11A

| CONTROL COMMAND ACCORDING TO USER'S OPERATION | DESCRIPTION |
|---|---|
| uo_timeSearch(playListTime) | REPRODUCE PLAY LIST BEING REPRODUCED FROM DESIGNATED TIME. playListTime REPRESENTS TIME OF PLAY LIST WHEN BEGINNING IS 0. THIS COMMAND DOES NOT DESIGNATE PLAY LIST NUMBER. THUS, TIME IS DESIGNATED IN RANGE OF PLAY LIST CURRENTLY BEING REPRODUCED. |
| uo_play() | WITH 1X THIS COMMAND STARTS REPRODUCING PLAY LIST AT REGULAR SPEED. START POSITION IS DECIDED WITH RESUME INFORMATION. WITHOUT RESUME INFORMATION DESIGNATED, USER'S OPERATION IS INVALIDATED. THIS COMMAND CORRESPONDS TO play() METHOD WITHOUT playListNumber DESIGNATED. PLAY LIST NUMBER CANNOT BE DESIGNATED BY USER'S OPERATION. |
| uo_playChapter(chapterNumber) | START REPRODUCING PLAY LIST BEING REPRODUCED FROM DESIGNATED CHAPTER. WITHOUT CHAPTER DESIGNATED, THIS COMMAND STARTS REPRODUCING PLAY LIST FROM BEGINNING OF CHAPTER BEING REPRODUCED. THIS COMMAND CORRESPONDS TO playChapter() METHOD WITHOUT chapterNumber DESIGNATED. |

Fig. 11

| Fig. 11A |
|---|
| Fig. 11B |
| Fig. 11C |

Fig. 11B

| | |
|---|---|
| uo_playPrevChapter() | START REPRODUCING PLAY LIST FROM BEGINNING OF CHAPTER BEING REPRODUCED. |
| uo_playNextChapter() | START REPRODUCING PLAY LIST FROM BEGINNING OF NEXT CHAPTER. |
| uo_stop() | STOP REPRODUCING PLAY LIST. |
| uo_jumpToEnd() | JUMP TO END OF PLAY LIST. THIS COMMAND CORRESPONDS TO USER'S OPERATION THAT CAUSES MOVIE PLAYER TO STOP REPRODUCING PLAY LIST BEING REPRODUCED AND GENERATE playListEnd EVENT. SCRIPT EXECUTES onPlayListEnd EVENT HANDLER. |
| uo_forwardScan(speed) | FORWARD REPRODUCE PLAY LIST AT SPEED DESIGNATED BY speed. speed DEPENDS ON IMPLEMENTATION OF UMD VIDEO PLAYER. |
| uo_backwardScan(speed) | BACKWARD REPRODUCE PLAY LIST AT SPEED DESIGNATED BY speed. speed DEPENDS ON IMPLEMENTATION OF UMD VIDEO PLAYER. |

Fig. 11C

| | |
|---|---|
| uo_playStep(forward) | FORWARD REPRODUCE PLAY LIST STEP BY STEP. |
| uo_playStep(backward) | BACKWARD REPRODUCE PLAY LIST STEP BY STEP. |
| uo_pauseOn() | PAUSE REPRODUCTION OF PLAY LIST ACCORDING TO USER'S OPERATION. |
| uo_pauseOff() | CANCEL PAUSE STATE. |
| uo_changeAudioChannel(value) | CHANGE CHANNEL OF AUDIO AND OR DUALMONO. audioFlag NEEDS TO BE ACCORDINGLY CHANGED. |
| uo_setAudioEnabled(boolean) | TURN ON/OFF AUDIO STREAM. audioFlag NEEDS TO BE ACCORDINGLY CHANGED. |
| uo_setSubtitleEnabled(boolean) | TURN ON/OFF SUBTITLE STREAM. subtitleFlag NEEDS TO BE ACCORDINGLY CHANGED. |
| uo_angleChange() | CHANGE DISPLAY ANGLE. WHEN MOVIE PLAYER IS INFORMED OF USER'S OPERATION, MOVIE PLAYER INFORMS SCRIPT OF angleChange EVENT. |
| uo_audioChange(audioStreamNumber) | CHANGE AUDIO TO BE REPRODUCED. |
| uo_subtitleChange(subtitleStreamNumber) | CHANGE SUBTITLE TO BE REPRODUCED. |

Fig. 12

| EVENT | DESCRIPTION | RELATIONSHIP WITH METHOD OF MOVIE PLAYER |
|---|---|---|
| menu | JUMP TO MENU | EVENT OF WHICH SCRIPT RATHER THAN MOVIE PLAYER IS INFORMED. EXECUTE onMenu EVENT HANDLER. |
| exit | EVENT THAT NATIVE PLATFORM ISSUES WHEN NATIVE PLATFORM COMPLETES UMD VIDEO APPLICATION. | EXECUTE onExit EVENT HANDLER. |
| up,down,left,right focusIn, focusOut, push, cancel | EVENTS THAT OCCUR WHILE BUTTON ON SCREEN IS FOCUSED. | EVENTS OF WHICH SCRIPT RATHER THAN MOVIE PLAYER IS INFORMED. |
| autoPlay, continuePlay | EVENTS THAT CAUSE SCRIPT TO START EXECUTING. | |

Fig. 13

| EVENT NAME | CORRESPONDING EVENT HANDLER NAME | DESCRIPTION |
| --- | --- | --- |
| mark | onMark() | EXECUTED WHEN EVENT MARK IS DETECTED. |
| playListEnd | onPlayListEnd() | EXECUTED WHEN REPRODUCTION OF PLAY LIST IS COMPLETED. |
| chapter | onChapter() | EXECUTED WHEN CHAPTER MARK IS DETECTED. |
| angleChange | onAngleChange() | EXECUTED WHEN ANGLE CHANGE IS DESIGNATED BY USER'S OPERATION. |
| audioChange | onAudioChange() | EXECUTED WHEN AUDIO CHANGE IS DESIGNATED BY USER'S OPERATION. |
| subtitleChange | onSubtitleChange() | EXECUTED WHEN SUBTITLE CHANGE IS DESIGNATED BY USER'S OPERATION. |

Fig. 14

| EVENT NAME | CORRESPONDING EVENT HANDLER NAME | DESCRIPTION |
|---|---|---|
| menu | onMenu() | JUMP TO MENU. |
| exit | onExit() | EVENT THAT NATIVE PLATFORM ISSUES WHEN IT COMPLETES UMD VIDEO APPLICATION. |
| autoPlay, continuePlay | onAutoPlay(), onContinuePlay() | START EXECUTING SCRIPT. |

Fig. 22

```
system.onAutoPlay = function(){
    //Play PlayList # 1 FBI warning.
    movieplayer.play(1);
} movieplayersystem.onPlayListEnd = function(event_info){
    if(event_info.playListNumber == 1){
        // play feature film after FBI warning ends.
        movieplayer.play(2);
    }else{
        // transit to top menu after feature film ends.
        resource.pagetable["top_menu"].open();
    }
]

system.onMenu = function(){
    // transfer to top menu with display menu user
operation.
    resource.pagetable["top_menu"].open();
} movieplayer.onMark = function(event_info){
    //display dialog when event mark encountered.
    if(event_info.mark_data == 1){
        resource.pagetable["dialog_window_1"].open();
    }
    ...
}
```

*Fig. 24*

| SYNTAX | NO. OF BITS | MNEMONIC |
|---|---|---|
| "PLAYLIST.DAT" { | | |
|     name_length | 8 | uimsbf |
|     name_string | 8*255 | bslbf |
|     number_of_PlayLists | 16 | uimsbf |
|     for(i=0; i<number_of_PlayLists; i++){ | | |
|         PlayList(){ // A PlayList() | | |
|             PlayList_data_length | 32 | uimsbf |
|         // ATTRIBUTE INFORMATION | | |
|             reserved_for_word_alignment | 15 | bslbf |
|             capture_enable_flag_PlayList | 1 | bslbf |
|             PlayList_name_length | 8 | uimsbf |
|             PlayList_name_string | 8*255 | bslbf |
|         // | | |
|             number_of_PlayItems | 16 | uimsbf |
|             for (i=0; i<number_of_PlayItems; i++) { | | |
|                 PlayItem() | | |
|             } | | |
|             PlayListMark() | | |
|         } | | |
|     } | | |
| } | | |

*Fig. 25*

| SYNTAX | NO. OF BITS | MNEMONIC |
|---|---|---|
| PlayItem() { | | |
| length | 16 | uimsbf |
| Clip_Information_file_name_length | 16 | uimsbf |
| Clip_Information_file_name | 8*Clip_Information_file_name_length | bslbf |
| IN_time | 32 | uimsbf |
| OUT_time | 32 | uimsbf |
| } | | |

Fig. 26

| SYNTAX | NO. OF BITS | MNEMONIC |
|---|---|---|
| PlayListMark() { | | |
|     length | 32 | uimsbf |
|     number_of_PlayList_marks | 16 | uimsbf |
|     for(i=0; i < number_of_PlayList_marks; i++) { | | |
|         Mark(){ | | |
|             mark_type | 8 | uimsbf |
|             mark_name_length | 8 | uimsbf |
|             ref_to_PlayItem_id | 16 | uimsbf |
|             mark_time_stamp | 32 | uimsbf |
|             entry_ES_stream_id | 8 | uimsbf |
|             entry_ES_private_stream_id | 8 | uimsbf |
|             mark_data | 32 | bslbf |
|             mark_name_string | 8*24 | bslbf |
|         } | | |
|     } | | |
| } | | |

Fig. 27

| mark_type | STREAM CODING |
|---|---|
| 0 | RESERVED |
| 1 | CHAPTER MARK |
| 2 | INDEX MARK |
| 3 | EVENT MARK |
| 4-255 | RESERVED |

*Fig. 29*

| SYNTAX | NO. OF BITS | MNEMONIC |
|---|---|---|
| XXXXX.CLP{ | | |
|     presentation_start_time | 32 | uimsbf |
|     presentation_end_time | 32 | uimsbf |
|     reserved_for_word_alignment | 7 | bslbf |
|     capture_enable_flag_Clip | 1 | bslbf |
|     number_of_streams | 8 | uimsbf |
|     for (i = 0;i < number_of_streams;i++) { | | |
|         StreamInfo(){ | | |
|             length | 16 | uimsbf |
|             stream_id | 8 | uimsbf |
|             private_stream_id | 8 | uimsbf |
|         StaticInfo() | | |
|             reserved_for_word_alignment | 8 | bslbf |
|         number_of_DynamicInfo | 8 | uimsbf |
|         for (j = 0;j < number_of_DynamicInfo;j++) { | | |
|             pts_change_point | 32 | uimsbf |
|             DynamicInfo() | | |
|         } | | |
|         } | | |
|     } | | |
|     EP_map() | | |
| } | | |

Fig. 30

| TYPE OF ELEMENTARY STREAM | stream_id | private_stream_id |
|---|---|---|
| VIDEO | 0xE0-0xEF | (NONE) |
| ATRAC AUDIO | 0xBD | 0x00-0x0F |
| LPCM AUDIO | 0xBD | 0x10-0x1F |
| SUBTITLE | 0xBD | 0x80-0x9F |

Fig. 31

| SYNTAX | NO. OF BITS | MNEMONIC |
|---|---|---|
| StaticInfo() { | | |
|     if (stream == VIDEO ) { | | |
|         reserved_for_word_alignment | 16 | bslbf |
|         picture_size | 4 | uimsbf |
|         frame_rate | 4 | uimsbf |
|         reserved_for_word_alignment | 7 | bslbf |
|         cc_flag | 1 | bslbf |
|     } else if (stream == AUDIO ) { | | |
|         audio_language_code | 16 | bslbf |
|         channel_configuration | 8 | uimsbf |
|         reserved_for_word_alignment | 3 | bslbf |
|         lfe_existence | 1 | bslbf |
|         sampling_frequency | 4 | uimsbf |
|     } else if (stream == SUBTITLE) { | | |
|         subtitle_language_code | 16 | bslbf |
|         subtitle_presentation_type | 4 | uimsbf |
|         reserved_for_word_alignment | 15 | bslbf |
|         configurable_flag | 1 | uimsbf |
|     } | | |
| } | | |

Fig. 32

| SYNTAX | NO. OF BITS | MNEMONIC |
|---|---|---|
| DynamicInfo(i,j) { | | |
|     reserved_for_word_alignment | 8 | bslbf |
|     if (stream == VIDEO){ | | |
|         reserved_for_word_alignment | 4 | bslbf |
|         display_aspect_ratio | 4 | uimsbf |
|     } else if (stream == AUDIO ) { | | |
|         reserved_for_word_alignment | 4 | bslbf |
|         channel_assignment | 4 | uimsbf |
|     } else if ( stream == SUBTITLE) { | | |
|         reserved_for_word_alignment | 8 | bslbf |
|     } | | |
| } | | |

Fig. 33

| SYNTAX | NO. OF BITS | MNEMONIC |
|---|---|---|
| EP_map(){ | | |
|     reserved_for_word_alignment | 8 | bslbf |
|     number_of_stream_id_entries | 8 | uimsbf |
|     for (k=0; k<number_of_stream_id_entries; k++) { | | |
|         stream_id | 8 | bslbf |
|         private_stream_id | 8 | bslbf |
|         number_of_EP_entries | 32 | uimsbf |
|         for (i=0; i<number_of_EP_entries; i++) { | | |
|             PTS_EP_start | 32 | uimsbf |
|             RPN_EP_start | 32 | uimsbf |
|         } | | |
|     } | | |
| } | | |

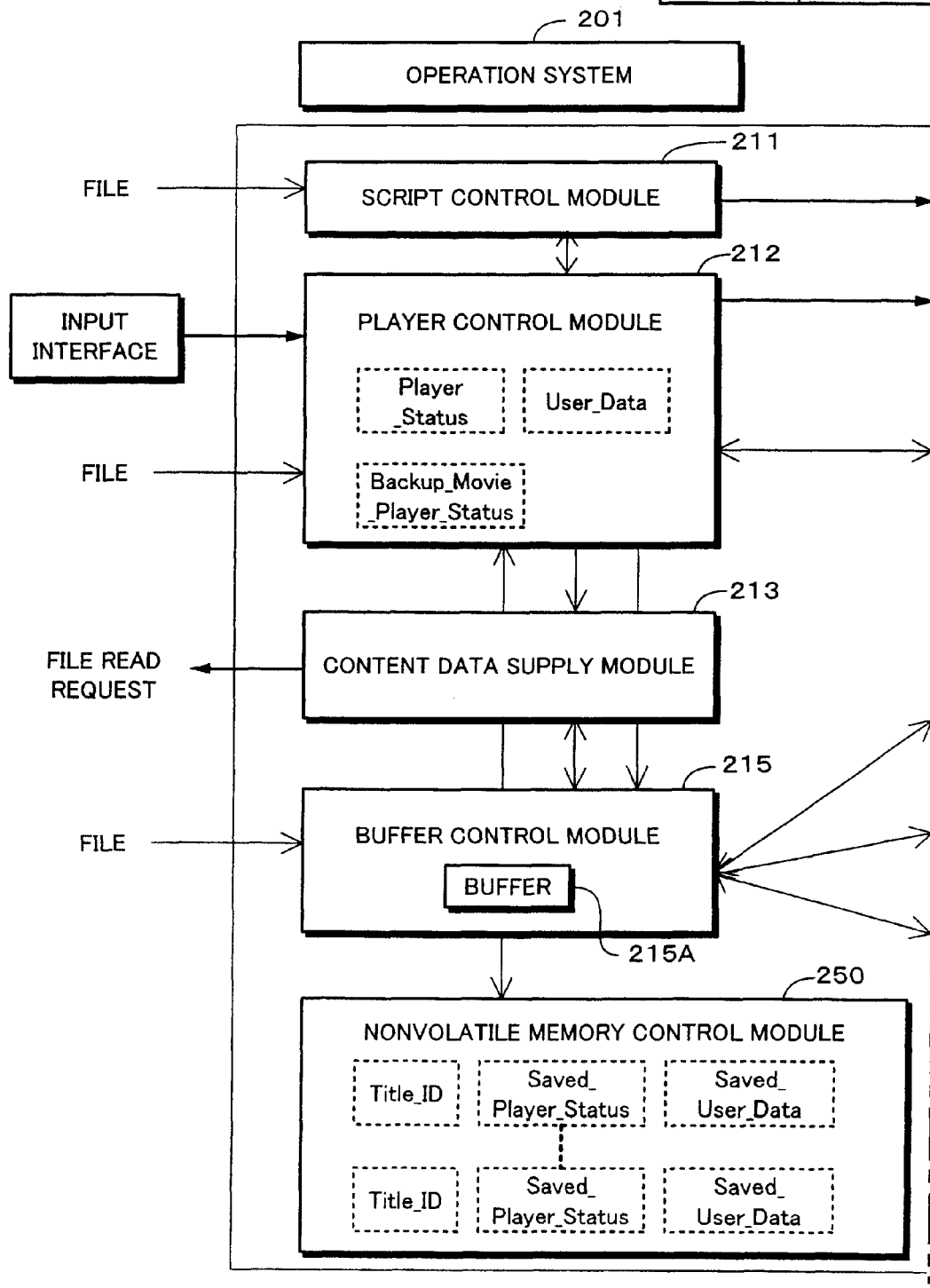

*Fig. 39*

| audioFlag | DESCRIPTION |
|---|---|
| 0 | AUDIO REPRODUCTION OFF |
| 1 | ON<br>REPRODUCTION OF BOTH CHANNELS IN DUAL MONO |
| 2 | ONLY LEFT CHANNEL IN DUAL MONO |
| 3 | ONLY RIGHT CHANNEL IN DUAL MONO |

Fig. 40

| subtitleFlag | DESCRIPTION |
|---|---|
| 0 | SUBTITLE DISPLAY OFF |
| 1 | ON |

| Fig. 41A |
|----------|
| Fig. 41B |

| VALUE | TYPE | DESCRIPTION |
|---|---|---|
| playListNumber | int | REPRESENTS PLAY LIST NUMBER.<br>−1: PLAY LIST NUMBER OF PLAY LIST BEING CURRENTLY REPRODUCED |
| playListTime | int | REPRESENTS TIME FROM BEGINNING OF PLAY LIST.<br>"0" WHEN CONTENT IS REPRODUCED FROM BEGINNING OF PLAY LIST. |
| menuMode | Boolean | TRUE REPRESENTS REPRODUCTION IN MENU MODE.<br>FALSE REPRESENTS REPRODUCTION IN NORMAL SPEED. |
| pauseMode | Boolean | TRUE REPRESENTS STANDBY AS PAUSE.<br>FALSE REPRESENTS START OF REPRODUCTION. |
| video_strm | int | REPRESENTS VIDEO STREAM TO BE REPRODUCED.<br>−1: AUTOMATIC SELECTION BY MOVIE PLAYER.<br>−2: NO CHANGE |
| audio_strm | int | REPRESENTS AUDIO STREAM NUMBER OF AUDIO STREAM TO BE REPRODUCED.<br>−1: AUTOMATIC SELECTION BY MOVIE PLAYER.<br>−2: NO CHANGE |

Fig. 41B

| | | |
|---|---|---|
| audio_status | int | REPRESENTS STATUS OF AUDIO REPRODUCTION.<br><br>VALUE REFLECTS PROPERTY AudioFlag.<br><br>0: AUDIO REPRODUCTION OFF<br><br>1: ON (REPRODUCTION OF BOTH CHANNELS IN DUAL MONO)<br><br>2: REPRODUCTION OF ONLY LEFT IN DUAL MONO<br><br>3: REPRODUCTION OF ONLY RIGHT IN DUAL MONO<br><br>-2: NO CHANGE |
| subtitle_strm | int | REPRESENTS SUBTITLE STREAM NUMBER OF SUBTITLE STREAM TO BE REPRODUCED.<br><br>-1: REPRESENTS AUTOMATIC SELECTION BY MOVIE PLAYER.<br><br>-2: NO CHANGE |
| subtitle_status | int | REPRESENTS STATUS OF REPRODUCTION OF SUBTITLE STREAM.<br><br>VALUE REFLECTS PROPERTY SubtitleFlag.<br><br>0: SUBTITLE DISPLAY OFF<br><br>1: SUBTITLE DISPLAY ON<br><br>-1: AUTOMATIC SELECTION<br><br>-2: NO CHANGE |

US 8,019,199 B2

REPRODUCTION DEVICE, REPRODUCTION METHOD, REPRODUCTION PROGRAM, RECORDING MEDIUM, AND DATA STRUCTURE

TECHNICAL FIELD

The present invention relates to a reproducing apparatus, a reproducing method, a reproducing program, a recording medium, and a data structure that allow an audio stream and a subtitle stream to be properly and automatically selected when a program is reproduced from a large capacity recording medium.

BACKGROUND ART

As a random-accessible, attachable-detachable recording medium, a digital versatile disc (DVD) has been used for years. In recent years, a disc-shaped recording medium that has a larger record capacity than the DVD and another disc-shaped recording medium that is smaller than the DVD have been developed.

Such recording mediums that contain content of video and audio such as movies, drams, music concerts have been sold as sell packages. In these cell packages, a plurality of audio and subtitle streams of different languages can be recorded as one program of content. For example, in the DVD video standard, a video stream, a plurality of audio streams of different languages, and a plurality of subtitle streams of different languages are multiplexed as one Moving Pictures Experts Group2 (MPEG) program stream.

Movie content created in a foreign country (for example, United States) may contain a plurality of audio streams of different languages, which are for example an audio stream of English as an original language and an audio stream of Japanese as a Japanese dubbed audio stream, and a plurality of subtitle streams, which are a subtitle stream of English and a subtitle stream of Japanese.

In the DVD video standard, when movie content contains a plurality of audio streams of different languages and a plurality of subtitle streams of different languages, the user can select streams to be reproduced. For example, the user may be able to select an audio stream of a Japanese dubbed version and a subtitle stream of an English version. As another example, the user may able to select an audio stream of a Japanese dubbed version and select no subtitle stream.

A DVD player apparatus has an automatic selection function that allows a priority language to be initially set as language preset information and an audio stream and a subtitle stream to be automatically selected based on the language preset information without need to user's selections. In addition, the DVD player is provided with a function that selects the next stream to be reproduced depending on the reproduction history and reproduction path of content besides the initial setting.

Next, the existing audio stream selection function based on the DVD video standard will be described in brief. As described above, with the DVD player apparatus, audio that is selected and reproduced by priority can be initially set. When the DVD player apparatus is used for example by a Japanese user, audio may be often initially set to "Japanese". In this setting, when the DVD player apparatus reproduces for example an American movie or a French movie, as long as an audio stream of Japanese has been recorded, an audio stream of the Japanese dubbed version is automatically selected by priority.

In contrast, some users may want to listen to audio of the original language in which content was created. For example, it seems that users may want to watch movie content with audio of the original language in which the content was created and a subtitle of a translated version of user's mother language. For example, when the user who is Japanese watches movie content created in the United States, the movie content may be reproduced with audio of English as the original language in which the content was created and a subtitle of Japanese, which is a user's mother language. When the user watches content by selecting audio and language in such a manner, he or she can enjoy the content in an atmosphere close to the original.

Japanese Patent Application Laid-Open No. 2003-46951 discloses a reproducing apparatus having a mode of which a language of audio to be reproduced is selected and no subtitle is displayed, a mode of which a language of audio to be reproduced is set by default and a language of a subtitle is selected, and a mode of which languages of audio, a subtitle, and a menu are selected so that languages can be easily set.

However, the exiting DVD video standard does have a mechanism that denotes whether or not the language of a recorded audio stream is the original language in which content was created. Thus, the original language is not able to be automatically selected when content of a disc is reproduced. Consequently, whenever content is reproduced from a disc, as a problem of the related art, the user needs to change the setting of audio.

When content of other than Japanese (for example, French) as the original language is reproduced from a disc, the user needs to know the original language of content recorded on the disc with reference to the package or booklet attached to the disc. After the user knows the original language, he or she needs a time to press the language selection button of the player apparatus several times until the original language is selected.

In this case, when the priority language of audio to be reproduced is preset to French for example in the initial setting of the player apparatus, only when content is reproduced from the disc, audio of French is automatically selected. However, when content is reproduced from a disc whose original language is another language for example English, the user needs to change the initial setting of the player apparatus. Thus, the user feels very inconvenient.

DISCLOSURE OF THE INVENTION

Therefore, an object of the present invention is to provide a reproducing apparatus, a reproducing method, a reproducing program, a recording medium, and a data structure that allow audio and a subtitle to be properly and automatically selected when content is reproduced from a disc.

To solve the foregoing problem, the present invention is a reproducing apparatus of reproducing content data from a disc-shaped recording medium, comprising read means for reading data from a recording medium on which content data containing at least a video stream, one or a plurality of audio streams corresponding to the video stream and a production control program with which reproduction of the content data is controlled have been recorded; player means for reproducing the content data according to the reproduction control program; and first mode setting means for setting a first mode to the player means such that it automatically selects an audio stream of an original language from the one or plurality of audio streams when the content data are reproduced.

In addition, the present invention is a reproducing method of reproducing content data from a disc-shaped recording medium, the method comprising the steps of reading data from a recording medium on which content data containing at least a video stream, one or a plurality of audio streams corresponding to the video stream, and a production control program with which reproduction of the content data is controlled have been recorded; reproducing the content data according to the reproduction control program; and setting a first mode to the content reproduction step such that an audio stream of an original language is automatically selected from the one or plurality of audio streams when the content data are reproduced.

In addition, the present invention is a reproducing program causing a computer device to execute a reproducing method of reproducing content data from a disc-shaped recording medium, the reproducing method comprising the steps of reading data from a recording medium on which content data containing at least a video stream, one or a plurality of audio streams corresponding to the video stream, and a production control program with which reproduction of the content data is controlled have been recorded; reproducing the content data according to the reproduction control program; and setting a first mode to the content reproduction step such that an audio stream of an original language is automatically selected from the one or plurality of audio streams when the content data are reproduced.

In addition, the present invention is a recording medium on which content data containing at least a video stream, one or a plurality of video streams corresponding to the video stream, a reproduction control program with which reproduction of the content data is controlled, and stream information describing at least information which identifies each of one or a plurality of audio streams such that the information which identifies the audio stream used as an original language comes first have been recorded.

In addition, the present invention is a data structure comprising a video stream; content data containing one or a plurality of audio streams corresponding to the video stream; a reproduction control program with which reproduction of the content data is controlled; and stream information containing at least information which identifies each of the one or plurality of audio streams such that the information which identifies the audio stream used as an original language comes first.

As described above, according to the present invention, at least content data containing a video stream and one or a plurality of audio streams corresponding to the video stream and a reproduction control program with which reproduction of the content data is controlled have been recorded on a recording medium. When a reproducing apparatus reproduces content data from the recording medium according to the reproduction control program reproduced therefrom, a mode in which an audio stream of an original language is automatically selected from one or a plurality of audio streams is set. The user can enjoy content of the original language reproduced from the disc without need to check the original language of the content and set the original language to the reproducing apparatus.

In addition, according to the present invention, at least content data containing a video stream and one or a plurality of audio streams corresponding to the video stream, a reproduction control program with which reproduction of the content data is controlled, and stream information representing at least information that identifies each of one or a plurality of audio streams in such a manner that information identifying an audio stream of the original language comes first in the stream information have been recorded on a recording medium. Thus, a reproducing apparatus that reproduces content from the disc can check an arrangement of the information that identifies audio streams in the stream information and identifies the audio stream of the original language.

In addition, a data structure according to the present invention contains at least content data containing a video stream and one or a plurality of audio streams corresponding to the video stream, a reproduction control program with which reproduction of the content data is controlled, and stream information representing at least information that identifies each of one or a plurality of audio streams such that information identifying an audio stream of the original language comes first in the stream information. Thus, when an arrangement of information that identifies audio streams in the stream information is checked, the audio stream of the original language can be identified.

At this point, without need to add information representing an original language to an audio stream used as the original language or information that identifies the audio stream, the audio stream of the original language can be identified.

As described above, as an effect of the present invention, when content is reproduced from the disc, audio streams and subtitle streams of different languages can be properly and automatically selected.

In addition, according to an embodiment of the present invention, as initial setting of audio of the player, attribute "original language" can be set. A language in which content was created can be automatically selected. Thus, as an effect of the present invention, the user can enjoy content without deterioration of original environment.

In addition, according to an embodiment of the present invention, even if the same language has been set to an audio stream and a subtitle stream as a result of automatic selection, the subtitle stream is automatically caused to be not displayed. Thus, the user does not need to manually operate the apparatus not to display an undesired subtitle. Thus, as an effect of the present invention, the user-friendliness improves.

BRIEF DESCRIPTION OF DRAWINGS

FIG. 4 is a schematic diagram describing three statuses of the movie player;

FIG. 6 is a schematic diagram showing examples of events that occur while a play list is being reproduced;

FIG. 7 is a schematic diagram showing a list of examples of properties of a movie player object;

FIG. 8 is a schematic diagram showing a list of examples of methods of the movie player object;

FIG. 9 is a schematic diagram showing examples of key inputs as user's inputs;

FIG. 10 is a schematic diagram showing examples of key inputs as user's inputs;

FIG. 11A, FIG. 11B and FIG. 11C are schematic diagrams showing examples of control commands according to key inputs;

FIG. 12 is a schematic diagram showing examples of events according to key inputs;

FIG. 13 is a schematic diagram showing examples of event handlers;

FIG. 14 is a schematic diagram showing examples of event handlers;

FIG. 22 is a schematic diagram showing an example of a script program;

FIG. 24 is a schematic diagram showing an example of syntax of the entire structure of file "PLAYLIST.DAT";

FIG. 25 is a schematic diagram showing an example of the internal structure of block PlayItem( );

FIG. 26 is a schematic diagram showing an example of the internal structure of block PlayListMark( );

FIG. 27 is a schematic diagram describing field mark_type of block Mark( );

FIG. 29 is a schematic diagram showing an example of syntax that represents the entire structure of clip AV stream file "XXXXX.CLP";

FIG. 30 is a schematic diagram describing correlation of block StreamInfo( ) and an elementary stream;

FIG. 31 is a schematic diagram showing an example of the internal structure of block StaticInfo( );

FIG. 32 is a schematic diagram showing an example of the internal structure of block DynamicInfo( );

FIG. 33 is a schematic diagram showing an example of the internal structure of block EP_map( );

FIG. 35A and FIG. 35B are a functional block diagram describing in detail the operation of the disc reproducing apparatus;

FIG. 39 is a schematic diagram showing examples of values of property audioFlag;

FIG. 40 is a schematic diagram showing examples of values of property subtitleFlag;

FIG. 41A and FIG. 41B are schematic diagrams showing a list of examples of arguments of method play( );

BEST MODES FOR CARRYING OUT THE INVENTION

Next, an embodiment of the present invention will be described in the following order.

| | |
|---|---|
| 1. | UMD video standard |
| 2. | Player model according to UMD video standard |
| 3. | Event model of movie player |
| 4. | Movie player object |
| 5. | Example of script program |
| 6. | File management structure |
| 7. | Disc reproducing apparatus |
| 8. | Automatic selection of audio and subtitle streams |
| 1. | UMD video standard |

For easy understanding of the present invention, a system according to an embodiment of the present invention will be described. According to the embodiment of the present invention, a player model is described with a script language called an ECMA script. The ECMA script is a script language for a cross platform based on JavaScript (registered trademark) and standardized by European Computer Manufacturers Association (ECMA). The ECMA script has higher compatibility with HTML documents. In addition, since the ECMA script allows original objects to be defined, the ECMA script can be suitably used for a player model according to the present invention.

In the following description, the standard that uses a script language based on the ECMA script and that accords to the embodiment of the present invention is referred to as UMD (Universal Media Disc: registered trademark) video standard. A script part of the UMD video standard is referred to as the UMD video script standard.

Figure 1:
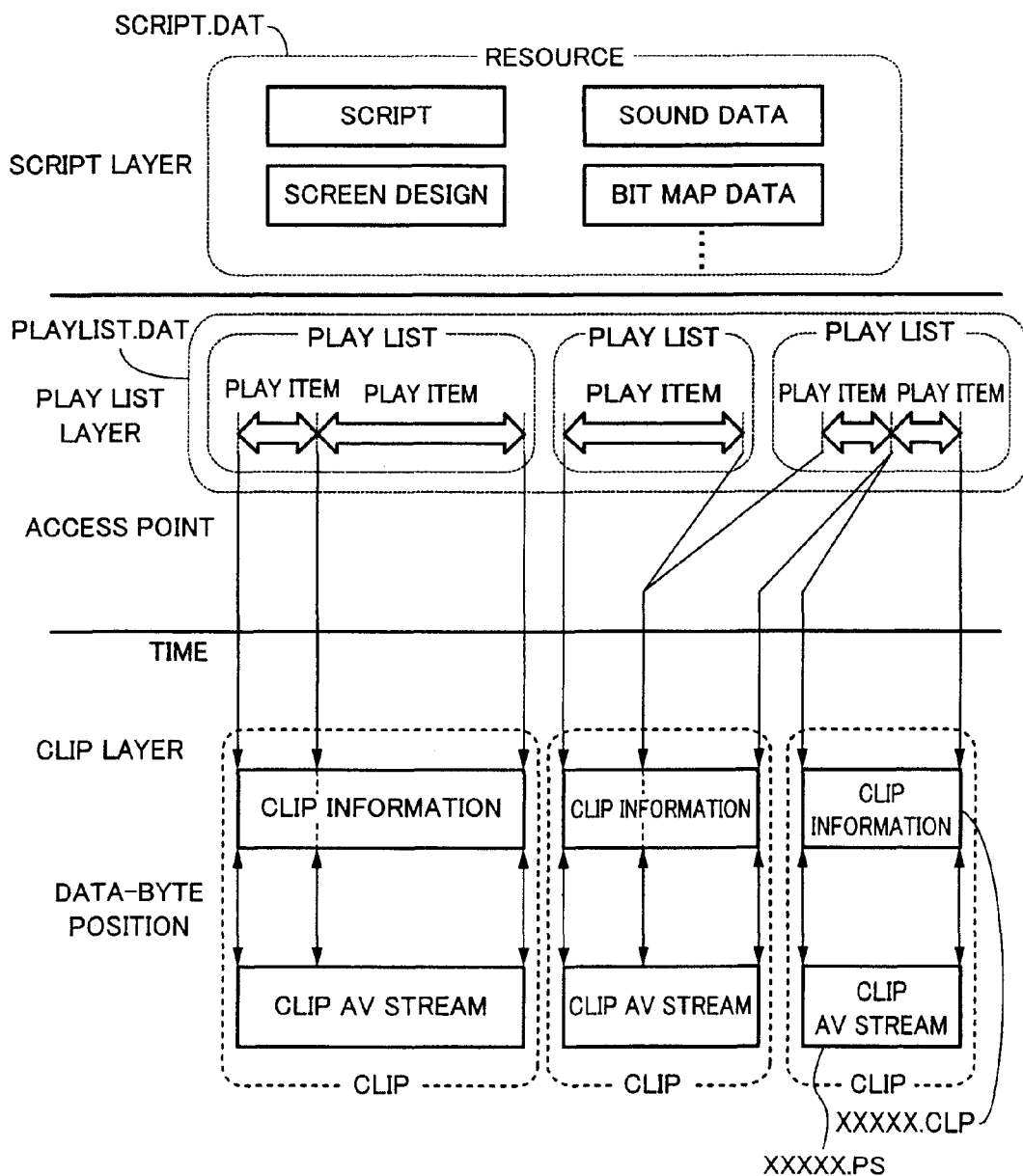
FIG. 1 is a schematic diagram showing the structure of layers according to the UMD video standard.

Next, the UMD video standard will be described in brief. FIG. 1 shows the structure of layers of the UMD video standard. The UMD video standard defines a three-layer structure composed of a script layer, a play list layer, and a clip layer. Streams are managed according to this layer structure.

According to the UMD video standard, digitally encoded video data, audio data, and subtitle data are treated as an MPEG2 stream of which they have been multiplexed as an elementary stream according to the MPEG2 (Moving Picture Experts Group 2) system. An MPEG2 stream of which elementary streams of video data, audio data, and subtitle data have been multiplexed is referred to as a clip AV stream. A clip AV stream is stored in a clip AV stream file. When a clip AV stream file is recorded, a clip information file is created according to the clip AV file in the relation of 1 to 1. A pair of a clip information file and a clip AV stream file corresponding thereto is referred to as a clip.

A clip is a recording unit of a disc. The reproduction order of clips is managed in the play list layer higher than the clip layer. The play list layer is a layer that designates the reproduction path of clips. The play list layer contains one or a plurality of play lists. A play list is composed of a set of play items. A play item contains a pair of an IN point and an OUT point that represent the reproduction range of a clip. When play items are placed, clips can be reproduced in any order. A play item can redundantly designate clips. The IN point and the OUT point of a clip AV stream are designated with time stamps (intra-clip times). Time stamps are converted into byte positions of a clip AV stream file according to information of a clip information file.

A play list has a structure that reproduces play items that represent all or part of clips in a predetermined order. Only with a play list, the reproduction order of clips cannot be changed. In addition, a play list does not provide the user with an interactive function. According to the embodiment of the present invention, a plurality of play lists are collectively stored in one file "PLAYLIST.DAT."

The script layer is a layer composed of UMD video scripts as an extension of ECMA scripts as language specifications. An UMD video script is a script of which an ECMA script is extended to accomplish a special function based on the UMD video standard.

The script layer is an upper layer of the play list layer. The script layer is composed of a sequence of commands that designate the reproduction of a play list and that set a player. Commands in the script layer accomplish play list reproduction including a conditional branch so that one of streams according to a plurality of languages can be selected or streams can be reproduced according to a play list selected in a predetermined condition. An example of an application that uses play list reproduction including a conditional branch is a multi-story content. The script layer provides the user with an interactive function.

According to the embodiment of the present invention, the script layer is composed of one file "SCRIPT.DAT." File "SCRIPT.DAT" is managed as a resource. File "SCRIPT.DAT" contains script data described according to a real ECMA script, sound data for sound effects and so forth in button operations, a screen design composed of image data used for a background image and so forth of a menu screen, and image data (bit map data) for GUI parts such as button images.

2. Player Model According to UMD Video Standard

Next, a model of a reproducing apparatus (player) that reproduces data according to the UMD video standard, namely a player model, will be described. The player reads a script program, a play list, and a clip information file from a disc. Thereafter, the player reads a clip AV stream file in the reproduction order according to those files and reproduces video data, audio data, subtitle data, and so forth.

In the language specifications of the script program, a functional block that reproduces a play list is implemented as an object in the script program. According to the UMD video standard, the object that reproduces the play list is referred to as the movie player object. Commands that designate the reproduction of the play list and set the player are methods of the movie player object. The movie player object is controlled by the methods of the script layer. At this point, the movie player object requires a function that informs the script layer of a state change, a reproduction position, and so forth. This function corresponds to an operation that the movie player object issues an event to the script program. A process corresponding to the event is described as an event handler.

When a model of which the movie player object transfers information as an event to the script program and the script program controls the movie player object with a method is made, the script program can control the reproduction of a clip AV stream.

Figure 2:
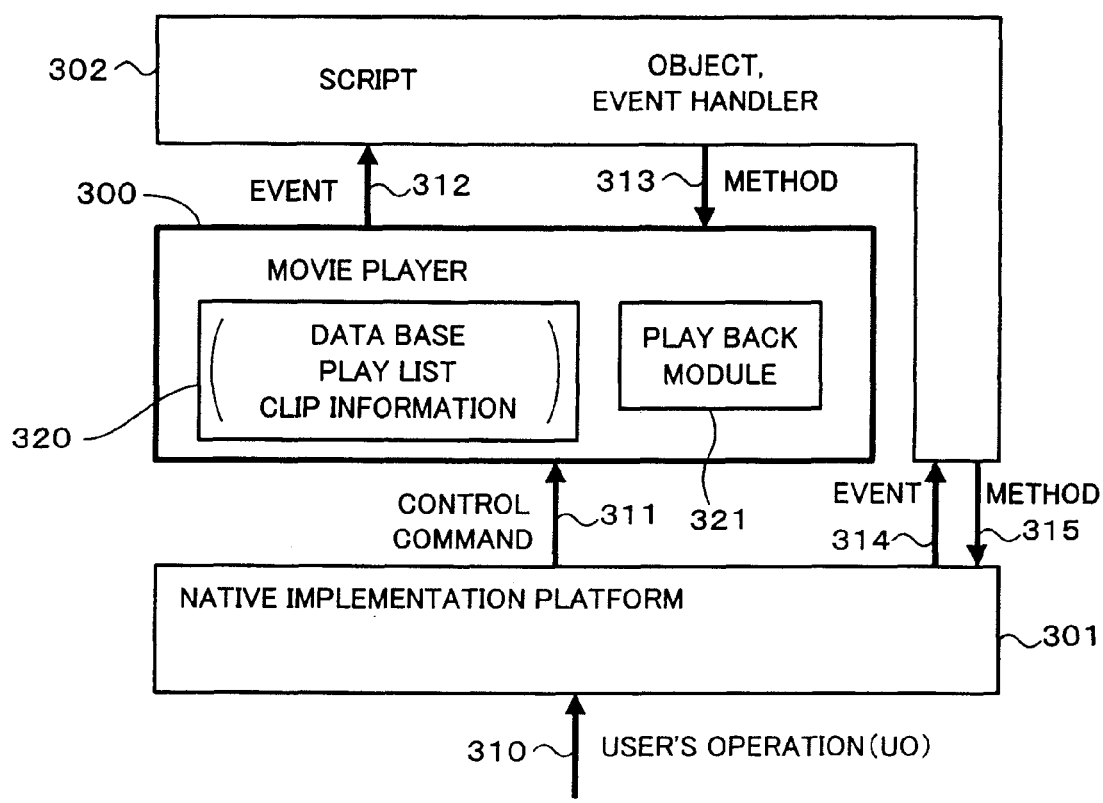
FIG. 2 is a schematic diagram showing an example of a player model according to an embodiment of the present invention.

FIG. 2 schematically shows an example of the player model according to the embodiment of the present invention. A movie player 300 is a module that reproduces video data, audio data, and subtitle data according to the UMD video standard. The movie player object is an object in a script program so that the script program operates a movie object. In other words, the movie player object is a script program that accomplishes the function of the movie player.

Since it is thought that the movie player 300 and the movie player object are substantially the same, in the following description, they are denoted by the same reference numeral.

In FIG. 2, the movie player 300 reads a clip AV stream file according to a database of a play list or clip information with a method of a lower layer (a native implementation platform 301 in the example shown in FIG. 2) as a user's input 310 or the like or a method of a script layer 302 as an upper layer and decodes and displays the clip AV stream.

The inside of the movie player object 300 depends on the implementation of the UMD video player that reproduces data from the UMD video disc. The script layer 302 provides APIs (Application Programming Interfaces) that are methods and properties as black-box objects. In this case, the UMD video player represents a real device that implements a movie player. All UMD video players implement a movie player according to the UMD video standard and have reproduction compatibility with other UMD video players.

As shown in FIG. 2, the movie player 300 has three input/output paths that are a path through which a control command 311 is received from the native implementation platform 301, a path through which the script layer 302 is informed of an event 312, and a path through which a method 313 is received from the script layer 302.

The control command 311 is a command that is received from the native implementation platform 301 and that controls the operation of the movie player object 300. The native implementation platform 301 is an interface between an original portion of the UMD video player as a real device and the movie player 300. The event 312 is a script event sent from the movie player 300 to the script layer 302. The method 313 is a method that a script program of the script layer 302 designates to the movie player 300.

The movie player object 300 has a database 320 for play lists and clip information according to the UMD video standard. The movie player object 300 masks the user's input 310. In addition, the movie player object 300 performs for example a process that converts the reproduction position designated by a time into a byte position of a clip AV stream with the database 320.

A playback module 321 of the movie player object 300 decodes a clip AV stream, which is an MPEG2 PS (Program Stream) of which video data, audio data, and subtitle data have been multiplexed. The playback module 321 has three states that are play, stop, and pause. The playback module 321 changes among these states with a control command and a method (see FIG. 3).

The script layer 302 is a layer that executes a script program according to the UMD video script standard, controls the movie player object 300, and displays data on the display. The script layer 302 accomplishes a scenario that the content creator side intends. The script layer 302 issues the method 313 to the movie player object 300. The script layer 302 receives the event 312 from the movie player object 300. The script layer 302 exchanges a key event 314 according to the user's input 310 and a method 315 that causes the native implementation platform 301 to display data on the display with the native implementation platform 301.

For example, buttons on the menu screen are generated by the native implementation platform 301 according to the method 315 supplied from the script program of the script layer 302 to the native implementation platform 301. When the user performs an operation such as selection or decision for one of the buttons, the key event 314 according to the user's input 310 is sent from the native implementation platform 301 to the script layer 302. The script program of the script layer 302 performs a process with the key event 314 according to the user's input 310.

Thus, the movie player 300 performs decode and display controls for video data, audio data, and subtitle data. On the other hand, the script layer 302 performs arrange and display processes for part images that compose graphical user interfaces such as buttons (hereinafter, these part images are referred to as GUI parts) and processes against selection and decision operations of the GUI parts.

The native implementation platform 301 is a platform for operations of the movie player object 300 and the script program. When the real UMD video player is hardware, the native implementation platform 301 is implemented as hardware so that the native implementation platform 301 intermediates a process between hardware and the player model.

The native implementation platform 301 receives the user's input 310 from the user and determines whether the received user's input 310 is a command for the movie player 300 or a command for a button generated and displayed in the script layer 302. When the determined result represents that the user's input 310 is a command for the movie player 300, the native implementation platform 301 converts the user's input 310 into the control command 311 that is an internal control command for the movie player 300 and issues a control command to the movie player 300.

When the determined result represents that the user's input 310 is a command of a GUI part generated and displayed in the script layer 302, the native implementation platform 301 informs the script layer 302 of the key event 314 according to the user's input 310. For example, the native implementation platform 301 can display for example a button image on the display according to the method 315 that the script layer 302 designates according to the key event 314. In other words, the native implementation platform 301 and the script layer 302 can directly exchange an event and a method not through the movie player 300.

Figure 3:
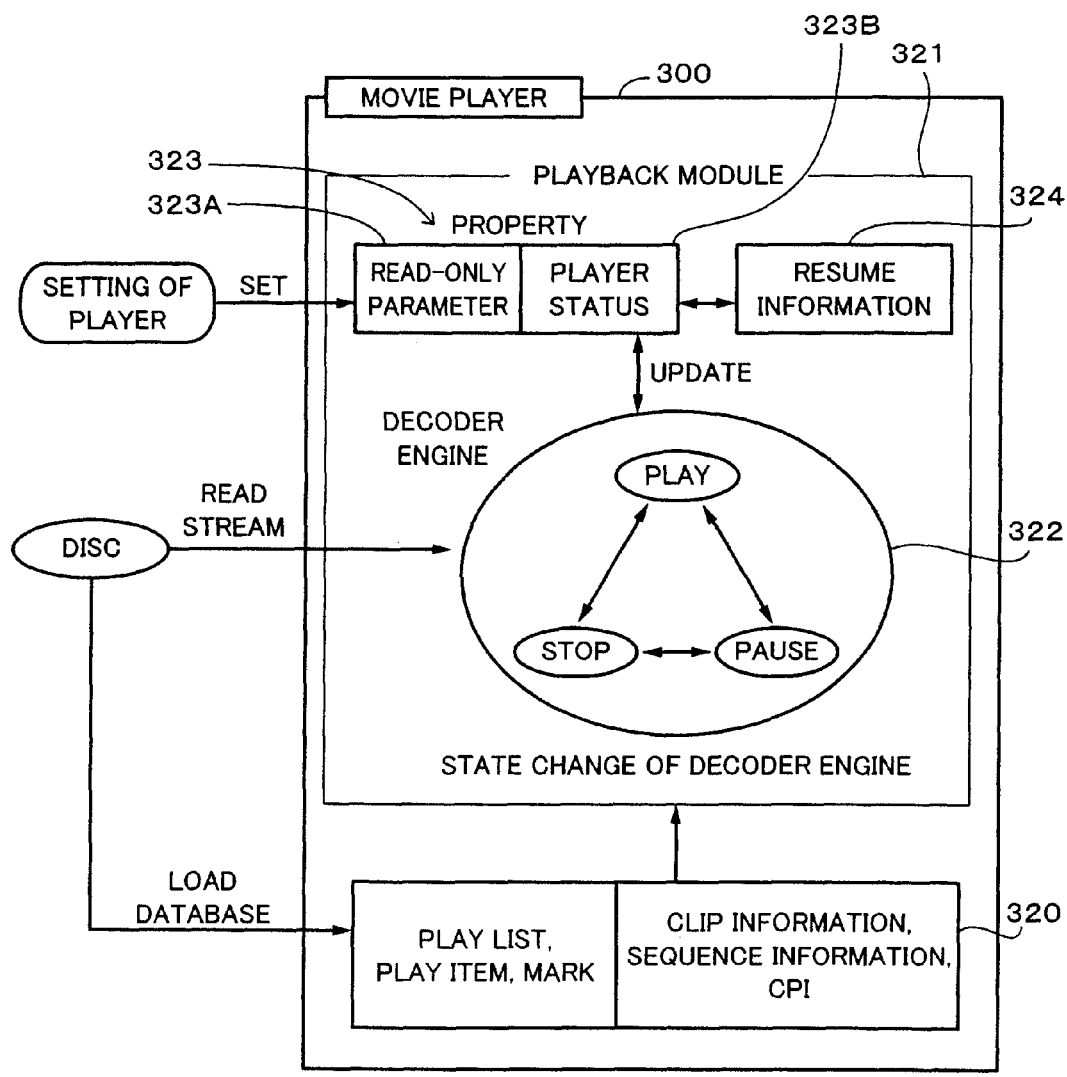
FIG. 3 is a schematic diagram showing an example of the internal structure of a movie player.

Next, the movie player 300 will be described in details. FIG. 3 shows an example of the internal structure of the movie player 300. As described above, the movie player 300 is composed of the database 320 and the playback module 321. The database 320 is an area that stores information of a play list read from the disc and information of clips, namely clip information.

The playback module 321 is composed of a decoder engine 322 and a property 323. The property 323 is a value that represents the state of the playback module 321. The property 323 has two types of a property 323A (read-only parameter) whose value depends on the initial setting of the movie player 300 like a language code and a property 323B (player status) whose value depends on the state of the playback module 321.

The value of the property 323A, whose value depends on the initial setting, is set by a native device for example a real device. Thus, the value of the property 323A is not changed by a play list, clip information, and a script program. The value of the property 323A can be read from a script program.

In contrast, the value of the property 323B, which represents the state of the playback module 321, can be read from a script program. In addition, the value of the property 323B can be written from some script programs.

In this operation model, it is assumed that a play list and clip information are pre-loaded from the disc before a clip AV stream is reproduced. Instead, the operations of the movie player model may be accomplished in another implementation.

The movie player object 300 reproduces a play list designated by the script layer 302 or the native implementation platform 301. For example, the movie player 300 references the database 320 and obtains the reproduction position of the clip AV stream as the byte position of the file according to the designated play list. In the playback module 321, the decoder engine 322 controls the decoding of the clip AV stream according to the information of the reproduction position.

As shown in FIG. 4, the movie player 300 has three states of play, stop, and pause depending on the reproduction state of a play list. The play state represents that a play list is being reproduced and a time has elapsed. The play state includes regular reproduction, variable speed reproduction such as double speed reproduction and ½ speed reproduction, fast forward, and fast reverse. The pause state represents that a play list is being reproduced and time axis stops. So-called frame reproduction, of which frames are forward and reverse reproduced, is a state of which the pause state and the play state are repeated. The stop state represents that a play list is not being reproduced.

The state of the movie player 300 depends on the state change among play, pause, and stop of the decoder engine 322 of the movie player 300. The value of the property 323B is updated according to the state change of the decoder engine 322.

Resume information 324 stores the state that exits immediately before the stop state occurs. After the movie player 300 decodes a play list, when the movie player 300 is in the play state, if the state of the movie player 300 is changed to the stop state, the resume information 324 stores the state that exists immediately before the stop state occurs. In addition, the resume information 324 for each title of the disc can be stored in a nonvolatile memory of the player as hardware. The disc has unique identification information (referred to as title ID) for each title of the disc. The resume information 324 and the identification information are correlatively stored. Thus, when the state of the disc having the title according to the identification information is changed from the stop state to the play state, data can be reproduced from the position at which the stop state occurred.

3. Event Model of Movie Player

Next, an event model of the movie player 300 will be described. In the play state, the movie player 300 reproduces a play list and generates various events. The events execute process programs described as scripts and referred to as event handlers. The event handlers are methods called upon occurrence of events. A program execution model that starts executing a process program upon occurrence of an event is referred to as an event driven model. In an event driven model, an irregular event occurs. When the event occurs, a predetermined program is executed. According to the embodiment of the present invention, a script program controls the operations of the movie player object 300 with an event handler group.

Figure 5:
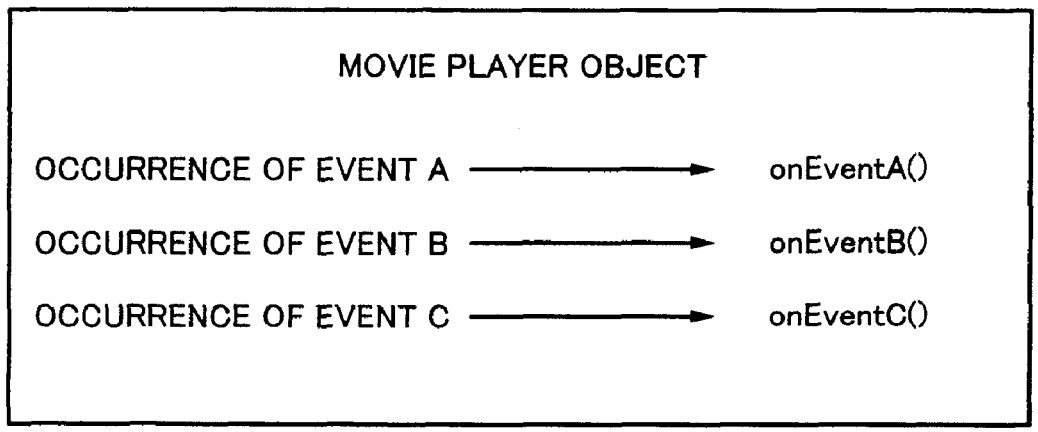
FIG. 5 is a schematic diagram showing an event model of the movie player according to the embodiment of the present invention.

FIG. 5 schematically shows an event model of the movie player 300 according to the embodiment of the present invention. In FIG. 5, event handlers onEventA( ), onEventB( ), and onEventC( ) are interfaces. The contents of the event handlers are described as scripts. The contents of the event handlers are created and implemented by for example the content creator side. In the UMD video scrip standard, an event handler is provided for each event of which the movie player object 300 informs the script program. In the example shown in FIG. 5, it is decided that a process program executed upon occurrence of event A is event handler onEventA( ). This applies to event B and event C. Thus, when event B occurs, corresponding event handler onEventB( ) is executed. When event C occurs, corresponding event handler onEventC( ) is executed.

Since the system side selects an event handler called upon occurrence of an event, the content creator side does not need to describe a process that determines what event occurred in a script program.

FIG. 6 shows examples of events that occur while a play list is being reproduced. Since chapter mark ChapterMark is described at the beginning of play list PlayList, when the play list is reproduced from the beginning, event Chapter corresponding to the chapter mark occurs. Whenever the chapter is changed to another chapter, the script layer 302 is informed of event Chapter and the corresponding event handler onChapter is executed. When reproduction time for event mark EventMark elapses, a corresponding mark event occurs. At the end of the play list, the movie player 300 pauses the reproduction of the play list and informs the script layer 302 of event PlayListEnd. The script layer 302 side causes the movie player 300 to start reproducing another play list in the corresponding event handler onPlayListEnd( ). In such a manner, the movie player 300 continues to reproduce a sequence of play lists in the order that the content creator side intended.

In such a manner, while the player is operating, various events occur. When an upper level program is informed of an occurrence of an event, the upper level program can grasp the state of the player. When the upper level program provides programs (event handlers) that are executed according to events of which it is informed, it can handle various events. Events and event handlers will be described later.

When the content creator side has not described an event handler, the upper program executes an operation (default event handler) built in the player and that is defined in the standard or ignores the event. When no process is required, if an event handler according to the event is not described, the event can be actively ignored.

As event models, there may be an event listener model, a single-method model, and so forth. In an event listener model, an object registers a listener according to a predetermined event to the player object. When an event that occurs in the player object is an event that has been registered, the player object transmits the event to the object that has registered the event. The object executes a corresponding method. In a single-method model, one method is called whatever event occurs.

The event model according to the embodiment of the present invention is simpler than an event listener model that requires processes such as event registration process and event deletion process. The single-method model needs to know what event occurred and describe in the method a pre-process that changes a process routine according to each event that occurs. Since the method is implemented by the content creator side, even if the model is simple, the load of the content creator side increases. In addition, whenever an event occurs, since one large process program (method) is called, a large memory area will be used and the execution speed will become slow. Thus, since the model according to the embodiment of the present invention provides process programs (event handlers) according to individual events, the model is superior to the other models in these points.

4. Movie Player Object

Next, the external specifications of the movie player object 300 will be described. Generally, an object defined according to the ECMA script language specifications has a property and a method. Like this object, as shown in FIG. 2 and FIG. 3, the movie player object 300 according to the embodiment of the present invention has a property and a method. When an external object designates an object name and a property name, the object can directly read and write a property. Instead, when method setXXX( ) (where "XXX" represents a property name) that sets a property value and method getXXX( ) that reads a property value are defined, the methods can read and write properties of other objects.

FIG. 7 shows a list of examples of properties that the movie player object 300 has. These properties correspond to the property 323 shown in FIG. 3. The properties that belong to the read-only parameters 323A shown in FIG. 3 are as follows. Property scriptVersion represents the version of the UMD video script. Property languageCode represents the language code of the menu display language that is set to the UMD video player. Property audioLanguageCode represents the language code of the audio language that is set to the UMD video player. Property subtitleLanguagecode represents the language code of the subtitle language that is set to the UMD video player.

When a disc is loaded into the movie player 300, a scrip file that is read from the disc is decided according to the language code represented by property languageCode that is set in the read-only parameter 323A. When the disc loaded into the movie player 300 does not have a script file according to the language, a default script file is read from the disc. For example, a file recorded at the beginning of a plurality of script files is read as a default script file.

Properties that belong to the player status 323B shown in FIG. 3 are as follows. Property playListNumber represents the play list number of a play list that is currently being reproduced. Property chapterNumber represents the chapter number of a chapter that is currently being reproduced. Property videoNumber represents the video stream number of a video stream that is currently being reproduced. Property audioNumber represents the audio stream number of an audio stream that is currently being reproduced. Property subtitleNumber represents the subtitle stream number of a subtitle stream that is currently being reproduced. Property playListTime represents the time of the play list when the beginning of the play list is 0. Property audioFlag designates ON/OFF of the audio reproduction and dual monaural LR. Property subtitleFlag represents ON/OFF of the subtitle indication.

The dual monaural is a mode of which left and right (L, R) channels of stereo audio are independently used as monaural audio channels.

When the movie player 300 is in the play state or the pause state, each property that belongs to the player status 323B represents these information. When the movie player 300 is changed to the stop state, each property that belongs to the player status 323B is backed up as the resume information 324. At this point, the contents of the player status 323B may be cleared.

FIG. 8 shows a list of examples of methods that the movie player object 300 has. The methods correspond to the method 313 shown in FIG. 3. Method play( ) reproduces video data. Method playChapter( ) designates a chapter and reproduces video data of the designated chapter. Method stop( ) stops reproducing video data. Method pause( ) pauses the reproduction of video data. Method playStep( ) reproduces video data step by step. Method changeStream( ) changes a video stream, an audio stream, and/or a subtitle stream. Method getPlayerStatus( ) obtains the play state, the stop state, the pause state, or the like of the movie player 300. Method reset( ) stops the reproduction of video data and clears the contents of the resume information 324.

According to the UMD video standard, video data can be displayed at a part of the display screen. The following four methods are methods that display video data at a part of the display screen. Method setpos( ) sets the display position of video data. Method getPos( ) obtains the display position of video data. Method setSize( ) sets the display size of video data. Method getSize( ) obtains the display size of video data.

In reality, the movie player 300 and the native implementation platform 301 are integrated. In other words, the movie player 300 UMD and the native implementation platform 301 are correlated as hardware, a UMD player that loads a disc and reproduces video data from the disc, and software that controls the UMD player. What portion is hardware and what portion is software depend on the implemented structure. For example, when the UMD player is a personal computer or the like, the other portions except for the disc dive are composed of software. When a single UMD player is used, besides the disc drive, for example the video decoder, the audio decoder, and so forth may be composed of hardware. Thus, methods, commands, and events exchanged between the movie player 300 and the native implementation platform 301 are not limited to those explicitly shown in FIG. 2.

On the other hand, with respect to key inputs of the user, as shown in FIG. 2, the user's input 310 is received first by the native implementation platform 301. In other words, the native implementation platform 301 receives a key input of the user as the user's input 310. The native implementation platform 301 determines whether the user's input 310 is a command to the movie player 300 or an event to a script program of the script layer 302. Depending on the determined result, the native implementation platform 301 generates the control command 311 or the key event 314 and informs the corresponding upper layer (movie player 300 or the script layer 302) of the generated control command 311 or key event 314.

FIG. 9 and FIG. 10 show examples of key inputs of the user's input 310. In FIG. 9 and FIG. 10, keys having prefix "VM" are abstracted virtual keys that do not depend on the implementation. FIG. 9 shows examples of key inputs with respect to the operations of the movie player 300. Key VK_POWER provides a function corresponding to a power key. Key VK_POWER_ON provides a function corresponding to a power ON key. Key VK_POWER_OFF provides a function corresponding to a power OFF key. Key VK_MENU provides a function corresponding to a menu key that displays a menu. Key VK_ENTER provides a function corresponding to an enter key that ends a command or data input. Key VK_RETURN provides a function that returns the process by one step.

Key VK_PLAY provides a function corresponding to a play key that starts the reproduction operation. Key VK_STOP provides a function corresponding to a stop key that stops the reproduction operation. Key VK_PAUSE provides a function corresponding to a pause key that pauses the reproduction operation. Key VK_FAST_FORWARD provides a function corresponding to a fast forward key that performs the fast forward reproduction operation. Key VK_FAST_REVERSE provides a function corresponding to a fast reverse key that performs the fast reverse reproduction operation. Key VK_SLOW_FORWARD provides a function corresponding to a slow (forward) key that performs the forward slow reproduction operation. Key VK_SLOW_REVERSE provides a function corresponding to a slow (reverse) key that performs the reverse slow reproduction operation. Key VK_STEP_FORWARD provides a function corresponding to a step (forward) key that performs the forward step reproduction operation. Key VK_STEP_REVERSE provides a function corresponding to a frame (reverse) key that performs the reverse step reproduction operation.

FIG. 10 shows key inputs with respect to the menu operations. Key VK_NEXT provides a function corresponding to a next designation key that inputs a value that represents "next." Key VK_PREVIOUS provides a function corresponding to a previous designation key that inputs a value that represents "previous." With key VK_NEXT and key VK_PREVIOUS, the user can designate for example the movement to the next chapter and the previous chapter, respectively.

Key VK_UP provides a function corresponding to an up direction designation key that inputs a value that represents "up." Key VK_DOWN provides a function corresponding to a down direction designation key that inputs a value that represents "down." Key VK_RIGHT provides a function corresponding to a right direction designation key that input a value that represents "right." Key VK_LEFT provides a function corresponding to a left direction designation key that inputs a value that represents "left." Key VK_UP_RIGHT provides a function corresponding to an upper right direction designation key that inputs a value that represents "upper right." Key VK_UP_LEFT provides a function corresponding to an upper left direction designation key that inputs a value that represents "upper left." Key VK_DOWN_RIGHT provides a function corresponding to a down right direction designation key that inputs a value that represents "down right." Key VK_DOWN_LEFT provides a function corresponding to a down left direction designation key that inputs a value that represents "down left." With these direction keys, the user can designate for example the movement of the cursor on the display.

Key VK_ANGLE provides a function corresponding to an angle change key that designates an angle change operation for multi-angle video data. Key VK_SUBTITLE provides a function corresponding to a subtitle change key that designates English subtitle, Japanese subtitle, and subtitle ON/OFF. Key VK_AUDIO provides a function corresponding to an audio change key that designates an audio mode such as surround mode or bilingual mode. Key VK_VIDEO_ASPECT provides a function corresponding to an aspect change key that changes an aspect ratio of video data. Key VK_COLORED_KEY_1 provides a function corresponding to a colored function key 1. Key VK_COLORED_KEY_2 provides a function corresponding to a colored function key 2. Key VK_COLORED_KEY_3 provides a function corresponding to a colored function key 3. Key VK_COLORED_KEY_4 provides a function corresponding to a colored function key 4. Key VK_COLORED_KEY_5 provides a function corresponding to a colored function key 5. Key VK_COLORED_KEY_6 provides a function corresponding to a colored function key 6.

Since the functions of the key inputs shown in FIG. 9 are different in their roles from those of the key inputs shown in FIG. 10, the native implementation platform 301 needs to select destinations that are informed of the key inputs. As described above, key inputs shown in FIG. 9 designate the reproduction operations of video data, audio data, and subtitle data. When the native implementation platform 301 receives one of the key inputs shown in FIG. 9 as the user's input 310, the native implementation platform 301 converts the received key input into a command shown in FIG. 11A, FIG. 11B and FIG. 11C and informs the movie player 300 of the converted command.

On the other hand, since the key inputs shown in FIG. 10 are the user's input 310 to the GUI, the script layer 302, which structures a screen and generates buttons, needs to be informed of these inputs. When the native implementation platform 301 receives one of key inputs shown in FIG. 10 as the user's input 310, the native implementation platform 301 converts the key input into the event 314 shown in FIG. 2 and informs the script layer 302 of the event 314. FIG. 12 shows examples of the key event 314 according to the key inputs.

FIG. 9 and FIG. 10 show also key inputs with respect to stream change operations such as key VK_ANGLE, key VK_SUBTITLE, and key VK_AUDIO. These key inputs are key inputs that accomplish the same functions as stream change methods that the script program performs to the movie player 300.

Next, commands shown in FIG. 11A, FIG. 11B and FIG. 11C will be described in detail. Command uo_timeSearch (playListTime) designates the reproduction of a play list that is being reproduced from a designated time. Argument playListTime represents the time of the play list when the beginning of the play list is 0. Since this command does not designate a play list number, the time represented by argument playListTime is a designated time in the range of the play list being reproduced. Command uo_play( ) designates the start of the reproduction at a predetermined reproduction speed such as regular reproduction speed. The start position of the play list is decided according to the resume information 324. When there is no information corresponding to the resume information 324, the user's operation is invalidated. This command corresponds to the execution of method play( ) without the play list number designated. With this command, the user cannot designate a play list number.

Command uo_playChapter(chapterNumber) starts reproducing the play list being reproduced from a chapter designated by argument chapterNumber. Without the chapter number designated, this command starts reproducing the play list from the beginning of the chapter being reproduced. This command corresponds to method playChapter( ) without the chapter number designated. Command uo_playPrevChapter( ) starts reproducing the play list from the immediately previous chapter. Command uo_playNextChapter( ) starts reproducing the play list from the immediately next chapter. Command uo_stop( ) stops reproducing the play list.

Command uo_jumpToEnd( ) jumps to the end of the play list. This command corresponds to a user's operation that causes the movie player 300 to stop the reproduction and generate event playListEnd. According to this command, the script layer 302 executes event handler onPlayListEnd. Command uo_forwardScan(speed) forward reproduces the play list at a reproduction speed designated by argument speed. Command uo_backwardScan(speed) backward reproduces the play list at a reproduction speed designated by argument speed. Argument speed of these commands uo_forwardScan(speed) and uo_backwardScan(speed) depends on the implementation of the UMD video player.

Command uo_playStep(forward) forward reproduces the play list step by step. Command uo_playStep(backward) backward reproduces the play list step by step. Command uo_pauseOn( ) pauses the reproduction of the play list according to a user's operation. Command uo_pauseOff( ) cancels the pause state of the reproduction of the play list according to a user's operation.

Command uo_changeAudioChannel(value) changes the channel of audio data or one channel of dual monaural reproduction. When this command is executed, the value of flag audioFlag needs to be accordingly changed. Command uo_setAudioEnabled(Boolean) turns ON/OFF the audio stream. When this command is executed, the value of flag audioFlag needs to be accordingly changed. Command uo_setSubtitleEnabled(Boolean) turns ON/OFF the subtitle stream. When this command is executed, the value of flag subtitleFlag needs to be accordingly changed. Command uo_angleChange( ) changes the display angle. When the movie player 300 is informed of the user's operation for this command, the movie player 300 informs the script layer 302 of event angleChange. Command uo_audiochange(audioStreamNumber) changes the audio stream to be reproduced. Command uo_subtitleChange(subtitleStreamNumber) changes the subtitle stream to be reproduced.

Next, the relationship between events shown in FIG. 12 and methods of the movie player 300 will be described in detail. Event menu jumps to a menu. The native implementation platform 301 informs the script layer 302 rather than the movie player 300 of this event. When the script layer 302 receives event menu, the script layer 302 executes event handler onMenu. Event exit is an event that the native implementation platform 301 issues when it completes the UMD video application. When the script layer 302 receives event exit, the script layer 302 executes event handler onExit.

Event up, event down, event left, event right, event focusIn, event focusOut, event push, and event cancel are events that occur when button images as GUI parts on the screen are focused. The native implementation platform 301 informs the script layer 302 rather than the movie player 300 of these events. When a button image is focused, for example the cursor displayed on the screen represents the coordinates of the button image so that the button image can be selected. Event up, event down, event left, and event right occur when an up button image, a down button image, a left button image, and a right button image are focused, respectively. Event focusIn occurs when any button image is focused. Event focusOut occurs when any focused button image is defocused. Event push occurs when a press operation is performed for any focused button image. Event cancel occurs when a cancel operation is performed against the press operation for any button image.

Event autoPlay and event continuePlay are events that cause the script layer 302 to start executing a script. Event autoPlay is an event that causes a script to automatically start executing when a disc is loaded. Event continuePlay causes a script to resume executing from the position that the script was stopped according to for example the resume information 324 when a disc is loaded.

There are programs that are executed when events shown in FIG. 12 occur. These programs corresponding to the events are referred to as event handlers. Events and event handlers can be correlated using for example names. For example, event handler names are created by adding a prefix "on" to event names. FIG. 13 and FIG. 14 show examples of event handlers. When the content creator describes the contents of event handlers, the UMD video player can perform various operations that the content creator intends.

FIG. 13 shows examples of events that the movie player 300 has and corresponding event handlers. Events shown in FIG. 13 correspond to the event 312 shown in FIG. 2. The movie player 300 informs the script layer 302 of the events shown in FIG. 13. The event handlers are kinds of interfaces. The contents of the event handlers are implemented by the content creator using the script language. Since the event handlers have such a structure, when events occur, operations that the content creator intends can be accomplished.

Event mark and event handler onMark( ) are executed when an event mark is detected. An event mark is embedded in for example a play list. While the movie player 300 is reproducing the play list, the movie player 300 detects a play list from the play list. When the movie player 300 detects an event mark, the movie player 300 informs the script layer 302 of event mark. The script layer 302 executes event handler onMark( ) corresponding to event mark. Likewise, event playListEnd and event handler onPlayListEnd( ) are executed when the reproduction of a play list is completed. Event chapter and event handler onChapter( ) are executed when a chapter mark is detected. A chapter mark is embedded in for example a play list and detected by the movie player 300 while it is reproducing the play list.

Event angleChange and event handler onAngleChange( ) are executed when the angle change is designated by a user's operation. For example, when key input VK_ANGLE is input to the native implementation platform 301 by the user's operation as the user's input 310, the native implementation platform 301 converts the user's input 310 into command uo_angleChange( ) and supplies it to the movie player 300. The movie player 300 generates event angleChange corresponding to command uo_angleChange and supplies event angleChange to the script layer 302. The script layer 302 executes event handler onAngleChange( ) corresponding to event angleChange. Likewise, event audiochange and event handler onAudioChange( ) are executed when the audio change is designated by a user's operation. Event subtileChange and event handler onSubtileChange( ) are executed when the subtitle change is designated by a user's operation.

FIG. 14 shows examples of event handlers that the system object has. The event handlers shown in FIG. 14 are event handlers that the native implementation platform 301 has in advance. The native implementation platform 301 informs the script layer 302 of the event handlers.

Event menu and event handler onMenu( ) jump to a menu. Event menu is an event of which the native implementation platform 301 informs the script layer 302 when the menu key is pressed by a user's operation. The script layer 302 receives the event, executes the corresponding event handler onMenu( ), and arranges and displays GUI parts that compose a menu screen with event handler onMenu( ). Event exit and event handler onExit( ) are an event and a corresponding event handler that the native implementation platform 301 generates when it completes the UMD video application.

When a user' operation or the like designates the completion of the operation of the UMD video player, the native implementation platform 301 informs the script layer 302 of event exit. When the script layer 302 receives event exit, the script performs an exit process with event handler onExit( ). Event autoPlay, event handler onAutoPlay( ), event continuePlay, and event handler onContinuePlay( ) start executing corresponding scripts.

Besides event handlers for the system object, there are event handlers for buttons. However, event handlers for buttons do not closely relate to the present invention, their description will be omitted.

Figure 15:
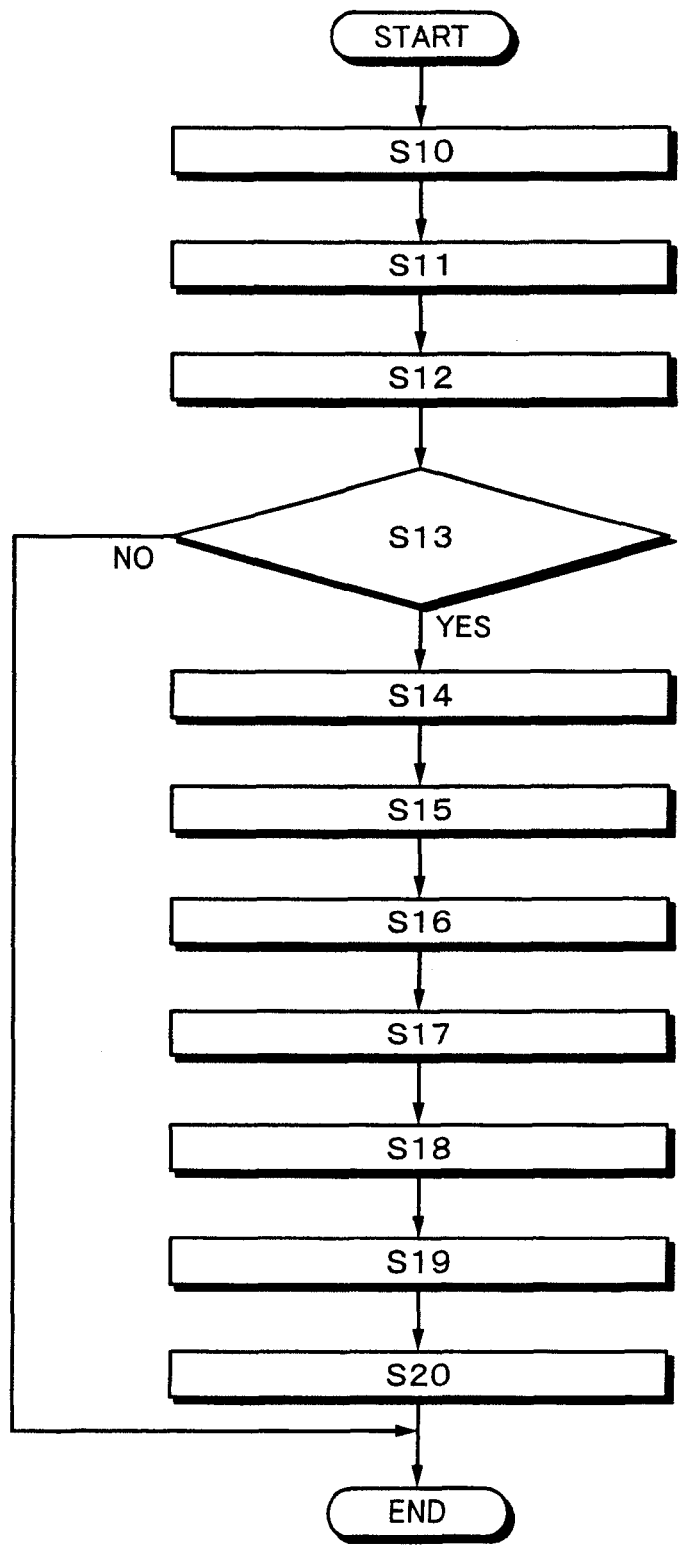
FIG. 15 is a flow chart showing an example of a process that executes a predetermined program according to a user's input event.

Next, with reference to a flow chart shown in FIG. 15, an example of a process that executes a provided program upon occurrence of a user's input event will be described in brief. FIG. 15 shows an example of which while the UMD video player is normally reproducing data from a disc, when the user presses the "next" key to causes the UMD video player to reproduce the next chapter, the UMD video player jumps to the next chapter according to the key input, starts reproducing the next chapter, and displays a prepared message on the screen.

While the UMD video player is normally reproducing data from the disc, when the user presses the key "next" on the remote control commander of the UMD video player (at step S10), key VK_NEXT is supplied as the user's input 310 to the native implementation platform 301. The native implementation platform 301 generates user command uo_playNextChapter( ) corresponding to the user's input 310 (at step S11). The native implementation platform 301 informs the movie player 300 of user command uo_playNextChapter( ).

When the movie player 300 receives command uo_playNextChapter( ), the movie player 300 searches the database 320 for the position of the next chapter mark based on the current reproduction position corresponding to play list information (at step S12). At step S13, it is determined whether the next chapter mark exists. When the determined result represents that the next chapter mark does not exist, the movie player 300 does not perform the chapter jump operation, but continues the current reproduction operation.

In contrast, when the determined result at step S13 represents that the next chapter mark exists, the flow advances to step S14. At step S14, the movie player 300 stops the current reproduction operation and obtains the byte position of the next chapter mark in the clip AV stream file from feature point information of the clip information file of the database 320. At step S15, the movie player 300 accesses the obtained byte position of the file and starts reproducing the stream from the position.

After step S16, a process that displays a message that informs the user that the chapter was changed on the screen is performed. When the chapter is changed and the reproduction is started from the beginning of the chapter, event chapter occurs (at step S16). For example, the movie player 300 detects the chapter mark at the beginning of the chapter, event chapter occurs. The movie player 300 informs the script layer 302 of event chapter. In addition to the event, the movie player 300 also informs the script layer 302 of the chapter number of the chapter to be jumped. The script layer 302 starts executing an event handler corresponding to the informed event, for example event handler onChapter( ) (at step S17).

In this example, it is assumed that an operation that displays a message that represents that the chapter was changed on the screen is described in the event handler. A script of the script layer 302 executes the event handler, obtains the chapter number of which the movie player 300 informed the script layer 302 when the event occurred (at step S18), and causes the native implementation platform 301 to display a predetermined message that represents for example the beginning of the obtained chapter number on the screen. According to the command, the native implementation platform 301 displays the message on the screen (at step S19) and completes the process of the event handler (at step S20).

In the foregoing process, when the user operates the key "next" that causes the movie player 300 to start reproducing the next chapter, the movie player 300 performs the chapter jump operation and displays a message that represents the beginning of the chapter on the screen when the movie player 300 starts reproducing the next chapter to be jumped.

Thus, the user's input event causes the state of the movie player 300 to change. In addition, the user's input event causes a new event to occur. With new events, the movie player 300 can perform various processes.

Figure 16:
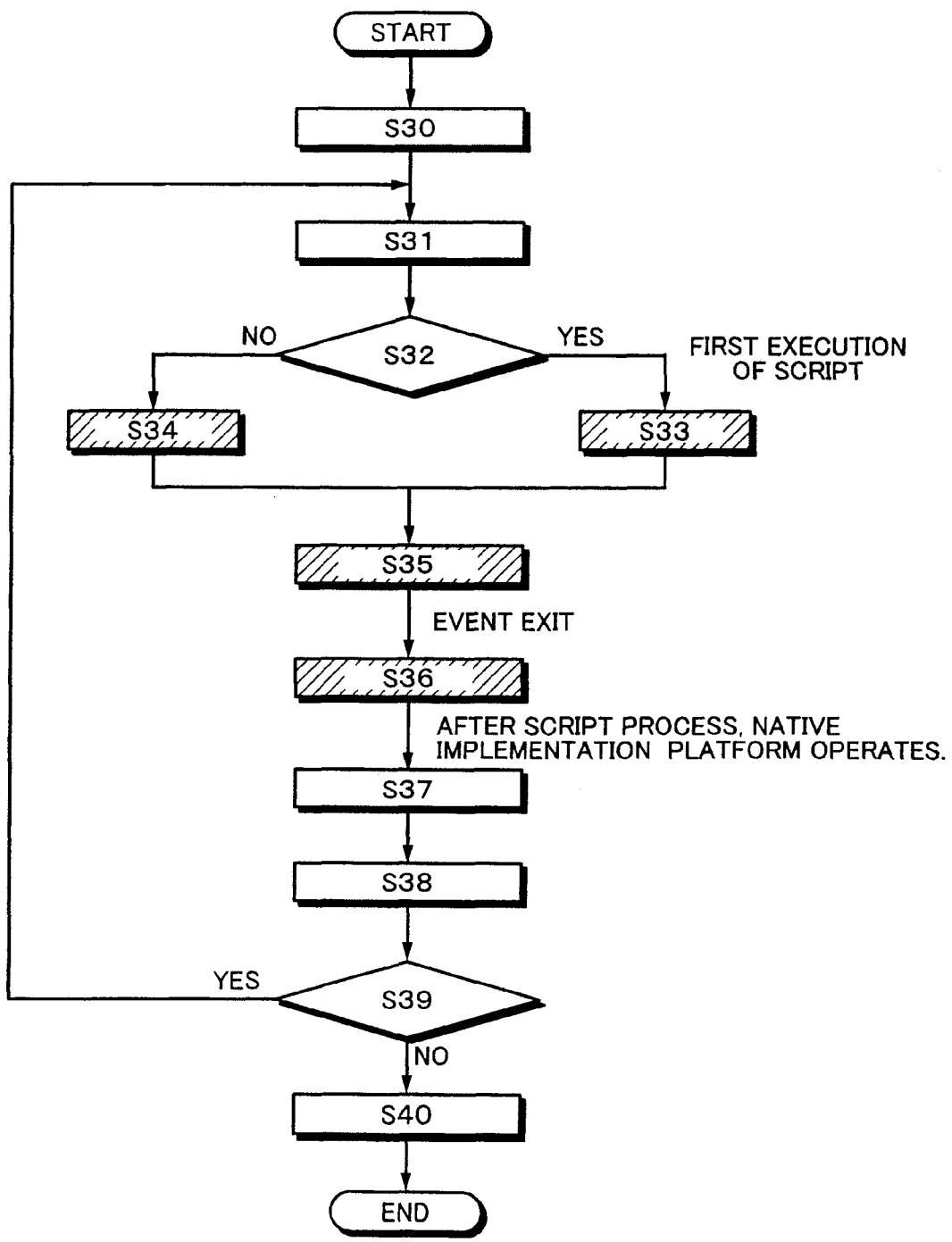
FIG. 16 is a flow chart showing a process performed after a disc is loaded into a UMD video player until the disc is ejected therefrom.
Figure 17:
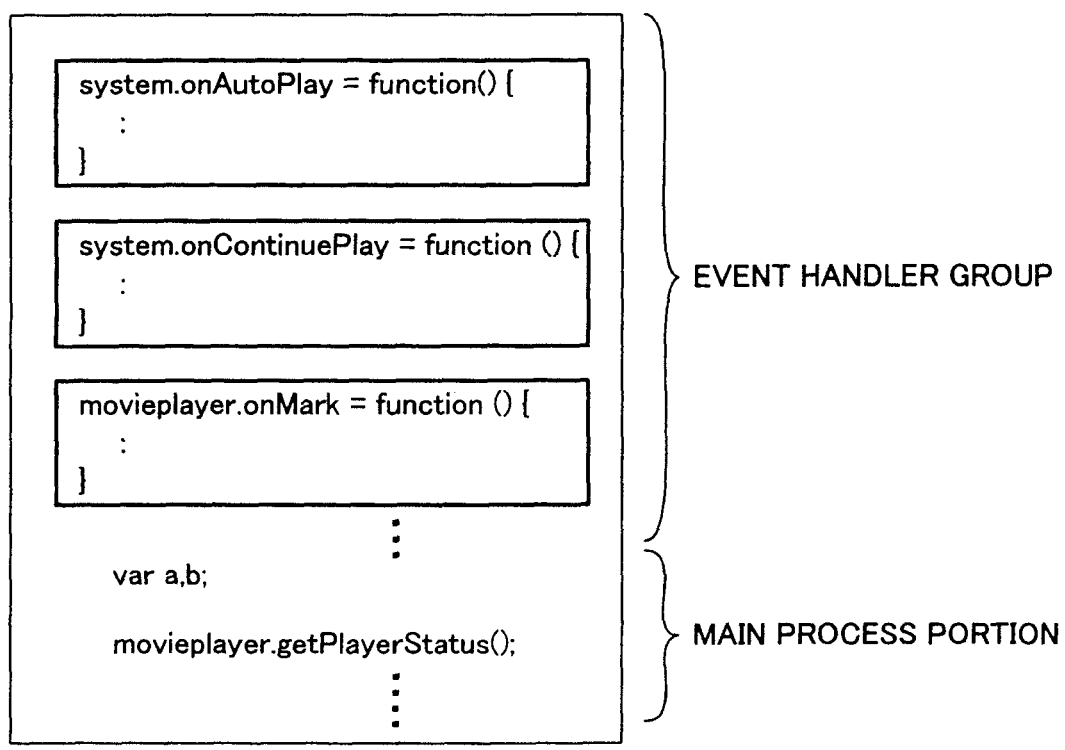
FIG. 17 is a schematic diagram showing an example of the structure of a script file.

FIG. 16 shows a process after a disc is loaded into the UMD video player until the disc is ejected therefrom. In FIG. 17, hatched steps represent states in which a script is being executed.

When the user places the disc in a predetermined position of the UMD video player, it loads the disc according to a predetermined operation so that the UMD video player can reproduce video data from the disc (at step S30). When the disc is loaded, the native implementation platform 301 references the resume information 324 and loads continuous reproduction information corresponding to the disc from the resume information 324 (at step S31).

Thereafter, the resume information 324 corresponding to the disc is referenced. It is determined whether the continuous reproduction information exists (at step S32). When the continuous reproduction information exists, the native implementation platform 301 informs the script layer of event continuePlay. The script layer 302 executes event handler onContinuePlay corresponding to the informed event continuePlay (at step S33). When the determined result at step S32 represents that the continuous reproduction information corresponding to the disc does not exist, the flow advances to step S34. At step S34, the native implementation platform 301 informs the script layer 302 of event autoPlay. The script layer 302 executes event handler onAutoPlay corresponding to event autoPlay.

At step S35, the reproduction operation for the disc and other operations are preformed according to the contents of event handler onAutoPlay and event handler onContinuePlay. An event that occurs corresponding to the reproduction operation for the disc and an event handler corresponding to the event are executed.

When the native implementation platform 301 generates event exit, the flow advances to step S36. At step S36, the script layer 302 executes event handler onExit corresponding to event exit. Event handler onexit executes a process that completes the UMD video application. Event exit is generated by the native implementation platform 301 according to the user's input 310 as a predetermined operation on for example the remote control commander.

When the script process according to event handler onExit is completed, the native implementation platform 301 operates. At step S37, the movie player 300 executes a process that stops the reproduction operation. At this point, the state that exists immediately before the movie player 300 stops the reproduction operation is stored as continuous reproduction information in the resume information 324. The reproduction operation for the disc is completed (at step S38). When the reproduction operation for the same disc is not preformed (at step S39), the flow advances to step S40. At step S40, the native implementation platform 301 ejects the disc and completes the sequence of steps of the process. When the reproduction operation for the same disc is performed, the flow returns to step S31.

FIG. 17 shows an example of the structure of a script file. As shown in FIG. 1, a script file is file "SCRIPT.DAT" that composes the script layer 302. A script file is composed of an event handler group and a main process portion. The event handler group is composed of one or a plurality of event handlers. Whenever the script layer 302 is informed of occurrence of an event, an event handler corresponding to the informed event is retrieved and executed. The main process portion describes definitions of global variables used in event handlers. The main process portion is initially executed one time.

Figure 18:
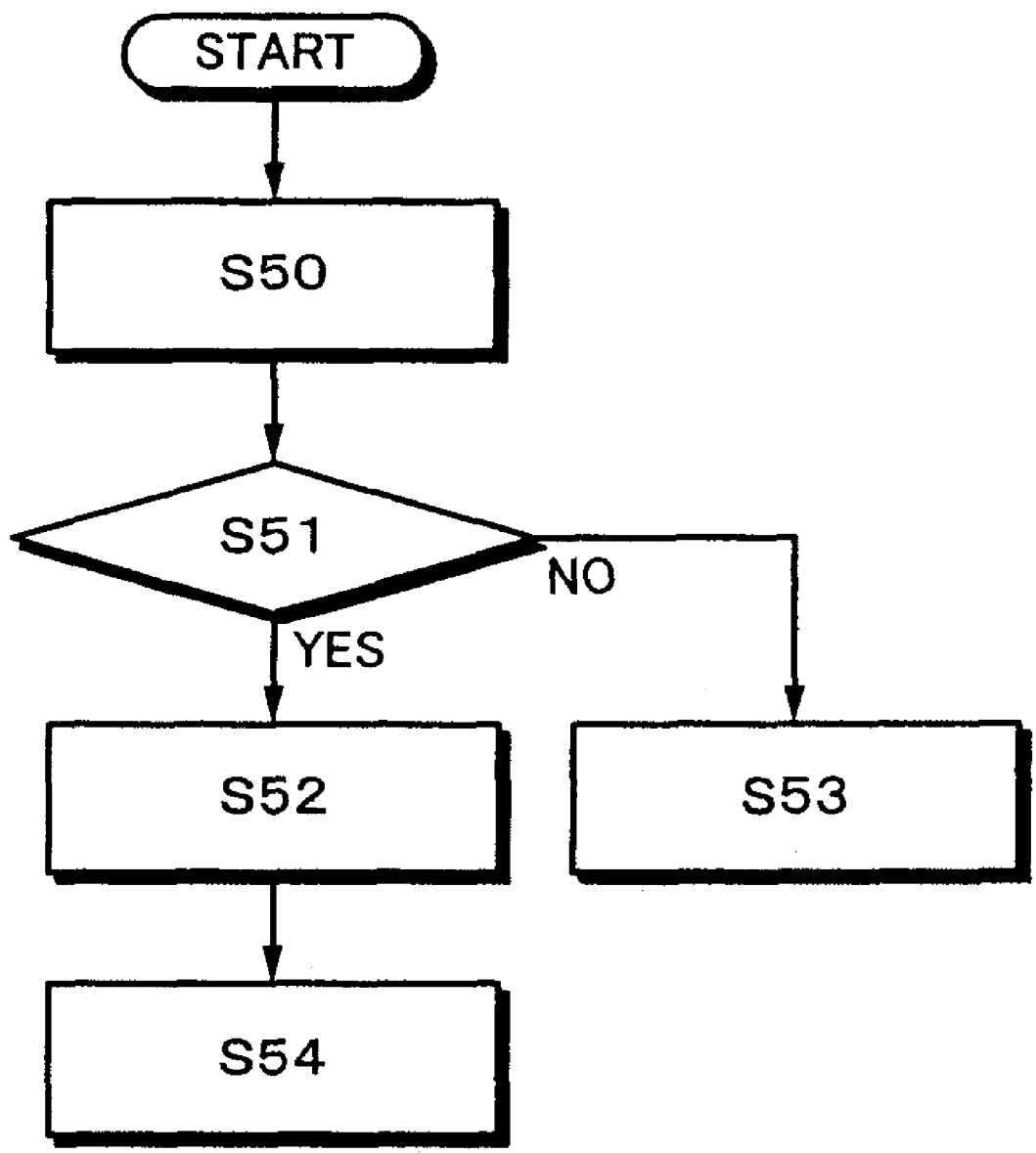
FIG. 18 is a flow chart showing an example of a procedure that executes event handler onAutoPlay( )

FIG. 18 shows an example of a procedure that executes event handler onAutoPlay( ). When the user loads a disc into the UMD video player 300 and causes it to perform the reproduction operation for the disc from the beginning (at step S50), the movie player 300 performs this procedure. At step S51, the native implementation platform 301 determines whether the script contains event handler onAutoPlay( ). When the script contains event handler onAutoPlay( ), the native implementation platform 301 informs the script layer 302 of event autoPlay (at step S52). At step S54, the script layer 302 executes event handler onAutoPlay( ). Thus, the movie player 300 automatically starts reproducing data from the loaded disc.

In contrast, when the determined result at step S51 represents that the script does not contain event handler onAutoPlay( ), the flow advances to step S53. The native implementation platform 301 informs the script layer 302 of event exit. In this case, when the user operates the menu key for the reproduction operation on the menu screen implemented in the native implementation platform 301, the movie player 300 starts reproducing data from the disc. When the script layer 302 has event handler onExit( ), the script layer 302 executes event handler onExit( ).

Figure 19:
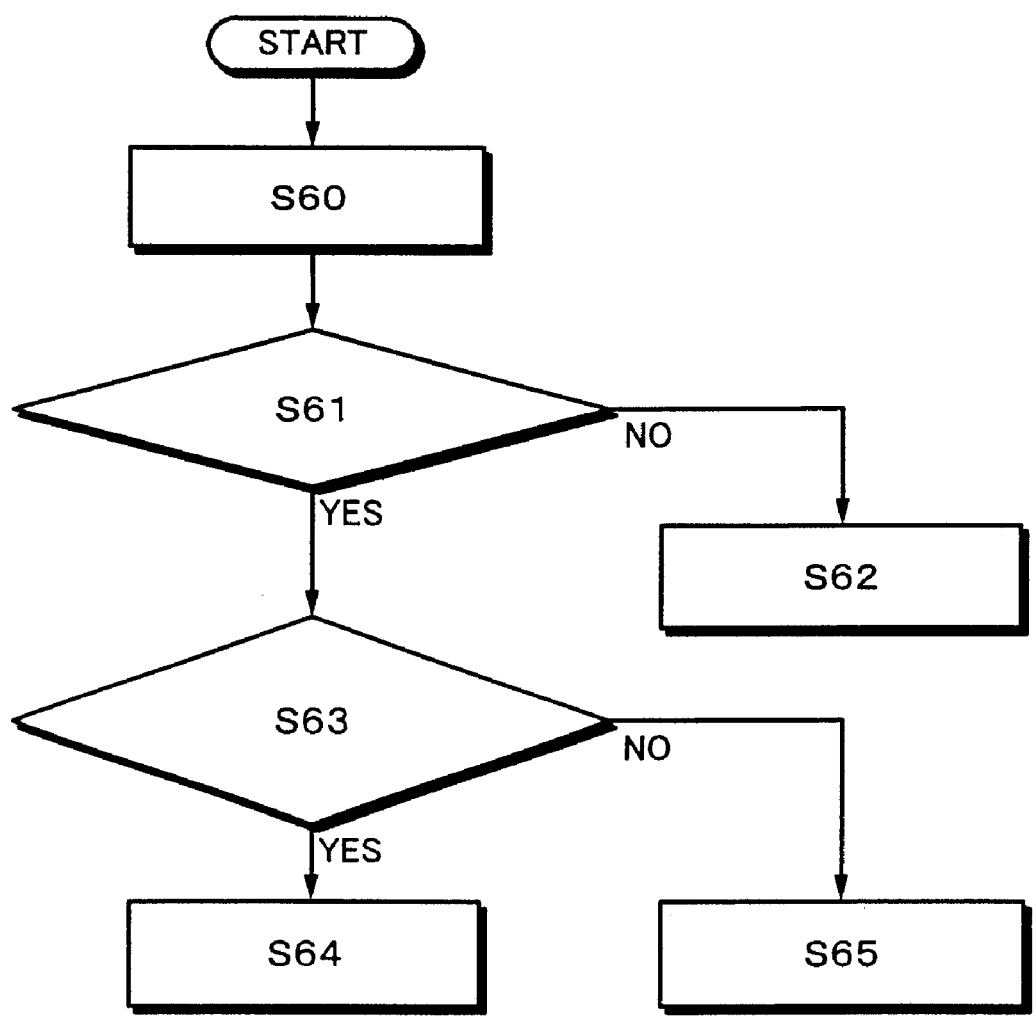
FIG. 19 is a flow chart showing an example of a procedure that executes event handler onContinuePlay( )

FIG. 19 shows an example of a procedure that executes event handler onContinuePlay( ). When the user loads a disc into the UMD video player and causes the movie player 300 to perform the continuous reproduction operation (at step S60), the movie player 300 performs this procedure. At step S61, the native implementation platform 301 determines whether the resume information 324 corresponding to the loaded disc exists. When the resume information 324 does not exist, the flow advances to step S62. At step S62, the movie player 300 performs the reproduction operation for the disc from the beginning.

When the resume information 324 corresponding to the loaded disc exists, the flow advances to step S63. At step S63, the native implementation platform 301 determines whether the script contains event handler onContinuePlay( ). When the script contains event handler onContinuePlay( ), the native implementation platform 301 informs the script layer 302 of event handler onContinuePlay( ). Accordingly, the script layer 302 executes event handler onContinuePlay( ) (at step S64). Thus, the movie player 300 resumes the reproduction for the loaded disc according to event handler onContinuePlay( ).

In contrast, when the determined result at step S63 represents that the script does not contain event handler onContinuePlay( ), the flow advances to step S65. At step S65, the native implementation platform 301 executes default event handler onContinuePlay( ). The default event handler onContinuePlay( ) simply starts the reproduction operation from the last reproduction end position according to for example the resume information 324.

User interfaces of event handler onAutoPlay and event handler onContinuePlay are not limited to those examples. Instead, various methods may be used. For example, in FIG. 19, at step S60, after the user causes the movie player 300 to perform the continuous reproduction operation, the native implementation platform 301 determines whether the resume information 324 corresponding to the loaded disc exists. Instead, inversely, first, the native implementation platform 301 may determine whether the resume information 324 corresponding to the loaded disc exists. When the resume information 324 exists, the native implementation platform 301 may ask the user whether to perform the continuous reproduction operation.

Figure 20:
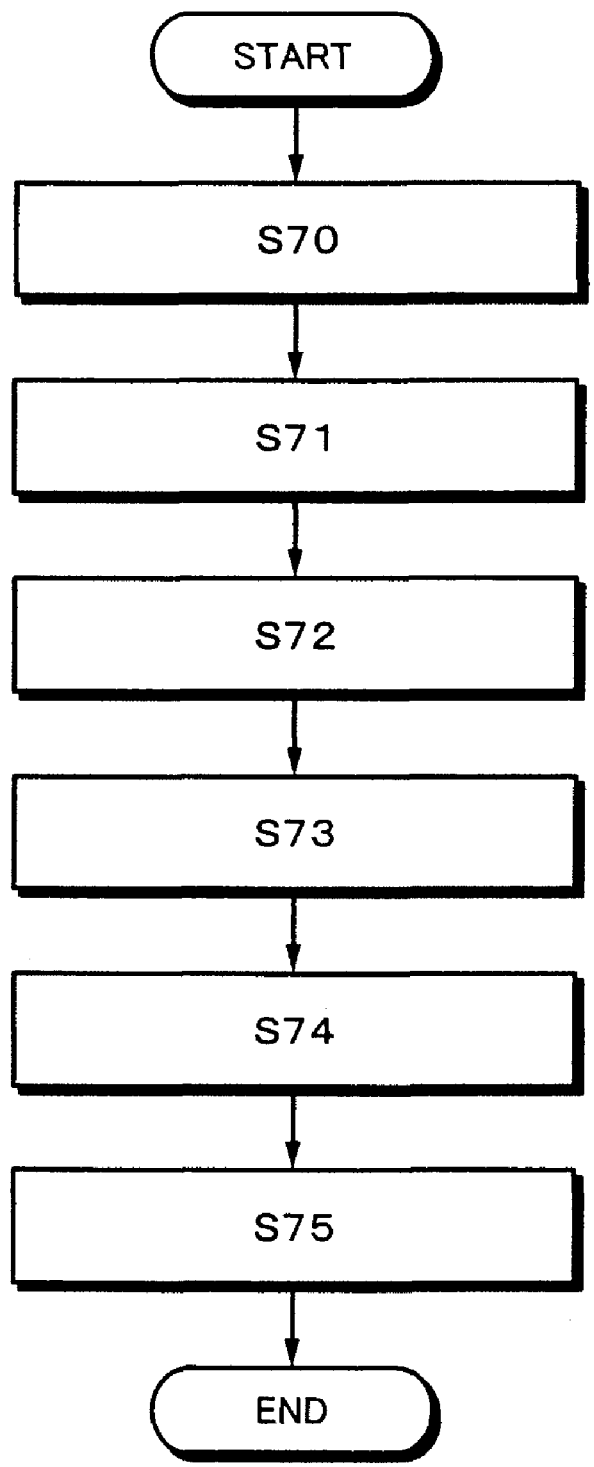
FIG. 20 is a flow chart showing an example of a process performed upon completion of reproduction.

FIG. 20 shows an example of a process preformed upon completion of the reproduction operation. While the movie player 300 is performing the reproduction operation for a disc, when the user causes the movie player 300 to stop the reproduction operation (at step S70), the movie player 300 performs this process. When the user's input 310 that causes the movie player 300 to stop the reproduction operation is input to the native implementation platform 301, it starts an exit process (at step S71). The exist process is composed of for example the following three steps:

(1) restrains new events from occurring,
(2) discards event handlers that have been queued, and
(3) issues control command uo_stop( ) to the movie player 300.

The native implementation platform 301 executes the exit process at step S71. After the native implementation platform 301 stops the execution of the current event handler (at step S72), the flow advances to step S73. At step S73, the native implementation platform 301 informs the script layer 302 of event exit. Accordingly, the script layer 302 executes onExit( ) (at step S74). Event handler onExit( ) executes for example a predetermined post process performed upon completion of the reproduction operation and method setUserData that stores user's setting data.

At step S75, the native implementation platform 301 performs the exit process. In the exit process, the native implementation platform 301 stores continuous information to for example a nonvolatile memory (namely, a backup of the state that exists immediately before the reproduction operation is completed to the resume information 324) and causes the system menu to appear on the screen.

The player model can reproduce video data, audio data, and subtitle data. Since events that the content creator intended occur at reproduction times that he or she intended and corresponding event handlers that he or she intended are executed, operations that he or she intended can be accomplished. In addition, when the user operates the UMD video player that is performing the reproduction operation for a disc, the native implementation platform 301 informs the movie player 300 of a command corresponding to the user's operation so that the state of the player is changed to the state that the user intended. In addition, the native implementation platform 301 informs the script layer 302 of an event corresponding to the user's input. As a result, the script layer 302 can accomplish the operations that the content creator intended corresponding to user's operations. When the player model has this structure, the user can interactively operate the video player to reproduce video data, audio data, and subtitle data.

5. Example of Script Program

Figure 21:
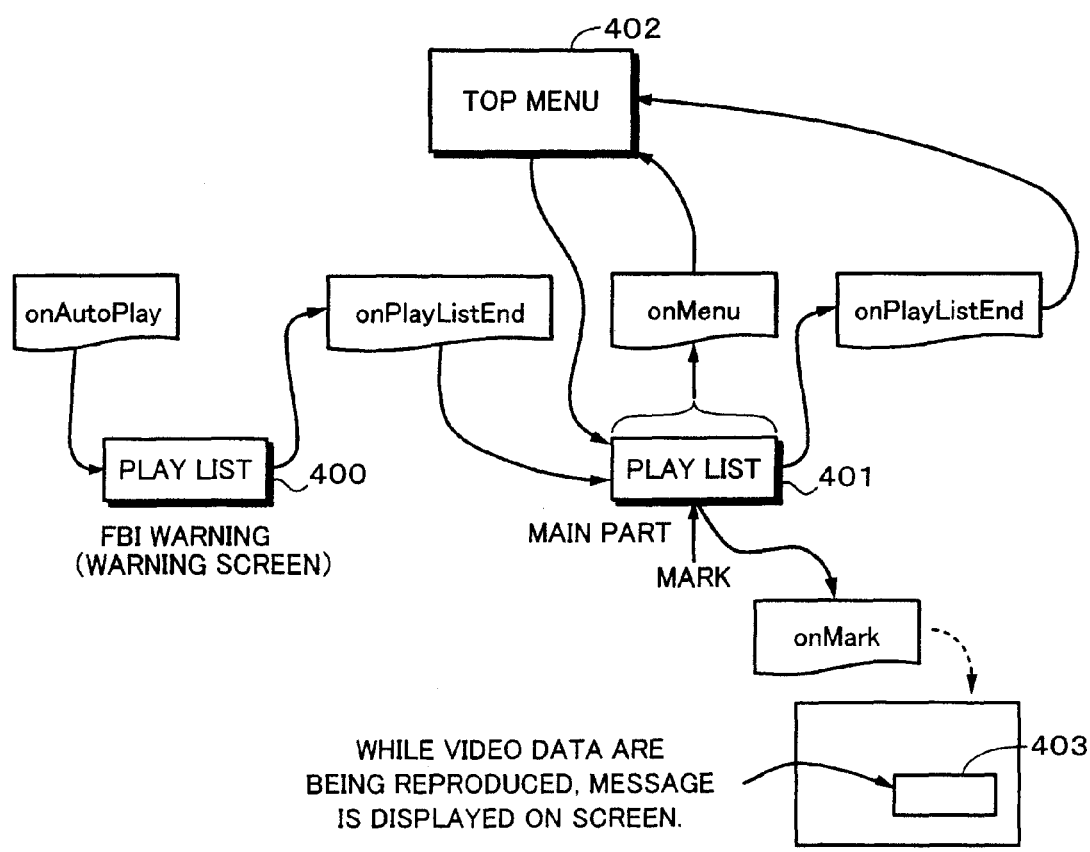
FIG. 21 is a schematic diagram describing an example of a script program.

Next, an example of a script program of the script layer 302 will be described. It is assumed that the content creator created a flow of content reproduction as shown in FIG. 21. The content shown in FIG. 21 has as display elements play lists 400 and 401, a top menu 402, and a message 403. The play list 400 is used to display a warning message that is automatically displayed when a disc is loaded. The play list 401 is a main part of a movie as an example of the content. The top menu 402 has GUI parts such as buttons with which the user causes the play list 401 to be reproduced. The message 403 is displayed at any reproduction time of the play list 401.

In addition, in the structure shown in FIG. 21, several event handlers are provided. When a disc is loaded into the UMD video player, event handler onAutoPlay( ) automatically reproduces the play list 400 from the disc and displays a warning message on the screen. Event handler onPlayListEnd( ) is an event handler that is called when the reproduction of the play list is completed. In the example shown in FIG. 21, when the reproduction of the play list 400 and the play list 401 is completed, event handler onPlayListEnd( ) is called. In other words, event handler onPlayListEnd( ) determines what play list's reproduction is completed. When the reproduction of the play list 400 is completed, event handler onPlayListEnd( ) starts the reproduction of the play list 401. When the reproduction of the play list 401 is completed, event handler onPlayListEnd calls the top menu 402.

Event handler onMenu( ) is called when the user operates the menu key. Event handler onMenu( ) calls the top menu 402 and displays it on the screen. Event handler onMark( ) is executed when a reproduction time designated by mark Mark elapsed. In the example shown in FIG. 21, mark Mark is set in the play list 401. When the play list 401 is reproduced and the reproduction time designated by mark Mark elapses, the message 403 is displayed on the screen.

In the example shown in FIG. 21, when the disc is loaded into the UMD video player, event handler onAutoPlay is called. Event handler onAutoPlay reproduces the play list 400 and displays a warning message. After the reproduction time of the play list 400 has elapsed, at the end of the play list 400, event handler onPlayListEnd is called. Event handler onPlayListEnd determines that the play list 400 has been completely reproduced and reproduces the next play list 401. When the user operates the menu key while the play list 401 is being reproduced, event handler onMenu is called. Event handler onMenu displays the top menu 402 on the screen. Event handler onMenu starts reproducing the play list 401 from the beginning corresponding to a predetermined operation on the top menu 402. When the reproduction time of the play list 401 has elapsed for the time designated by mark Mark, event handler onMark is called. Event handler onMark displays the message 403 on the screen. When the play list 401 has been completely reproduced, event handler onPlayListEnd is called. Event handler determines that the play list 401 has been completely reproduced and displays the top menu 402 on the screen.

FIG. 22 shows an example of a script program that accomplishes the operation shown in FIG. 21. As described above, the script program has event handlers and executes them upon occurrence of corresponding events. The script program is stored in file "SCRIPT.DAT" that will be described later.

Method "movieplayer.play( )" causes the movie player 300 to reproduce a play list. A play list number to be reproduced is described in parentheses ( ) as an argument. When the play list has been reproduced, event playListEnd occurs. When event playListEnd occurs, the script calls event handler movieplayer.onPlayListEnd( ). At this point, in addition to event playListEnd, object event_info is supplied to the script. The play list number of the play list that has been completely reproduced and so forth are stored in object event_info. The script can change the next operation corresponding to the content of object event_info.

6. File Management Structure

Figure 23:
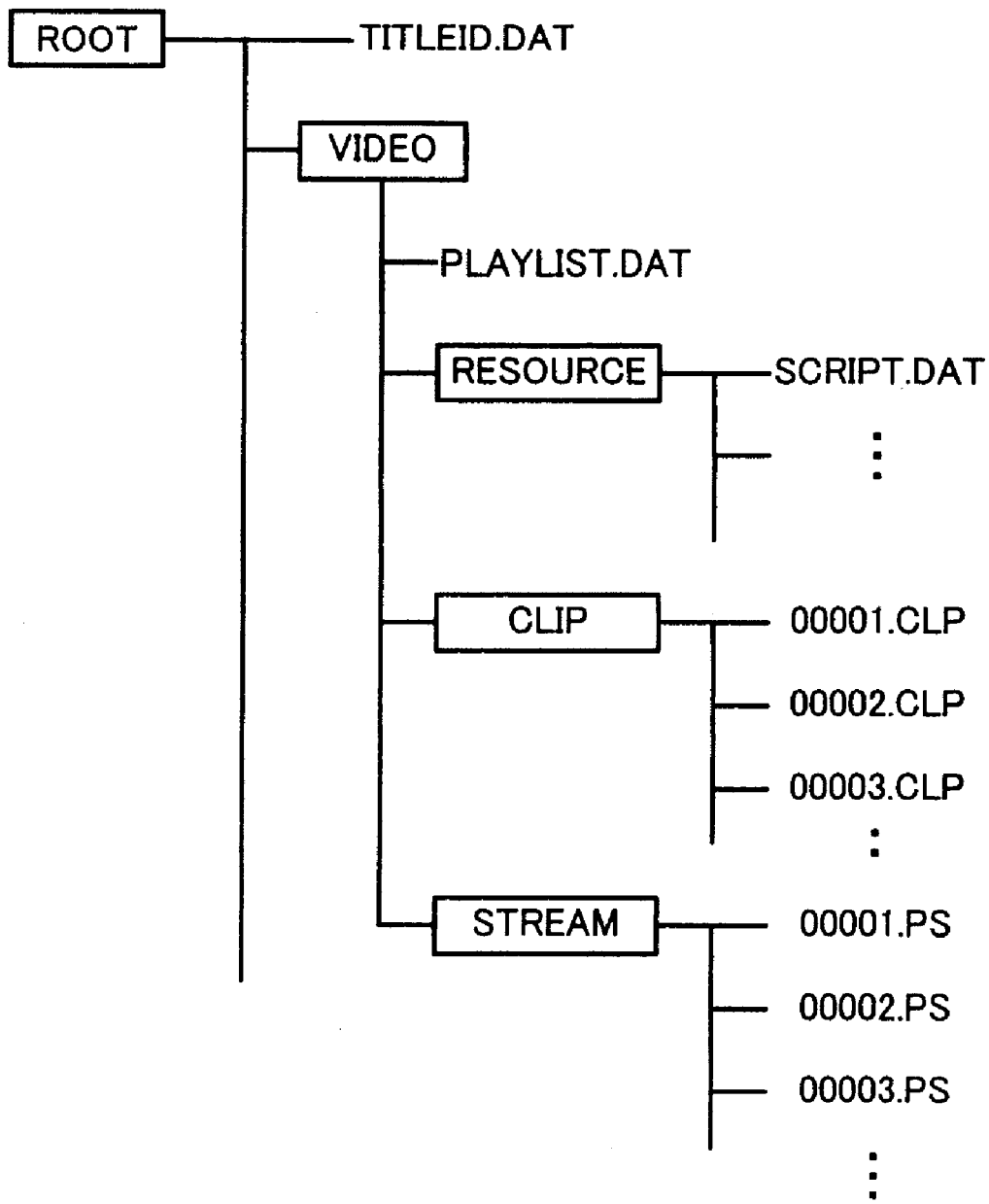
FIG. 23 is a schematic diagram describing a file management structure according to the UMD video standard.

Next, with reference to FIG. 23, the file management structure according to the UMD video standard will be described. Files are hierarchically managed in a directory structure and recorded on a disc. A disc file system standardized by International Organization for Standardization (ISO) 9660 or Universal Disk Format (UDF) may be used.

File "TITLEID.DAT" and directory "VIDEO" are placed under the root directory. Directory "RESOURCE," directory "CLIP," directory "STREAM," and file "PLAYLIST.DAT" are placed under directory "VIDEO."

File "TITLEID.DAT" is a file that stores a title identifier that differs in each title (type of content). One disk has one file "TITLEID.DAT."

File "SCRIPT.DAT" is placed under directory "RESOURCE." As described above, file "SCRIPT.DAT" stores a script program that composes the script layer 302. Normally, file "SCRIPT.DAT" as one file is placed under directory "RESOURCE." Instead, a plurality of files "SCRIPT.DAT" may be placed under directory "RESOURCE." In this case, parts of the file names are changed so that they become unique. A plurality of files "SCRIPT.DAT" are used for different display languages. In this case, however, one file "SCRIPT.DAT" is used at a time.

At least one clip information file is placed under directory "CLIP." A clip information file has a file name composed of a character string portion having several to five characters such as "00001" (in this example, numerals), a period as a delimiter, and an extension portion such as "CLP." Extension portion "CLP" represents that the file is a clip information file.

At least one clip AV stream file is placed under directory "STREAM." A clip AV stream file has a file name composed of a character string portion having several to five characters such as "00001" (in this example, numerals), a period as a delimiter, and an extension portion such as "PS." Extension portion "PS" represents that the file is a clip AV stream file. According to the embodiment of the present invention, a clip AV stream file is an MPEG2 (Moving Pictures Experts Group 2) program stream of which a video stream, an audio stream, and a subtitle stream are multiplexed and stored in a file identified by extension portion "PS."

As described above, a clip AV stream file is a file of which video data and audio data are compression-encoded and time-division multiplexed. Thus, when the clip AV stream file is read and decoded, video data and audio data are obtained. A clip information file is a file that describes the characteristics of a clip AV stream file. Thus, a clip information file and a clip AV stream file are correlated. According to the embodiment of the present invention, since the character string portions having several to five characters of the file names of the clip information file and the clip AV stream file are the same, the relationship therebetween can be easily obtained.

File "SCRIPT.DAT" is a script file that describes a script program. File "SCRIPT.DAT" stores a program that causes reproduction states for a disc to be interactively changed according to the embodiment of the present invention. File "SCRIPT.DAT" is read before other files are read from the disc.

File "PLAYLIST.DAT" is a play list file that describes a play list that designates the reproduction order of a clip AV stream. Next, with reference to FIG. 24 to FIG. 26, the internal structure of file "PLAYLIST.DAT" will be described. FIG. 24 shows an example of syntax that represents the entire structure of file "PLAYLIST.DAT." In this example, the syntax is described in the C language, which is used as a descriptive language for programs of computer devices. This applies to tables that represent other syntaxes.

Field name_length has a data length of 8 bits and represents the length of the name assigned to the play list file. Field name_string has a data length of 255 bytes and represents the name assigned to the play list file. In field name_string, the area from the beginning for the byte length represented by field name_length is used as a valid name. When the value of field "name_length" is "10," 10 bytes from the beginning of field name_string is interpreted as a valid name.

Field number_of_PlayList has a data length of 16 bits and represents the number of blocks PlayList( ) that follow. Field number_of_PlayLists is followed by a for loop. The for loop describes blocks PlayList( ) corresponding to field number_of_PlayLists. Block PlayList( ) is a play list itself.

Next, an example of the internal structure of block PlayList( ) will be described. Block PlayList( ) starts with field PlayList_data_length. Field PlayList_data_length has a data length of 32 bits and represents the data length of block PlayList( ), including field PlayList_data_length. Field PlayList_data_length is followed by field reserved_for_word_alignment having a data length of 15 bits and flag capture_enable_flag_PlayList having a data length of 1 bit. Field reserved_for_word_alignment and flag capture_enable_flag_PlayList having a data length of 1 bit align data at a 16-bit position in block PlayList( ).

Flag capture_enable_flag_PlayList is a flag that represents whether a moving picture that belongs to block PlayList( ) including flag capture_enable_flag_PlayList is permitted to be secondarily used. When the value of flag capture_enable_flag_PlayList is for example "1," it represents that the moving picture that belongs to PlayList( ) is permitted to be secondarily used in the player.

In the foregoing example, flag capture_enable_flag_PlayList has a data length of 1 bit. Instead, flag capture_enable_flag_PlayList may have a data length of a plurality of bits that describe a plurality of secondary use permission levels. For example, flag capture_enable_flag_PlayList may have a data length of 2 bits. In this case, when the value of the flag is "0," the movie picture may not be perfectly prohibited from being secondarily used. When the value of the flag is "1," the movie picture may be permitted to be secondarily used in the case that the movie picture is compression-encoded with a predetermined resolution or lower such as 64 pixels×64 lines. When the value of the flag is "2," the moving picture may be perfectly permitted to be secondarily used without any restriction. Instead, when the value of bit 0 of the flag is "0," the moving picture may be permitted to be secondarily used in the content reproduction application. When the value of bit 1 of the flag is "1," the moving picture may be permitted to be secondarily used in another application (for example, wall paper image or a screen saver) in the movie player. In this case, the values of bits 0 and 1 of the flag may be used in combination.

Field PlayList_name_length has a data length of 8 bits and represents the length of the name assigned to block PlayList( ). Field PlayList_name_string has a data length of 255 bits and represents the name assigned to block PlayList( ). In field PlayList_name_string, the area from the beginning for the byte length represented by field PlayList_name_string is used as a valid name.

Field number_of_PlayItems has a data length of 16 bits and represents the number of blocks PlayItem( ) that follow. Field number_of_PlayItems is followed by a for loop. The for loop describes blocks PlayItem( ) corresponding to field number_of_PlayItems. Block PlayItem( ) is a play item itself.

Blocks PlayItem( ) of block PlayList are assigned identification information (ID). For example, block PlayItem( ) described at the beginning of block PlayList( ) is assigned for example 0. Blocks PlayItem( ) are assigned serial numbers in the order of appearance such as 1, 2, and so forth. The serial numbers are used as identification information of blocks PlayItem( ). Argument i of the for loop repeated for blocks PlayItem( ) can be used as identification information for blocks PlayItem( ). Block PlayItem( ) is followed by block PlayListMark( ).

Next, with reference to FIG. 25, an example of the internal structure of block PlayItem( ) will be described. Block PlayItem( ) starts with field length. Field length has a data length of 16 bits and represents the length of block PlayItem( ). Field length is followed by field Clip_Information_file_name_length. Field Clip_Information_file_name_length has a data length of 16 bits and represents the length of the name of the clip information file corresponding to block PlayItem( ). Field Clip_Information_file_name has a variable data length in bytes and represents the name of the clip information file corresponding to block PlayItem( ). In field Clip_Information_file_name, the area from the beginning for the byte length represented by field Clip_Information_file_name is used as a valid name. When a clip information file is designated by field Clip_Information_file_name, a clip AV stream file corresponding to the clip information file can be identified according to the above-described relationship of the file names.

Field IN_time and field OUT_time have a data length of 32 bits each. Field IN_time and field OUT_time are time information that designate the reproduction start position and the reproduction end position of a clip AV stream file corresponding to the clip information file designated by field Clip_Information_file_name in block PlayItem( ). With field IN_time and field OUT_time, the reproduction start position other than the beginning of the clip AV stream file can be designated. Likewise, with field IN_time and field OUT_time, the reproduction end position other than the end of the clip AV stream file can be designated.

Next, with reference to FIG. 26, an example of the internal structure of block PlayListMark( ) will be described. Block PlayListMark( ) starts with field length. Field length has a data length of 32 bits and represents the length of block PlayListMark( ). Field length is followed by field number_of_ PlayList_marks. Field number_of_PlayList_marks has a data length of 16 bits and represents the number of blocks Mark( ). Field number_of_PlayList_marks is followed by a for loop. The for loop describes blocks Mark( ) corresponding to field number_of_PlayList_marks.

Next, an example of the internal structure of block Mark( ) will be described. Block Mark( ) starts with field mark_type. Field mark_type has a data length of 8 bits and represents the type of block Mark( ) including field mark_type. According to the embodiment, as shown in FIG. 27, three types of marks, a chapter mark, an index mark, and an event mark are defined. A chapter is a search unit that divides a play list (block PlayList( )). An index is a search unit that divides a chapter. A chapter mark and an index mark respectively represent a chapter position and an index position as time information. An event mark is a mark that cause an event to occur.

Field mark_name_length has a data length of 8 bits and represents the length of the name assigned to block Mark( ). Field mark_name_string at the last line of block Mark( ) represents the name assigned to block Mark( ). In field mark_name_string, the area from the beginning for the byte length represented by field mark_name_length is used as a valid name.

Four elements of field ref_to_PlayItem_id, field mark_time_stamp, field entry_ES_stream_id, and field entry_ES_private_stream_id correlate block Mark( ) defined in block PlayList( ) with a clip AV stream file. In other words, field ref_to_PlayItem_id has a data length of 16 bits and represents identification information of block PlayItem( ). Thus, field ref_to_PlayItem_id identifies a clip information file and a clip AV stream file.

Figure 28:
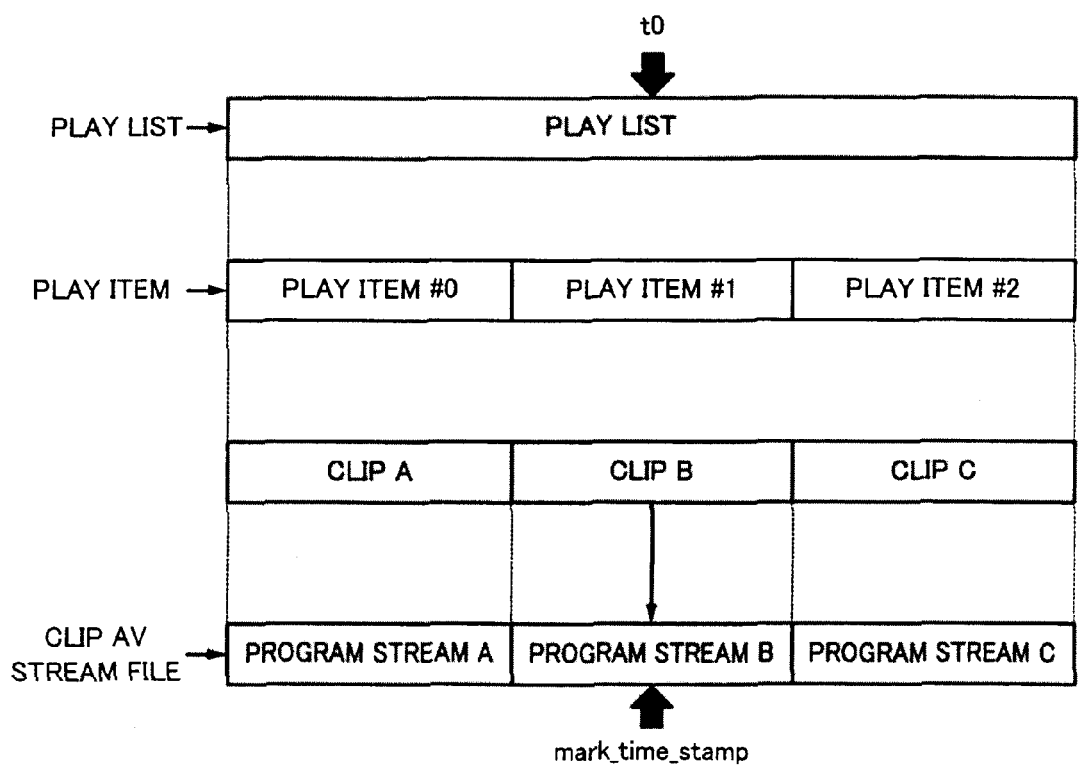
FIG. 28 is a schematic diagram describing designation of a mark time in a clip AV stream file.

Field mark_time_stamp has a data length of 32 bits and designates the time of a mark in a clip AV stream file. Next, with reference to FIG. 28, field mark_time_stamp will be described in brief. In FIG. 28, a play list is composed of three play items assigned 0, 1, and 2 (PlayItem(#0), PlayItem(#1), and PlayItem(#2)). Time $t_0$ of the play list is included in play item 1 (PlayItem(#1)). Play items 0, 1, and 2 correspond to program streams A, B, and C of clip AV stream files through clip information files, respectively.

In this case, when a mark is designated to time $t_0$ of the play list, the value of field ref_to_PlayItem_id is "1" that represents play item 1 including time $t_0$. In addition, time corresponding to time $t_0$ in the corresponding clip AV stream file is described in field mark_time_stamp.

Returning to the description of FIG. 26, field mark_time_stamp is followed by field entry_ES_stream_id and field entry_ES_private_stream_id. Field entry_ES_stream_id and field entry_ES_private_stream_id have a data length of 8 bits each. When block Mark( ) is correlated with a predetermined elementary stream, field entry_ES_stream_id and field entry_ES_private_stream_id identify the elementary stream. Field entry_ES_stream_id and field entry_ES_private_stream_ id represent a stream ID (stream_id) of packets (packet( )) in which elementary streams are multiplexed and a private stream ID (private_stream_id) of a private packet header (private_packet_header( )), respectively.

The stream ID (stream_id) of the packets (packet( )) and the private stream ID (private_stream_id) of the private packet header (private_packet_header( )) are based on provisions on a program stream of the MPEG2 system.

Field entry_ES_stream_id and field entry_ES_private_stream_id are used when the chapter structure of clip AV stream #0 is different from that of clip AV stream #1. When block Mark( ) is not correlated with a predetermined elementary stream, the values of these two fields are "0."

Next, with reference to FIG. 29 to FIG. 33, the internal structure of a clip information file will be described. As described above, clip information file "XXXXX.CLP" describes the characteristics and so forth of corresponding clip AV stream file "XXXXX.PS" placed under directory "STREAM."

FIG. 29 shows an example of syntax that represents the entire structure of clip AV stream file "XXXXX.CLP." Clip AV stream file "XXXXX.CLP" starts with field presentation_start_time and field presentation_end_time. Field presentation_start_time and field presentation_end_time have a data length of 32 bits each and represent the times of the beginning and end of the corresponding clip AV stream file. As time information, the presentation time stamp (PTS) of the MPEG2 system may be used. PTS has an accuracy of 90 kHz.

Field presentation_start_time and field presentation_end_time are followed by field reserved_for_word_alignment that has a data length of 7 bits and flag capture_enable_flag_ Clip that has a data length of 1 bits. Field reserved_for_word_alignment and flag capture_enable_flag_Clip having a data length of 1 bit align data at a 16-bit position in file "XXXXX.CLP." Flag capture_enable_flag_Clip is a flag that represents whether a moving picture contained in a clip AV stream file corresponding to file "XXXXX.CLP" is permitted to be secondarily used. For example, when the value of flag capture_enable_flag_Clip is for example "1," it represents that the moving picture of the clip AV stream file corresponding to file "XXXXX.CLP" is permitted to be secondarily used in the video player.

Field number_of_streams has a data length of 8 bits and represents the number of blocks StreamInfo( ) that follow. Field number_of_streams is followed by a for loop. The for loop describes blocks StreamInfo( ) corresponding to field number_of_streams. The for loop is followed by block EP_map( ).

Next, an example of the internal structure of block StreamInfo( ) will be described. Block StreamInfo( ) starts with field length. Field length has a data length of 16 bits and represents the length of block StreamInfo( ). Field length is followed by field stream_id and field private_stream that have a data length of 8 bits each. As shown in FIG. 30, block StreamInfo( ) is correlated with elementary streams. In the example shown in FIG. 30, when the value of field stream_id of block StreamInfo( ) is in the range from "0xE0" to "0xEF," block StreamInfo( ) is correlated with a video stream. When the value of field stream_id of block StreamInfo( ) is "0xBD," block StreamInfo( ) is correlated with an Adaptive Transform Acoustic Coding (ATRAC) audio stream, a Linear Pulse Code Modulation (LPCM) audio stream, or a subtitle stream.

When the value of field private_stream_id of block StreamInfo( ) is in the range from "0x00" to "0x0F," from "0x10" to "0x1F," and from "0x80" to "0x9F," block StreamInfo( ) is correlated with an ATRAC audio stream, an LPCM audio stream, and a subtitle stream, respectively.

In FIG. 30, "0x" represents hexadecimal notation. This notation applies to the following description.

Block StreamInfo( ) mainly describes two types of information, the first type not varying in a stream, the second type varying in a stream. Information that does not vary in a stream is described in block StaticInfo( ), whereas information that varies in a stream is described in block DynamicInfo( ) with change points designated with time information.

Block StaticInfo( ) is followed by field reserved_for_word_alignment that has a data length of 8 bits. Field reserved_for_word_alignment aligns data in a byte in block StreamInfo( ). Field reserved_for_word_alignment is followed by field number_of_DynamicInfo. Field number_of_DynamicInfo has a data length of 8 bits and represents the number of blocks DynamicInfo( ) that follow. Field number_of_DynamicInfo is followed by a for loop. The for loop describes fields pts_change_point and blocks DynamicInfo( ) corresponding to field number_of_DynamicInfo.

Field pts_change_point has a data length of 32 bits and represents a time at which information of block DynamicInfo( ) becomes valid with PTS. A time at which each stream starts is represented by field pts_change_point and equal to field presentation_start_time defined in file "XXXXX.CLP."

Next, with reference to FIG. 31, an example of the internal structure of block StaticInfo( ) will be described. The content of block StaticInfo( ) depends on the type of the corresponding elementary stream. The type of the corresponding elementary stream can be identified by the values of field stream_id and field private_stream_id as shown in FIG. 30. FIG. 31 shows block StaticInfo( ) whose content varies depending on the type of an elementary stream, which is a video stream, an audio stream, or a subtitle using an if statement. Next, block StaticInfo( ) will be described according to the types of elementary streams.

When the elementary stream is a video stream, block StaticInfo( ) is composed of field picture_size, field frame_rate, and flag cc_flag. Field picture_size and field frame_rate each have a data length of 4 bits each. Flag cc_flag has a data length of 1 bit. Field picture_size and field frame_rate represent the picture size and the frame frequency of the video stream. Flag cc_flag represents whether the video stream contains a closed caption. When the value of flag cc_flag is for example "1," the video stream contains a closed caption. Field reserved_for_word_alignment aligns data in 16 bits.

When the elementary stream is an audio stream, block StaticInfo( ) is composed of field audio_language_code having a data length of 16 bits, field channel_configuration having a data length of 8 bits, flag lfe_existance having a data length of 1 bit, and field sampling_frequency having a data length of 4 bits. Field audio_language_code represents a language code contained in the audio stream. Field channel_configuration represents a channel attribute of audio data such as monaural, stereo, multi-channel, or the like. Field lfe_existance represents whether the audio stream contains a low frequency emphasis channel. When the value of field lfe_existance is for example "1," the audio stream contains the low frequency emphasis channel. Field sampling_frequency represents the sampling frequency of audio data. Field reserved_for_word_alignment is aligned at a 16-bit position.

When the elementary stream is a subtitle stream, block StaticInfo( ) is composed of field subtitle_language_code having a data length of 16 bits and flag configurable_flag having a data length of 1 bit. Field subtitle_language_code represents a language code contained in the subtitle stream. Field subtitle_language_code represents whether the subtitle stream is a normal subtitle or a subtitle for commentary (for example, special subtitle for description of pictures). Flag configurable_flag represents whether the size and position of characters of the subtitle stream that is displayed are permitted to be changed. When the value of flag configurable_flag is for example "1," it represents that the size and position of characters of the subtitle stream that is displayed are permitted to be changed. Field reserved_for_word_alignment is aligned at a 16-bit position.

Next, with reference to FIG. 32, an example of the internal structure of block DynamicInfo( ) will be described. Block DynamicInfo( ) starts with field reserved_for_word_alignment having a data length of 8 bits. Elements preceded by field reserved_for_word_alignment depend on the type of the elementary stream. The type of the elementary stream can be identified by field stream_id and field private_stream_id described in FIG. 30. In FIG. 32, block DynamicInfo( ) whose content varies depending on the type of an elementary stream, which is a video stream, an audio stream, or a subtitle using an if statement. Next, block DynamicInfo( ) will be described according to the type of elementary streams.

When the elementary stream is a video stream, block DynamicInfo( ) is composed of field display_aspect_ratio having a data length of 4 bits. Field display_aspect_ratio represents whether the display output aspect ratio of video data is 16:9 or 4:3. Field reserved_for_word_alignment aligns data in 16 bits.

When the elementary stream is an audio stream, block DynamicInfo( ) is composed of field channel_assignment having a data length of 4 bits. When the audio stream is composed of two channels, field channel_assignment represents whether the output is a stereo or a dual monaural. The dual monaural is used to reproduce audio data for example in two languages. Field reserved_for_word_alignment aligns data in 16 bits.

When the elementary stream is a subtitle stream, block DynamicInfo( ) is composed of field reserved_for_word_alignment. Field reserved_for_word_alignment aligns data in 16 bits. In other words, with respect to a subtitle stream, block DynamicInfo( ) does not define an attribute that dynamically varies.

Next, with reference to FIG. 33, an example of the internal structure of block EP_map( ) will be described. Block EP_map( ) represents a valid decode start position (entry point) of a bit stream of each elementary stream with time information and position information. The position information may be the minimum access unit for a recording medium on which an elementary stream is recorded. Each elementary stream can be decoded from the position represented by block EP_map( ).

Since the valid decode start position of a fixed rate stream can be calculated, information such as block EP_map( ) is not necessary. On the other hand, for a variable rate stream and a stream whose data size varies in each access unit such as a stream according to the MPEG video compression-encoding system, block EP_map( ) is information necessary for randomly accessing data.

Block EP_map( ) starts with field reserved_for_word_alignment having a data length of 8 bits. Field reserved_for_word_alignment aligns data in 16 bits. Field reserved_for_word_alignment is followed by field number_of_stream_id_entries. Field number_of_stream_id_entries has a data length of 8 bits and represents the number of elementary streams described in block EP_map( ). A first for loop describes fields stream_id, fields private_stream_id, and fields number_of_EP_entries corresponding to field number_of_stream_id_entries. In the first for loop, a second for loop describes fields PTS_EP_start and fields RPN_EP_start corresponding to field number_of_EP_entries.

The first for loop describes field stream_id and field private_stream_id that have a data length of 8 bits each and identify the type of the elementary stream as shown in FIG. 30. Field stream_id and field private_stream_id are followed by field number_of_EP_entries. Field number_of_EP_entries has a data length of 32 bits and represents the number of entry points described in the elementary stream. The second for loop describes fields PTS_EP_start and fields RPN_EP_start corresponding to field number_of_EP_entries.

Field PTS_EP_start and field RPN_EP_start have a data length of 32 bits each and represent entry points themselves. Field PTS_EP_start represents a time of an entry point in a clip AV stream file with PTS. On the other hand, field RPN_EP_start represents the position of an entry point in a clip AV stream file in the unit of 2048 bytes.

According to the embodiment, one sector as a disc access unit is 2048 bytes. Thus, field RPN_EP_start represents the position of an entry point of a clip AV stream file in sectors.

The valid reproduction start position of a video stream needs to be immediately preceded by packet private_stream_2. Packet private_stream_2 is a packet that stores information that can be used to decode a video stream. Thus, the position of an entry point of a video stream is the position of pack pack( ) that stores packet private_stream_2.

Block EP_map correlates times of a clip AV stream and positions of a clip AV stream file. Thus, with time information (time stamp) of an access point of a clip AV stream, the clip AV stream file can be easily searched for a data address at which data are read. As a result, the disc can be smoothly randomly accessed.

According to the embodiment, in block EP_map( ), sets of time information and position information (sets of field PTS_EP_start and field RPN_EP_start in the second for loop) for each elementary stream are pre-registered in the ascending order (descending order). In other words, time information and position information have been rearranged in a predetermined direction. Thus, a binary search can be performed for the data.

According to the embodiment of the present invention, as described above, an elementary stream of a video stream is an elementary stream on the basis of the MPEG2-Video standard. However, the present invention is not limited to this example. For example, an elementary stream of a video stream may be an elementary stream according to the MPEG4-Visual standard or MPEG4-AVC standard. Likewise, according to the embodiment, as described above, an elementary stream of an audio stream is an elementary stream on the basis of the ATRAC audio system. However, the present invention is not limited to such an example. Instead, an elementary stream of an audio stream may be an elementary stream on the basis of for example MPEG1/2/4 audio system.

7. Disc Reproducing Apparatus

Figure 34:
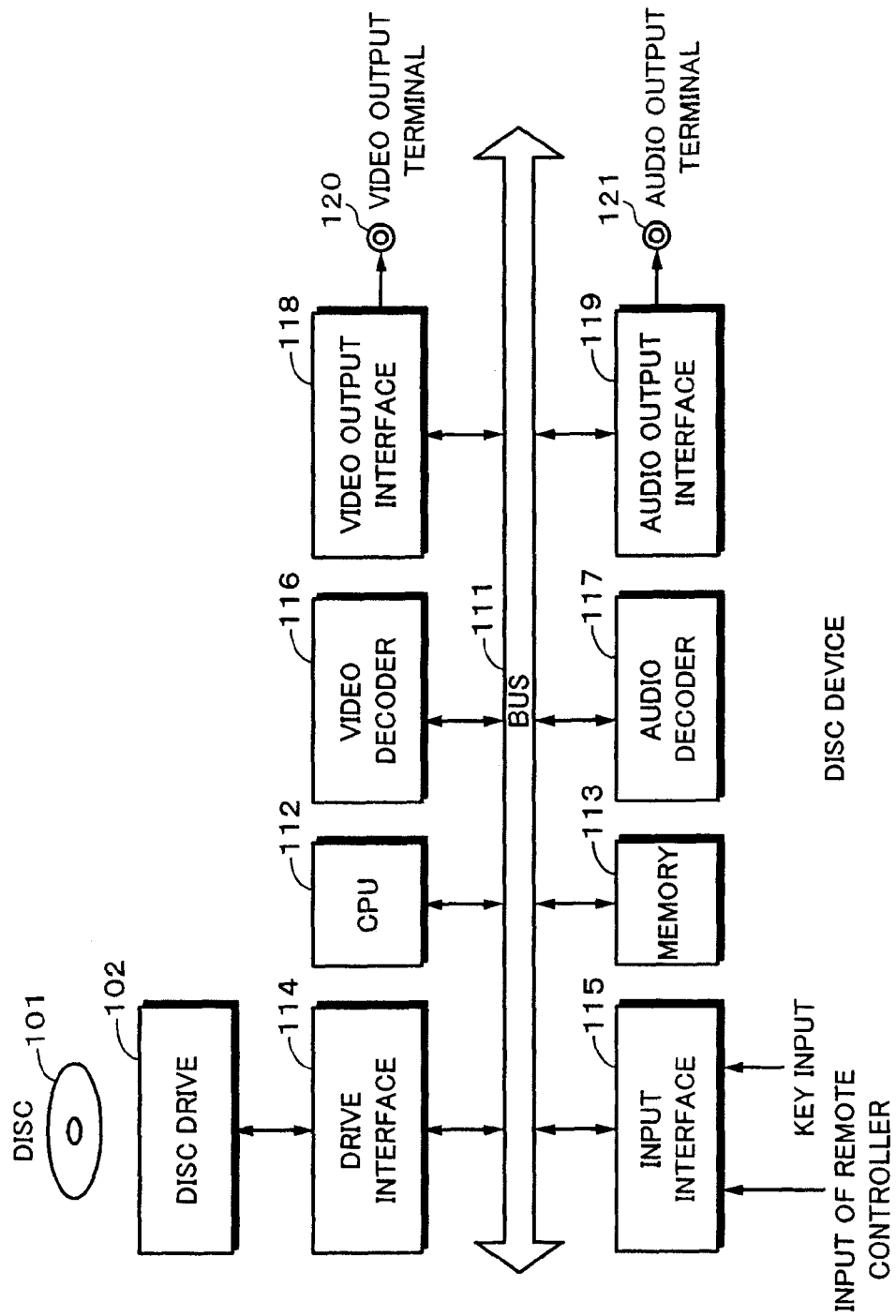
FIG. 34 is a block diagram showing an example of the structure of a disc reproducing apparatus according to the present invention.

Next, a disc reproducing apparatus according to an embodiment of the present invention will be described. FIG. 34 shows an example of the structure of a disc reproducing apparatus 100 according to the present invention. Connected to a bus 111 are a central processing unit (CPU) 112, a memory 113, a drive interface 114, an input interface 115, a video decoder 116, an audio decoder 117, a video output interface 118, and an audio output interface 119. Each section of the disc reproducing apparatus 100 can exchange a video stream, an audio stream, various commands, data, and so forth with other sections through the bus 111.

In addition, a disc drive 102 is connected to the drive interface 114. The disc drive 102 exchanges data and commands with the bus 111 through the drive interface 114.

The CPU 112 has a read-only memory (ROM) and a random access memory (RAM) (not shown). The CPU 112 exchanges data and command with each section of the disc reproducing apparatus 100 through the bus 111 according to a program and data pre-stored in the ROM and controls the entire disc reproducing apparatus 100. The RAM is used as a work memory of the CPU 112.

Supplied to the input interface 115 is an input signal that is input from an input device with which the user performs an input operation. The input device is for example a remote control commander with which the user remotely operates the disc reproducing apparatus 100 using for example an infrared signal and keys disposed on the disc reproducing apparatus 100. The input interface 115 converts an input signal supplied from the input device into a control signal for the CPU 112 and outputs the control signal.

Recorded on a disc 101 in the format shown in FIG. 23 to FIG. 33 are a play list, a script program, a clip information file, a clip AV stream file, and so forth. When the disc 101 is loaded into the disc drive 102, it reproduce data from the disc 101 automatically or according to a user's input operation. A script file, a play list file, and a clip information file that are read from the disc 101 are supplied to the CPU 112 and stored in for example a RAM of the CPU 112. The CPU 112 reads a clip AV stream file from the disc 101 according to data and a script program stored in the RAM.

The clip AV stream file that is read from the disc 101 is temporarily stored in the memory 113. The video decoder 116 decodes a video stream and a subtitle stream of the clip AV stream file stored in the memory 113 according to a command received from the CPU 112. The CPU 112 performs an image process such as an enlargement process or a reduction process for the decoded video data and subtitle data, a synthesization process or an addition process for the video stream and subtitle stream, and obtains one stream of video data. The image process may be performed by the video decoder 116 and the video output interface 118. The video data are buffered by the memory 113 and supplied to the video output interface 118. The video output interface 118 converts the supplied video data into an analog video signal and supplies the analog video signal to a video output terminal 120.

Likewise, the audio decoder 117 decodes an audio stream of the clip AV stream file stored in the memory 113 according to a command received from the CPU 112. The decoded audio data are buffered in the memory 113 and supplied to the audio output interface 119. The audio output interface 119 converts the supplied audio data into for example an analog audio signal and supplies the analog audio signal to an audio output terminal 121.

In the example, each section shown in FIG. 34 is composed of independent hardware. However, the present invention is not limited to this example. For example, the video decoder 116 and/or the audio decoder 117 may be composed of software that operates on the CPU 112.

Figure 35B:
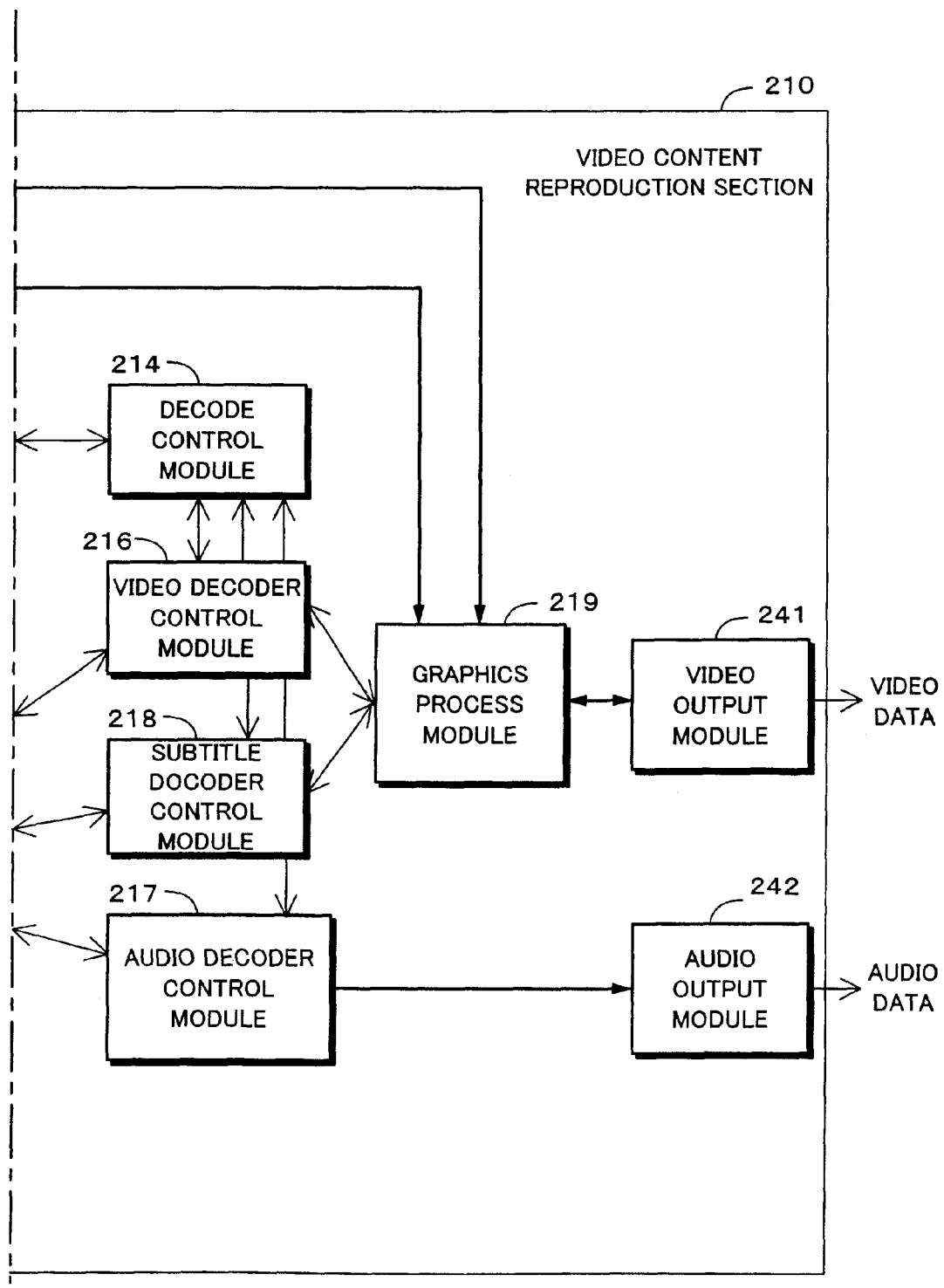

FIG. 35A and FIG. 35B are functional block diagrams describing the operation of the disc reproducing apparatus 100 shown in FIG. 34 in detail. The disc reproducing apparatus 100 is mainly composed of an operation system 201 and a video content reproduction section 210. The video content reproduction section 210 is substantially a software program that operates on the operation system 201. Instead, the video content reproduction section 210 may be composed of software and hardware that integrally operate. In the following description, it is assumed that the video content reproduction section 210 is composed of software. In FIG. 35A and FIG. 35B, the disc drive 102 is omitted.

When the power of the disc reproducing apparatus 100 is turned on, the operation system 201 initially starts up on the CPU 112 and performs necessary processes such as initial settings for each section, and reads an application program (in this example, the video content reproduction section 210) from the ROM. The operation system 201 provides basic services such as reading of a file from the disc 101 and interpreting of a file system for the video content reproduction section 210 while the video content reproduction section 210 is operating. For example, the operation system 201 controls the disc drive 102 through the drive interface 114 corresponding to a file read request supplied from the video content reproduction section 210 and reads data from the disc 101. The data that are read from the disc 101 are supplied to the video content reproduction section 210 under the control of the operation system 201.

The operation system 201 has a multitask process function that controls a plurality of software modules virtually in parallel by for example time-division control. In other words, each module that composes the video content reproduction section 210 shown in FIG. 35A and FIG. 35B can be operated in parallel by the multitask process function of the operation system 201.

Next, the operation of the video content reproduction section 210 will be described more specifically. The video content reproduction section 210 has more internal modules and accomplishes the following functions.

(1) The video content reproduction section 210 determines whether the loaded disc 101 is a disc according to the UMD video standard (hereinafter this disc is referred to as the UMD video disc).

(2) When the determined result represents that the loaded disc 101 is the UMD video disc, the video content reproduction section 210 reads a script file from the disc 101 and supplies the script file to a script control module 211.

(3) When the determined result represents that the loaded disc 101 is the UMD video disc, the video content reproduction section 210 also reads files that composes a database (namely, a play list file, a clip information file, and so forth) and supplies the files to a player control module 212.

Next, the operations of the modules of the video content reproduction section 210 will be described.

The script control module 211 interprets a script program described in script file "SCRIPT.DAT" and executes it. As described in the player model, GUIs that create and output images of the menu screen, move the cursor corresponding to a user's input, and change the menu screen are accomplished by a graphics process module 219 controlled according to the script program. By executing the script program, the script control module 211 can control the player control module 212.

The player control module 212 references database information stored in files such as play list file "PLAYLIST.DAT" and clip information file "XXXXX.CLP" that are read from the disc 101 and performs the following controls to reproduce video contents recorded on the disc 101.

(1) The player control module 212 analyzes database information such as a play list and clip information.

(2) The player control module 212 controls a content data supply module 213, a decode control module 214, and a buffer control module 215.

(3) The player control module 212 performs player state change controls such as reproduction, reproduction stop, and reproduction pause and a reproduction control process such as stream change according to a command received from the script control module 211 or the input interface 115.

(4) The player control module 212 obtains time information of a video stream that is being reproduced from the decode control module 214, displays time, and generates a mark event.

The content data supply module 213 reads content data such as a clip AV stream file from the disc 101 according to a command received from the player control module 212 and supplies the content data to the buffer control module 215. The buffer control module 215 stores the content data in the memory 113 as a substance 215A of the buffer. The content data supply module 213 controls the buffer control module 215 to supply the content data stored in the memory 113 to a video decoder control module 216, an audio decoder control module 217, and a subtitle decoder control module 218 according to requests therefrom. In addition, the content data supply module 213 reads content data from the disc 101 so that the amount of content data stored under the control of the buffer control module 215 becomes a predetermined amount.

The decode control module 214 controls the operations of the video decoder control module 216, the audio decoder control module 217, and the subtitle decoder control module 218 according to a command received from the player control module 212. The decode control module 214 has an internal clock function and controls the operations of the video decoder control module 216, the audio decoder control module 217, and the subtitle decoder control module 218 so that video data and audio data are synchronously output.

The buffer control module 215 exclusively uses a part of the memory 113 as the substance 215A of the buffer. The buffer control module 215 stores a data start pointer and a data write pointer. The buffer control module 215 also has as internal modules a video read function, an audio read function, and a subtitle read function. The video read function has a video read pointer. The video read function has a register that stores information au_information( ) as access unit information. The audio read function has an audio read pointer. The subtitle read function has a subtitle read pointer and a subtitle read function flag. The subtitle read function flag controls enabling/disabling of the subtitle read function according to a write value. When for example "1" is written to the subtitle read function flag, the subtitle read function becomes enabled. When for example "0" is written to the subtitle read function flag, the subtitle read function becomes disabled.

The video read function, the audio read function, and the subtitle read function, which are internal modules of the buffer control module 215, have demultiplexer functions that demultiplex a multiplexed clip AV stream, of which a video stream, an audio stream, and a subtitle stream have been multiplexed, into these streams. According to the embodiment of the present invention, a plurality of elementary streams are multiplexed according to time-division multiplying system and MPEG2 system program stream format and thereby a clip AV stream is formed. Thus, the video read function, the audio read function, and the subtitle read function have demultiplexer functions for the MPEG2 system program streams.

Consequently, the video read function reads the value of field stream_id (see FIG. 30) placed at a predetermined position of the video stream and holds the value. Likewise, the audio read function and the subtitle read function read the values of field stream_id and field private_stream_id (see FIG. 30) and hold the values. The values of field stream_id and field private_stream_id are used to analyze the supplied bit stream.

The video decoder control module 216 causes the video read function of the buffer control module 215 to read one video access unit of the video stream from the memory 113 and supply the video access unit to the video decoder 116. The video decoder control module 216 controls the video decoder 116 to decode the video stream supplied to the video decoder 116 in the access unit and generate video data. The video data are supplied to the graphics process module 219.

Likewise, the audio decoder control module 217 causes the audio read function of the buffer control module 215 to read one audio access unit of the audio stream from the memory 113 and supply the audio stream unit to the audio decoder 117. According to the embodiment of the present invention, the access unit (audio frame) that composes an audio stream has a predetermined fixed length. The audio decoder control module 217 controls the audio decoder 117 to decode the audio stream supplied to the audio decoder 117 in the access unit and generate audio data. The audio data are supplied to an audio output module 242.

The subtitle decoder control module 218 causes the subtitle read function of the buffer control module 215 to read one subtitle access unit of the subtitle stream from the memory 113 and supply the subtitle access unit to the subtitle decoder control module 218. According to the embodiment of the present invention, the subtitle access unit that composes the subtitle stream contains length information at the beginning. The subtitle decoder control module 218 has a subtitle decode function that can decode the supplied subtitle stream and generate subtitle image data. The subtitle image data are supplied to the graphics process module 219.

As described above, the video data decoded by the video decoder 116 under the control of the video decoder control module 216 and the subtitle image data decoded by the subtitle decoder control module 218 are supplied to the graphics process module 219. The graphics process module 219 adds the subtitle image data to the supplied video data and generates a video signal that is output. The graphics process module 219 generates the menu image and the message image corresponding to a command received from the script control module 211 and the player control module 212 and overlays them with the output video signal.

For example, the graphics process module 219 performs an enlargement process and a reduction process for the supplied subtitle image data and adds the processed image data to the video data according to a command received from the script control module 211.

In addition, the graphics process module 219 converts the aspect ratio of the output signal according to the aspect ratio of the predetermined output video device and the output aspect ratio designated in the content reproduced from the disc 101. When the aspect ratio of the output video device is 16:9 and the output aspect ratio is 16:9, the graphics process module 219 directly outputs the video data. When the output aspect ratio is 4:3, the graphics process module 219 performs a squeezing process that matches the height of the image with the height of the screen of the output video device, inserts black portions into left and right sides of the image, and outputs the resultant image. When the aspect ratio of the output video device is 4:3 and the output aspect ratio is 4:3, the graphics process module 219 directly outputs the video data. When the output aspect ratio is 16:9, the graphics process module 219 performs a squeezing process that matches the width of the image with the width of the screen of the output video device, inserts black portions into the upper and lower portions of the image, and outputs the resultant image.

The graphics process module 219 also performs a process that captures the video signal that is being processed according to a request from the player control module 212 and supplies the requested video signal thereto.

A video output module 241 exclusively uses a part of the memory 113 as a first-in first-out (FIFO) buffer. The video output module 241 temporarily stores video data processed by the graphics process module 219 in the buffer and reads the video data therefrom at predetermined timing. The video data that are read from the buffer are output from the video output interface 118.

The audio output module 242 exclusively uses a part of the memory 113 as a FIFO buffer. The audio output module 242 stores audio data that are output from the audio output interface 119 to the buffer and reads the audio data therefrom at predetermined timing. The audio data that are read from the buffer are output from the audio output interface 119.

When the audio mode of the content is dual monaural (for example, bilingual), the audio output module 242 outputs the audio data according to a predetermined audio output mode. When the audio output mode is "main audio," the audio output module 242 copies audio data of the left channel in for example the memory 113 and outputs audio data of the left channel and audio data from the memory 113. Thus, the audio output module 242 outputs audio data of only the left channel. When the audio output mode is "sub audio," the audio output module 242 copies audio data of the right channel in for example the memory 113 and outputs audio data of the right channel and audio data from the memory 113. Thus, the audio output module 242 outputs audio data of only the right channel. When the audio output mode is "main and sub audio" or the content is stereo, the audio output module 242 directly outputs the audio data.

The user can interactively sets the audio output mode on for example the menu screen that the video content reproduction section 210 generates.

A nonvolatile memory control module 250 writes data to an area whose data are not erased after the operation of the video content reproduction section 210 is completed (this area is referred to as a nonvolatile area) and reads data therefrom according to a command received from the player control module 212. The nonvolatile memory control module 250 has a function that stores a plurality of sets of data Saved_Player_Status and data Saved_Player_Data with a key of a title ID (Title_ID). The nonvolatile memory control module 250 stores as data Saved_Player_Status data Backup_Player_Status that the player control module 212 has. Data Backup_Player_Status corresponds to data of for example the player status 323B that exist immediately before the operation of the player control module 212 is completed. Data Saved_Player_Status corresponds to the resume information 324. In addition, the nonvolatile memory control module 250 stores as data Saved_User_Data data User_Data that the player control module 212 has. Data User_Data are predetermined data that the user sets to the player control module 212.

When the disc reproducing apparatus 100 has a flash memory or the like, which is a nonvolatile memory, the nonvolatile memory control module 250 correlatively stores a set of data Saved_Player_Status and data Saved_User_Data with the title ID of the disc 101 in a predetermined region of the flash memory. The storage medium that the nonvolatile memory control module 250 stores data is not limited to a flash memory, but a hard disk or the like.

8. Automatic Selection of Audio and Subtitle Streams

Next, automatic selection of audio and subtitle streams according to an embodiment of the present invention will be described. According to this embodiment, when a plurality of audio streams of different languages and a plurality of subtitle streams of differ languages have been multiplexed, an audio stream of a proper language is automatically selected. Likewise, a subtitle stream of a proper language is automatically selected.

According to the present invention, in addition to the regular audio language setting using language names such as "Japanese" and "English", a status "original language" can be set. When the audio language setting of the player has been "original language", an audio stream of a proper language is automatically selected. In addition, when subtitle and audio streams are automatically selected, the case of which the languages of audio and subtitle streams are the same is prevented.

The "original language" represents a language in which content was created. For example, if content was created in Japan and the language thereof is mainly Japanese, the original language is Japanese. The original language can be set on the content creator side.

Figure 36:
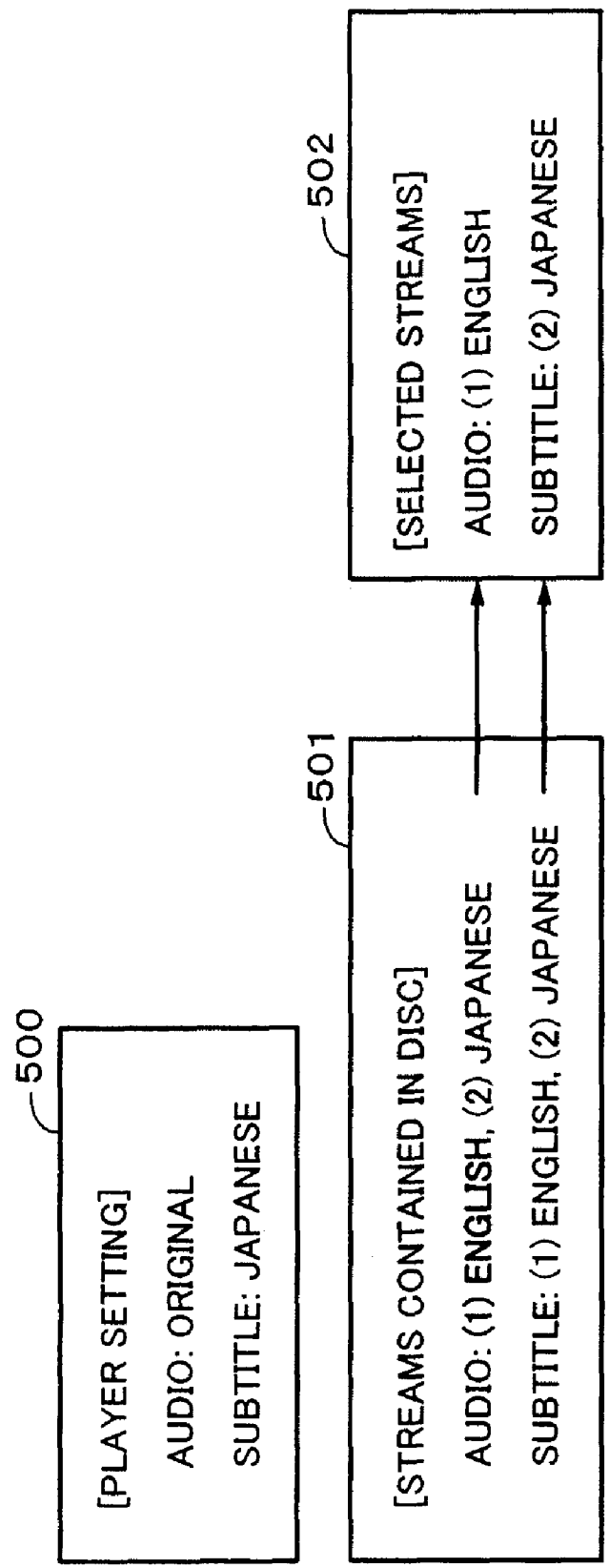
FIG. 36 is a schematic diagram describing automatic selection of audio and subtitle stream according to an embodiment of the present invention.
Figure 37:
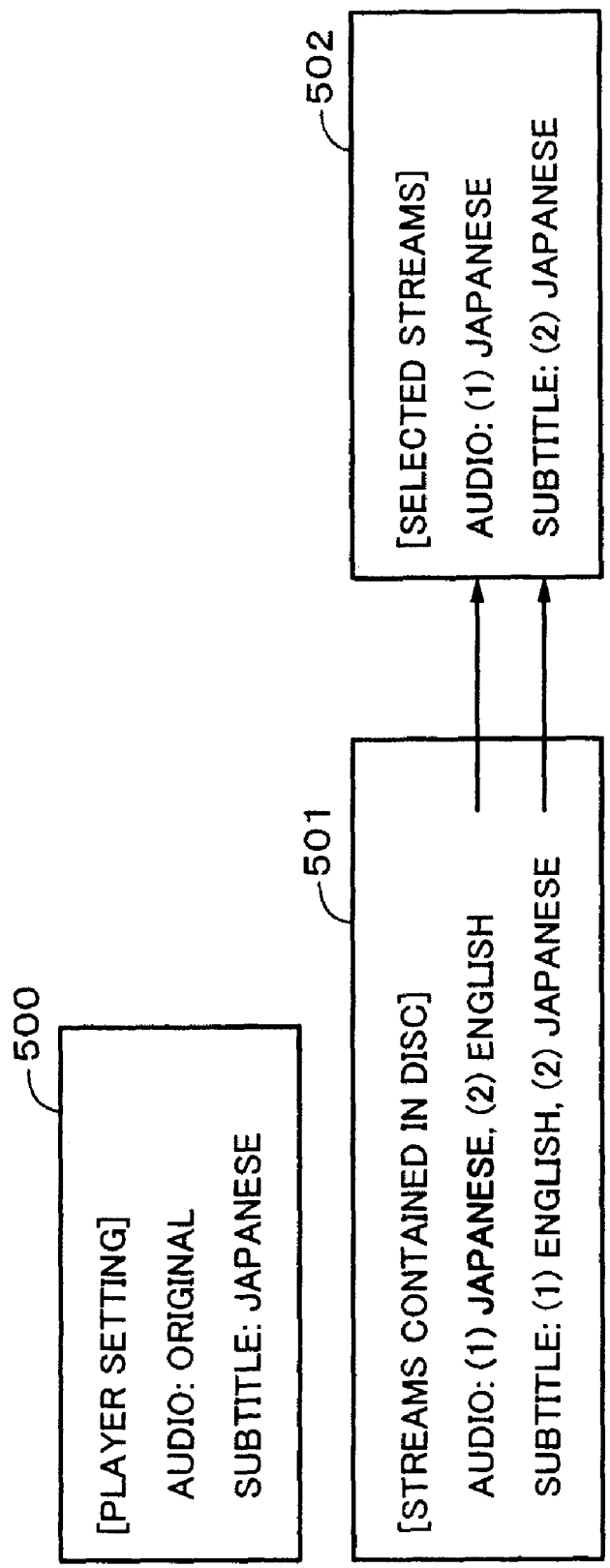
FIG. 37 is a schematic diagram describing the automatic selection of audio and subtitle streams according to the embodiment of the present invention.
Figure 38:
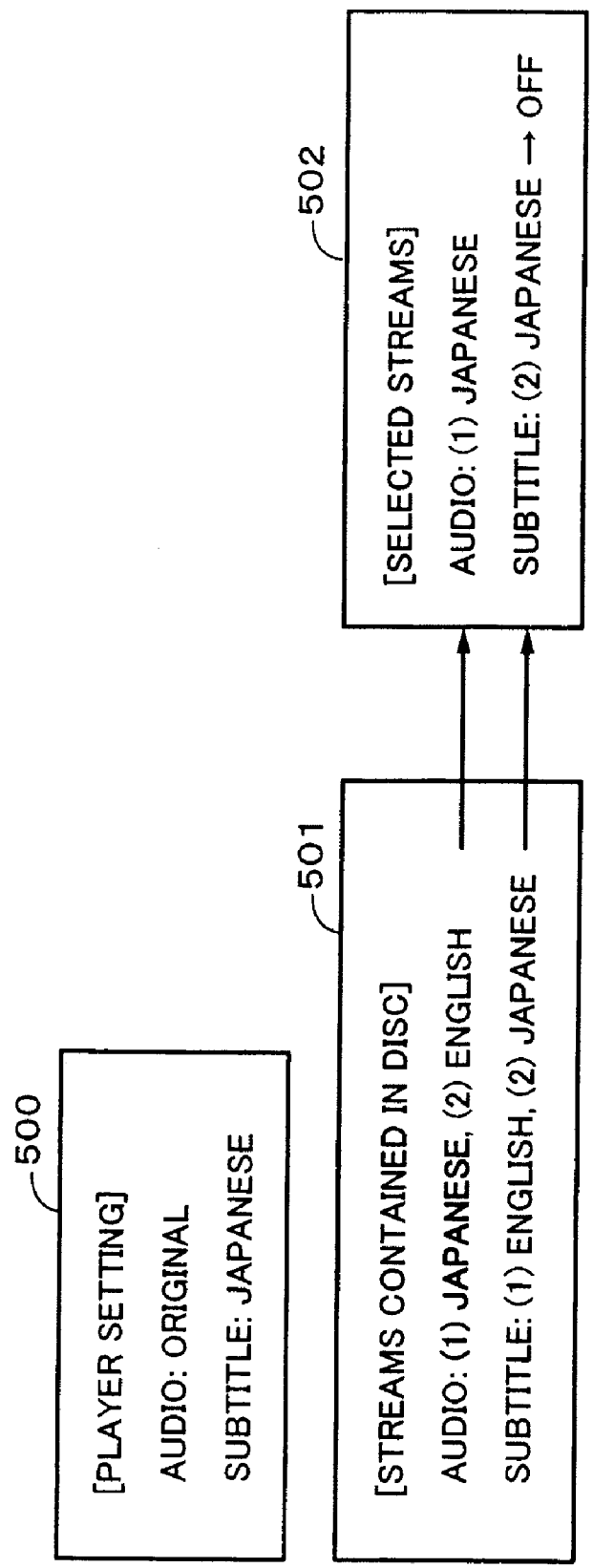
FIG. 38 is a schematic diagram describing the automatic selection of audio and subtitle streams according to the embodiment of the present invention.

Next, with reference to FIG. 36 to FIG. 38, automatic selection of audio and subtitle streams according to this embodiment of the present invention will be described in brief. In FIG. 36 to FIG. 38, it is assumed that in streams 501 contained in a disc, an audio stream denoted by (1) is the original language. In this example, the original language of a subtitle is not defined.

As a first example, with reference to FIG. 36, the case of which in player setting 500, the language of audio is set to "original language" and the language of a subtitle is set to "Japanese" will be considered. In addition, it is assumed that content contained in a disc is a movie created in the United States and the streams 501 of the disc are two types of audio streams (1) English (=original language) and (2) Japanese and two types of subtitle streams (1) English and (2) Japanese. In this case, streams 502 selected immediately after content is reproduced from the disc by the player are an audio stream of the original language (1) English and a subtitle stream of (2) Japanese. In the example shown in FIG. 36, since an audio stream and a subtitle stream are properly selected, no problem occurs.

As a second example, as shown in FIG. 37, in the player setting 500, the language of audio is set to "original language" and the language of a subtitle is set to "Japanese" that are the same as those of the first example. In addition, it is assumed that content recorded on a disc is a movie created in Japan and the streams 501 of the disc are two types of audio streams (1) Japanese (=original language) and (2) English and two types of subtitle streams (1) English and (2) Japanese. In this case, streams selected immediately after content is reproduced from the disc by the player are an audio stream as the original language (1) Japanese and a subtitle stream (2) Japanese. Thus, the same language is selected. In this case, since the subtitle of Japanese is not necessary, it is thought that this selection is not user-friendly.

To solve the problem of the second example, as shown in FIG. 38, when the language of audio has been set to "original language" in the player setting 500 and when the original language matches the language of the subtitle, as with the selected streams 502, it is sufficient to accomplish a function of turning off the display of the subtitle.

In other words, when the language of the audio of the player setting 500 has been set to "original language" and the language of audio matches the language of the subtitle as the result of the automatic selection, property subtitleFlag contained in attribute information (player status 323B of property 323, see FIG. 3) of the player, which causes a subtitle to be displayed or not displayed, is set to a value that represents subtitle OFF. With this rule, when the languages of audio and a subtitle are selected, a subtitle stream whose language is the same as that of audio can be prevented from being output.

Next, the automatic selection of audio and subtitle streams according to an embodiment of the present invention will be described in detail. First of all, information with which the player apparatus side needs to be provided to properly and automatically select audio and a subtitle will be described. The property 323 (see FIG. 3) of the movie player 300, which controls reproduction of a stream, has been described with reference to FIG. 7. In the property 323, property audioLanguegeCode, property audioNumber, and property audioFlag for audio and property subtitleLanguegeCode, property subtitleNumber, and property subtitleFlag for subtitles in particular relate to this embodiment.

As described above, property audioLanguageCode represents a language code of an audio language that has been set in the UMD video player. In other words, property audioLanguegeCode represents a language to be selected for audio. As a value of property audioLanguegeCode, a language code defined for example in the International Organization for Standardization (ISO) 639-1 may be used. In ISO 639-1, for example English is abbreviated as "en" and Japanese as "jp". According to this embodiment, as a value of property audioLanguegeCode, "00", which is not defined in ISO 639-1, is added. With value "00", "original language" is represented.

As described above, property audioNumber represents the stream number of an audio stream that is being currently reproduced. Property audioNumber is a 16-bit value composed of an audio stream ID (stream_id) and a private stream ID (private_stream_id) (see FIG. 30). Of 16 bits, high order eight bits are used for a stream ID, whereas the low order eight bits are used for a private stream ID. An audio stream of a clip AV stream file can be uniquely identified by this 16-bit value.

Property audioFlag represents reproduction information of an audio stream. FIG. 39 shows examples of values that property audioFlag can have. When the value of property audioFlag is "0", the reproduction of audio is turned off, causing audio not to be reproduced. When the value is "1", an audio stream represented by property audioNumber is reproduced. At this point, taking account of the case of which an audio stream represented by property audioNumber is dual mono, namely contents of left and right channels of stereo are different, when the value is "2", only left channel of dual mono is reproduced, whereas when the value is "3", only right channel of dual mono is reproduced. When an audio stream is dual mono and the value of property audioFlag is "1", both left and right channels of dual mono are reproduced.

Property subtitleLanguageCode represents a language code of the language of a subtitle that has been set to the UMD video player. In other words, property subtitleLanuegeCode represents a language to be selected for a subtitle. As a value of property subtitleLanguegeCode, the language code defined for example in the International Organization for Standardization (ISO) 639-1 can be used like that for audio streams.

As described above, property subtitleNumber represents the number of a subtitle stream that is currently being reproduced. A value of property subtitleNumber is a 16-bit value composed of a stream ID (stream_id) of a subtitle stream and a private stream ID (private_stream_id) (see FIG. 30). Of 16 bits, high order eight bits are used as a stream ID, whereas the low order eight bits are used for a private stream ID. A subtitle stream of a clip AV stream can be uniquely identified by this 16-bit value.

Property subtitleFlag represents a reproduction status of a subtitle stream. FIG. 40 shows examples of values of property subtitleFlag. When the value of property subtitleFlag is "0", the subtitle display is turned off, causing a subtitle not be displayed. When the value is "1", the subtitle display is turned on, causing a subtitle to be displayed.

Next, information with which the content side needs to be provided to properly and automatically select audio and a subtitle will be described. The content side describes attribute information of audio streams and attribute information of subtitle streams in a clip information file. As described with reference to FIG. 29 and FIG. 31, the clip information file contains information of field stream_id and field private_stream_id that uniquely identify each elementary stream multiplexed in a corresponding AV stream and attribute information shown in FIG. 31. Of attribute information shown in FIG. 31, field audio_language_code for an audio stream and field subtitle_language_code for a subtitle stream in particular relate to this embodiment of the present invention.

Audio streams of a plurality of languages can be multiplexed into a clip AV stream file. Thus, it is necessary to indicate which of audio streams of a plurality of languages that have been multiplexed is an audio streams of the original language. According to this embodiment, in a clip information file shown in FIG. 29, a language of an audio stream that comes first in audio streams arranged by a for loop is defined as the original language. A language code of the original language is represented by field audio_language_code (see FIG. 31) corresponding to the audio stream.

The property 323 (player status 323B) of the movie player 300 can be set with methods described with reference to FIG. 8 on the script layer 302. Audio streams and subtitle streams are set with method play( ), method playChapter( ), and method changeStream( ). Of these methods, method changeStream( ) is a method of changing a current stream to a desired stream, not a mechanism of automatically selecting a stream. Thus, details of method changeStream( ) will be omitted. Method playChapter( ) is equivalent to what argument playListTime, which is one of arguments of method play( ), is substituted with argument chapterNumber, only method( ) will be described in the following.

FIG. 41A and FIG. 41B list examples of arguments of method play( ). When these arguments are given to method play( ) in a predetermined manner, reproduction of a video stream, an audio stream, and a subtitle stream corresponding to a stream number designated can be started. Syntax of method( ) is represented for example by formula (1). In other words, arguments are delimited by delimiters (in this example, commands ",") and arranged in a predetermined order. When arguments are omitted, only delimiters are described.

movieplayer.play(playListNumber,playListTime,
    menuMode,pauseMode,video_strm,audio_strm,
    audio_status,subtitle_strm,subtitle_status)     (1)

Argument playListNumber represents a play list number of a play list to be reproduced. Argument playListTime represents a time from the beginning of a play list. When content is reproduced from the beginning of a play list, the value of argument playListTime is set to "0". The value of argument menuMode is either "true" or "false". When the value of argument menuMode is "true", it denotes that content is reproduced in the menu mode. When the value of argument menuMode is "true", it denotes that content is reproduced in the normal mode. The value of argument pauseMode is "true" or "false". When the value of argument pauseMode is "true", it represents standby as pause. When the value of argument pauseMode is "false", it denotes that reproduction is started at normal speed. Argument video_strm represents a video stream to be reproduced. The value of argument video_strm is "−1" or "−2". When the value of argument video_strm is "−1", it denotes that a video stream to be reproduced is automatically selected by the movie player 300. When the value of argument video_strm is "−2", it denotes that a video stream to be reproduced is not changed.

The rest of arguments, including argument audio_strm, are arguments for reproduction of audio streams and subtitle streams. These arguments in particular relate to this embodiment of the present invention. Argument audio_strm is an argument with which a value is set to property audioNumber (see FIG. 7) of the movie player 300. Argument audio_strm is used to set an audio stream number represented by 16 bits of a stream ID (stream_id) and a private stream ID (private_stream_id) to property audioNumber. The value of argument audio_strm is "−1" or "−2". When the value of argument audio_strm is "−1", it denotes that a proper audio stream is automatically selected in the movie player 300 and the audio stream number of the selected audio stream is set to property audioNumber. When the value of argument audio_stream is "−2", it denotes that reproduction is started with the value of property audioNumber that is currently set, not changed.

Argument audio_status is a parameter with which property audioFlag (see FIG. 7) of the movie player 300 is set. When the value of argument audio_status is "0", "1", "2", or "3", the value is directly set to property audioFlag. When the value of argument audio_status is "−2", it denotes that the current value of property audioFlag is kept.

Argument subtitle_strm is an argument with which a value is set to property subtitleNumber (see FIG. 7) of the movie player 300. Argument subtitle_strm is used to set a subtitle stream number represented by 16 bits of a stream ID (stream_id) and a private stream ID (private_stream_id) to property subtitleNumber. The value of argument subtitle_strm is "−1" or "−2". When the value of argument subtitle_strm is "−1", it denotes that a proper subtitle stream is automatically selected in the movie player 300 and the subtitle stream number of the selected subtitle stream is set to property subtitleNumber. When the value of argument subtitle_strm is "−2", it denotes that reproduction is started with the value of property subTitleNumber that is currently set, not changed.

Argument subtitle_status is a parameter with which property subtitleFlag (see FIG. 7) of the movie player 300 is set. When the value of argument subtitle_status is non or "1", the value of argument subtitle_status is directly set to property subtitleFlag. When the value of argument subtitle_status is "−1", the value of property subtitleFlag is automatically set to a proper value in the movie player 300. When the value of argument subtitle_status is "−2", the current value of property subtitleFlag is kept.

Property audioFlag does not contain automatic setting of the movie player 300, whereas property subtitleFlag contains automatic setting of the movie player 300. This is because when audio and a subtitle are set to the same language, the display of the subtitle is automatically turned off, causing the subtitle not to be displayed.

Figure 42:
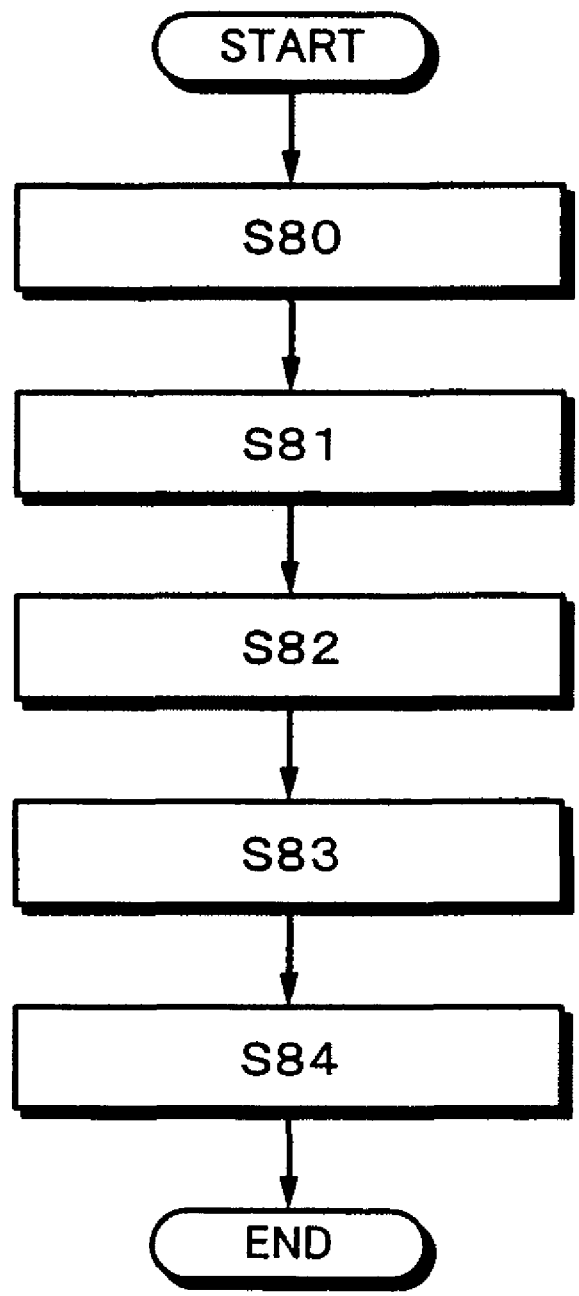
FIG. 42 is a flow chart showing a flow of a process of automatically selecting audio stream and subtitle stream from a plurality of types of audio streams and subtitle streams.

Next, the automatic selection process of an audio stream and a sub title stream will be described more specifically. FIG. 42 shows a flow of a process of automatically selecting an audio stream and a subtitle stream from a plurality of types of audio streams and subtitle streams. When a disc is loaded into the player apparatus, the user selects a video stream to be reproduced (at step S80). An audio stream corresponding to the selected video stream is automatically selected at step S81. Corresponding to the selected result, properly audioFlag is set at step S82. With reference to property audioFlag, a subtitle stream is selected at step S83. Corresponding to the selected result, property subtitle Flag is set at step S84.

Next, an example of the process of automatically selecting an audio stream at step S81 shown in FIG. 42 will be described in detail with reference to a flow chart shown in FIG. 43 and FIG. 44. In the automatic selection process of an audio stream, (1) language code, (2) the number of channels, and (3) arrangement of audio streams in clip information file are used. Of these attribute information, the priority of (1) language code is the highest, the priority of (2) the number of channels is the second highest, and the priority of (3) the arrangement of audio streams in clip information file is the lowest.

Figure 43:
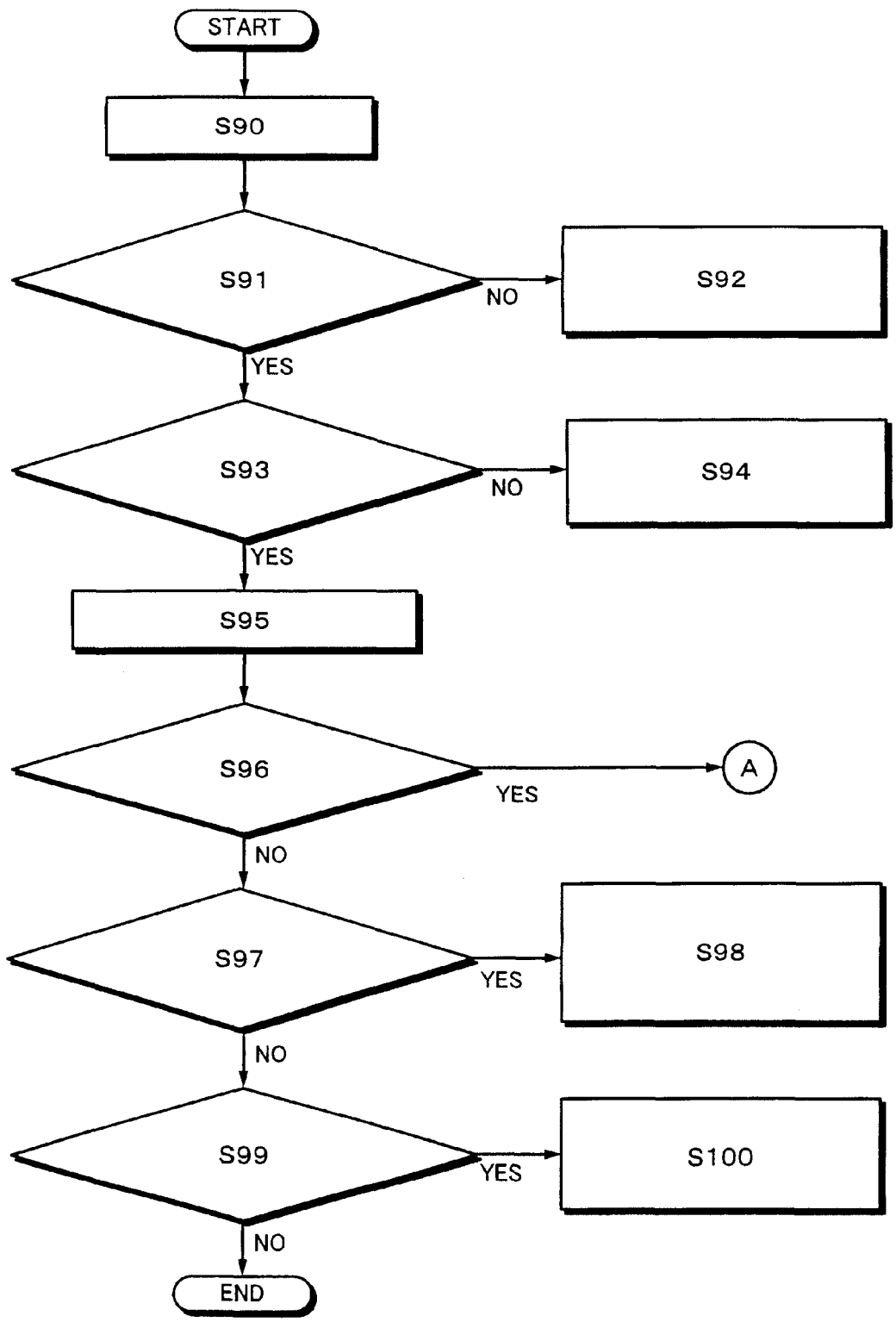
FIG. 43 is a flow chart describing in detail an example of a process of automatically selecting an audio stream.
Figure 44:
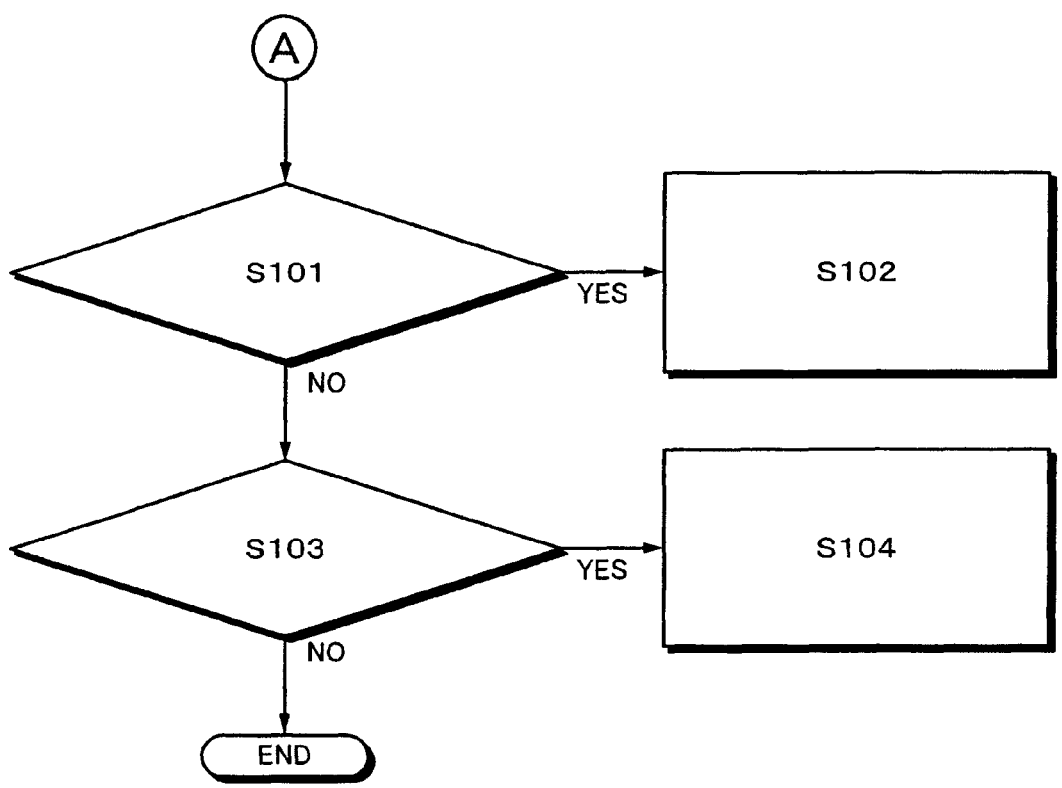
FIG. 44 is a flow chart describing in detail an example of a process of automatically selecting an audio stream.

In FIG. 43 and FIG. 44, reference letter A denotes that the flow advances to a portion represented by the same letter A.

When the selection process of an audio stream is started (at step S90), it is determined whether or not the value of argument audio_strm, which represents the stream number of an audio stream reproduced in method play( ), has been set to "−1" or the value has been omitted (at step S91). As described above, when the value of argument audio_strm is "−1", the automatic selection of an audio stream is designated.

When the determined result denotes that other than value "−1" has been set to argument audio_strm, the flow advances to step S92. At step S92, the value of argument audio_strm is set to property audioNumber. An audio stream represented by argument audio_strm is selected. Thereafter, the flow advances to step S82 shown in FIG. 42. At step S82, property audioFlag is set in the predetermined manner corresponding to the selected audio stream in the movie player 300. When the number of audio channels of the selected audio stream is 5.1 channels, the value of property audioFlag is set to for example "1", denoting whether or not to reproduce the audio stream. When an audio stream has not been selected at step S92, the process is terminated as an error.

When the process has been terminated as an error, the operation that the UMD video player performs depends on its implementation. When the process has been terminated as an error, the next process is performed with property audioNumber kept. This error process applies to other error processes in FIG. 43 and FIG. 44.

When the determined result at step S91 denotes that the value of argument audio_strm has been set to "−1" or omitted, the flow advances to step S93. At step S93, it is determined whether there is no audio stream identified by property audioNumber of the movie player 300 or the value of property audioNumber is undefined. When there is an audio stream identified by property audioNumber, the flow advances to step S94. At step S94, an audio stream identified by property audioNumber is selected. Thereafter, the flow advances to step S82 shown in FIG. 42. Property audiFlag is set in the predetermined manner corresponding to the selected audio stream in the movie player 300. When an audio stream has not been selected, the process is terminated as an error.

When the determined result at step S93 denotes that there is no audio stream identified by property audioNumber of the movie player 300 or the value of property audioNumber is undefined, the flow advances to step S95. After step S95, the automatic selection process for an audio stream is specifically performed. The automatic selection process of an audio stream at step S81 shown in FIG. 42 represents the entire process of the flow chart shown in FIG. 43. The process after step S95 of the flow chart shown in FIG. 43 is the automatic selection process of an audio stream executed when the value of argument audio_strm is "1", which represents the automatic selection.

First of all, the automatic selection process based on (1) language code is performed. This process is performed so that an audio stream whose language is the same as the audio language setting of the player is selected by priority. At step S96, it is determined whether or not the value of property audioLanguageCode in the movie player 300 is "00", which represents "original language". When the determined result denotes that the value of property audioLanguageCode represents "original language", the flow advances to step S101.

In steps from S101 to S104, it is determined what is "original language" that has been set on the content side. At step S101, the arrangement of audio streams in block StreamInfo( ) of the clip information file (see FIG. 29) is checked and a language code of a audio stream that comes first in the arrangement is obtained. Thereafter, it is determined whether or not there is an audio stream whose language code is the same as the obtained language code and whose number of audio channels is equal to or smaller than the number of audio channels that has been set to the UMD video player. When the determined result denotes that there is such an audio stream, the flow advances to step S102. When the determined result denotes that there is not such an audio stream, the flow advances to step S103.

At step S102, an audio stream whose number of audio channels is maximum in these audio streams that satisfy the conditions at step S101 is selected. When the audio channel setting of the UMD video player is for example 5.1 channels and there are two audio streams whose language code is the same as that of an audio stream that comes first in block StreamInfo( ) and whose numbers of audio channels are 2 channels and 5.1 channels, the audio stream whose number of channels is 5.1 channels is selected. When there are a plurality of audio streams whose number of audio channels is the same, an audio stream which comes earlier in block StreamInfo( ) is selected. Thereafter, the flow advances to step S82 shown in FIG. 42. At step S82, property audioFlag is set in the predetermined manner corresponding to the selected audio stream in the movie player 300.

At step S103, it is determined whether or not there is an audio stream whose number of audio channels is equal to or smaller than the number of audio channels that has been set to the UMD video player. When there is such an audio stream, an audio stream whose number of audio channels is maximum in these audio streams is selected (at step S104). When there are a plurality of audio streams whose number of audio channels is the same, an audio stream that comes earlier in block StreamInfo( ) is selected. Thereafter, the flow advances to step S82 shown in FIG. 42. Property audioFlag is set in the predetermined manner corresponding to the selected audio stream in the movie player 300.

When the determined result at step S103 denotes that there is not such an audio stream, the process according to the flow chart shown in FIGS. 43 and 44 is completed. In this case, although an audio stream has not been selected, the flow advances to step S82. At step S82, property audioFlag is set in the predetermined manner.

When the determined result at step S96 shown in FIG. 43 denotes that the value of property audioLanguegeCode of the movie player 300 does not represent "original language", the flow advances to step S97. At step S97, it is determined whether or not there is an audio stream whose language code is the same as that of property audioLanguegeCode of the movie player 300 and whose number of audio channels is the equal to or smaller than the number of audio channels that has been set to the UMD video player. When the determined result denotes that there is such an audio stream, the flow advances to step S98. When the determined result denotes that there is not such an audio stream, the flow advances to step S99.

At step S98, like step S102, an audio stream whose number of audio channels is maximum in audio streams that satisfy the conditions at step S97 is selected. When there are a plurality of audio streams whose number of audio channels is the same, an audio stream that comes earlier in block StreamInfo( ) is selected. Thereafter, the flow advances to step S82 shown in FIG. 42. Property audioFlag is set in the predetermined manner corresponding to the selected audio stream in the movie player 300.

At step S99, like step S103, it is determined whether or not there is an audio stream whose number of audio channels is equal to or smaller than the number of audio channels that has been set to the UMD video player. When the determined result denotes that there is such an audio stream, an audio stream whose number of audio channels is maximum in these audio streams is selected (at step S100). When there are a plurality of audio streams whose number of audio channels is the same, an audio stream that comes earlier in block StreamInfo( ) is selected. Thereafter, the flow advances to step S82 shown in FIG. 42. Property audioFlag is set in the predetermined manner corresponding to the selected audio stream in the movie player 300.

When the determined result at step S99 denotes that there is not such an audio stream, the process according to the flow chart shown in FIG. 43 and FIG. 44 is completed. In this case, although an audio stream has not been selected, the flow advances to step S82. At step S82, property audioFlag is set in the predetermined manner.

Figure 45:
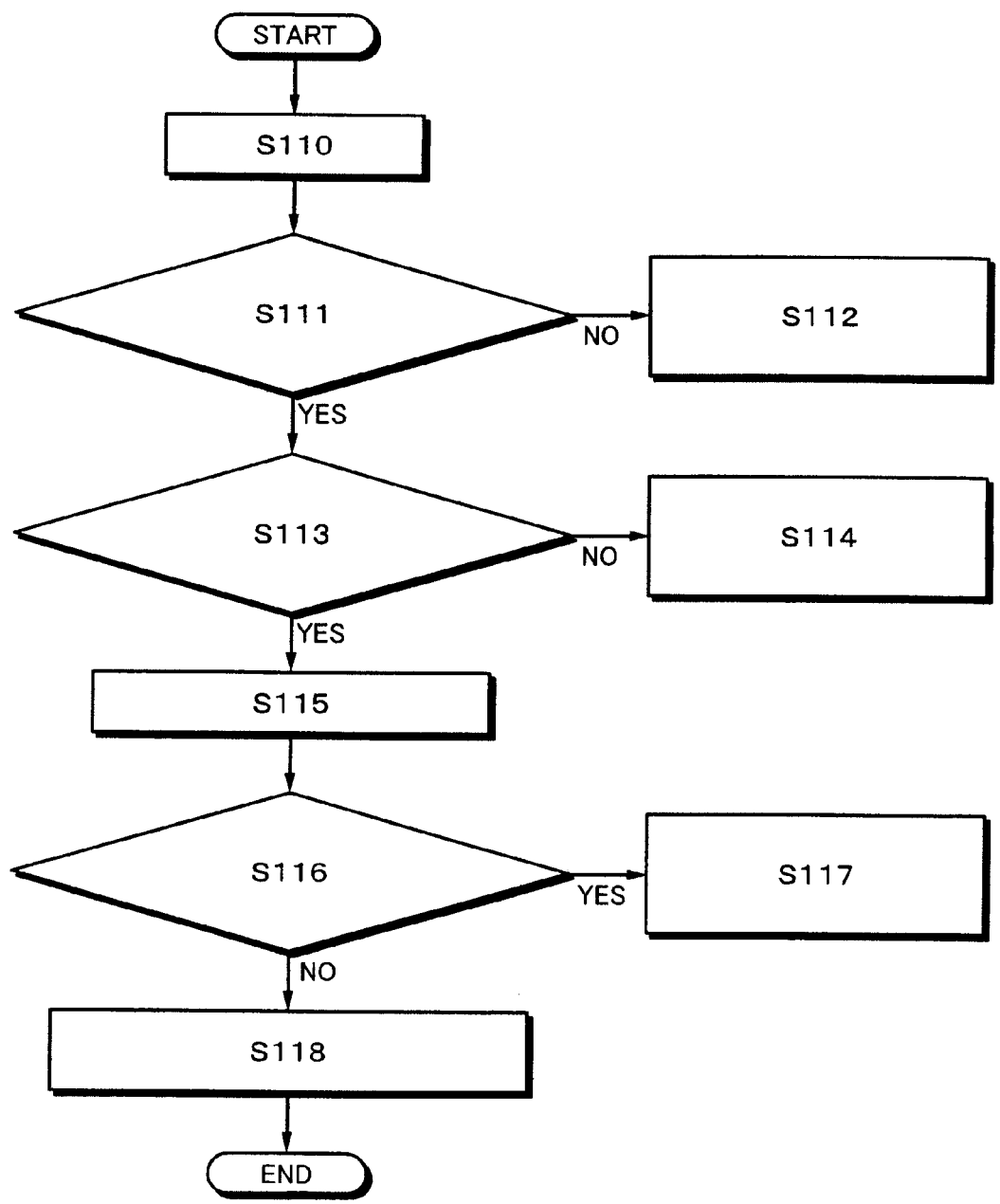
FIG. 45 is a flow chart describing in detail an example of a process of automatically selecting a subtitle stream.

Next, with reference to a flow chart shown in FIG. 45, an example of the process of automatically selecting a subtitle stream at step S83 shown in FIG. 42 will be described in detail. When a subtitle stream is selected (at step S110), the flow advances to step S111. At step S111, it is determined whether the value of argument subtitle_strm, which represents the stream number of a subtitle stream to be reproduced, has been set to "−1" in method play( ) or the value has been omitted. As described above, when the value of argument subtitle_strm is "−1", automatic selection of a subtitle stream is designated.

When the determined result denotes that the value of argument subtitle_strm has been set to other than "−1", the flow advances to step S112. At step S112, the value of argument subtitle_strm is set to property subtitleNumber and a subtitle stream identified by argument subtitle_strm is selected. Thereafter, the flow advances to step S84 shown in FIG. 84. Property subtitleFlag is set in the movie player 300. When a subtitle stream has not been selected at step S112, the process is terminated as an error.

When the process has been terminated as an error, the operation that the UMD video player performs depends on its implementation. When the process has been terminated as an error, the process according to the flow chart shown in FIG. 45 is terminated and the next process is performed although a subtitle stream has not been selected. This error process applies to other error process in FIG. 45.

When the determined result at step S111 denotes that the value of argument subtitle_strm is "−1" or the value has been omitted, the flow advances to step S113. At step S113, it is determined whether there is no subtitle stream identified by property subtitleNumber of the movie player 300 or the value of property subtitleNumber is undefined. When there is a subtitle stream identified by property subtitleNumber, the flow advances to step S114. At step S114, a subtitle stream identified by property subtitleNumber is selected. Thereafter, the flow advances to step S84 shown in FIG. 42. When a subtitle stream has not been selected at step S114, the process is terminated as an error.

When the determined result at step S113 denotes that there is no subtitle stream identified by property subtitleNumber of the movie player 300 or the value of property subtitleNumber is undefined, the flow advances to step S115. Steps after S115 are a real automatic selection process of a subtitle stream.

At step S116, a subtitle stream of block StreamInfo( ) of the clip information file is checked and a language code of the subtitle stream is obtained. It is determined whether or not there is a subtitle stream whose language code is the same as that of property subtitleLanguegeCode of the movie player 300. When the determined result denotes that there is such a subtitle stream, the flow advances to step S117. At step S117, a subtitle stream is selected. When there are a plurality of subtitle streams that satisfy the condition at step S116, a subtitle stream that comes earlier in block StreamInfo( ) in the clip information file is selected. Thereafter, the flow advances to step S84 shown in FIG. 42.

When the determined result at step S116 denotes that there is no subtitle stream that satisfies the condition, the flow advances to step S118. At step S118, since there is no subtitle stream that can be selected, the value of property subtitleFlag is set to "0", which denotes that no subtitle is displayed.

Next, with reference to a flow chart shown in FIG. 46, an example of the process of the automatic setting of property subtitleFlag at step S84 shown in FIG. 42 will be described in detail. When the automatic setting of property subtitleFlag is started (at step S120), the flow advances to step S121. At step S121, it is determined whether or not the value of argument subtitle_status, which represents the status of reproduction of a subtitle of method play( ), has been set to "−1", which represents automatic setting, or the value has been omitted. When the value of argument subtitle_status has been set to other than "−1", the flow advances to step S122. At step S122, the value that has been set to argument subtitle_status is set to property subtitleFlag.

When the value of argument subtitle_status has been set to "−1" or the value has been omitted, the flow advances to step S123. At step S123, it is determined whether or not a language code identified by property subtitleLanguageCode of the movie player 300 matches a language code (property audioLanguageCode of the movie player 300) of an audio stream that is currently being selected and the value of property audioFlag has been set to other than "0", causing an audio stream to be reproduced. When the determined result denotes that the conditions at step S123 are satisfied, the flow advances to step S124.

At step S124, the value of property subtitleFlag is set to "0", causing a subtitle not to be displayed. In other words, when the conditions at step S123 are satisfied, it denotes that the language of audio reproduced by an audio stream is the same as the language of a subtitle displayed by a subtitle stream. Thus, the value of property subtitleFlag is set to "0", causing a subtitle not to be displayed.

When the determined result denotes that the conditions at step S123 are not satisfied, the flow advances to step S125. At step S125, the value of property subtitleFlag is set to "1", causing a subtitle to be displayed.

Figure 46:
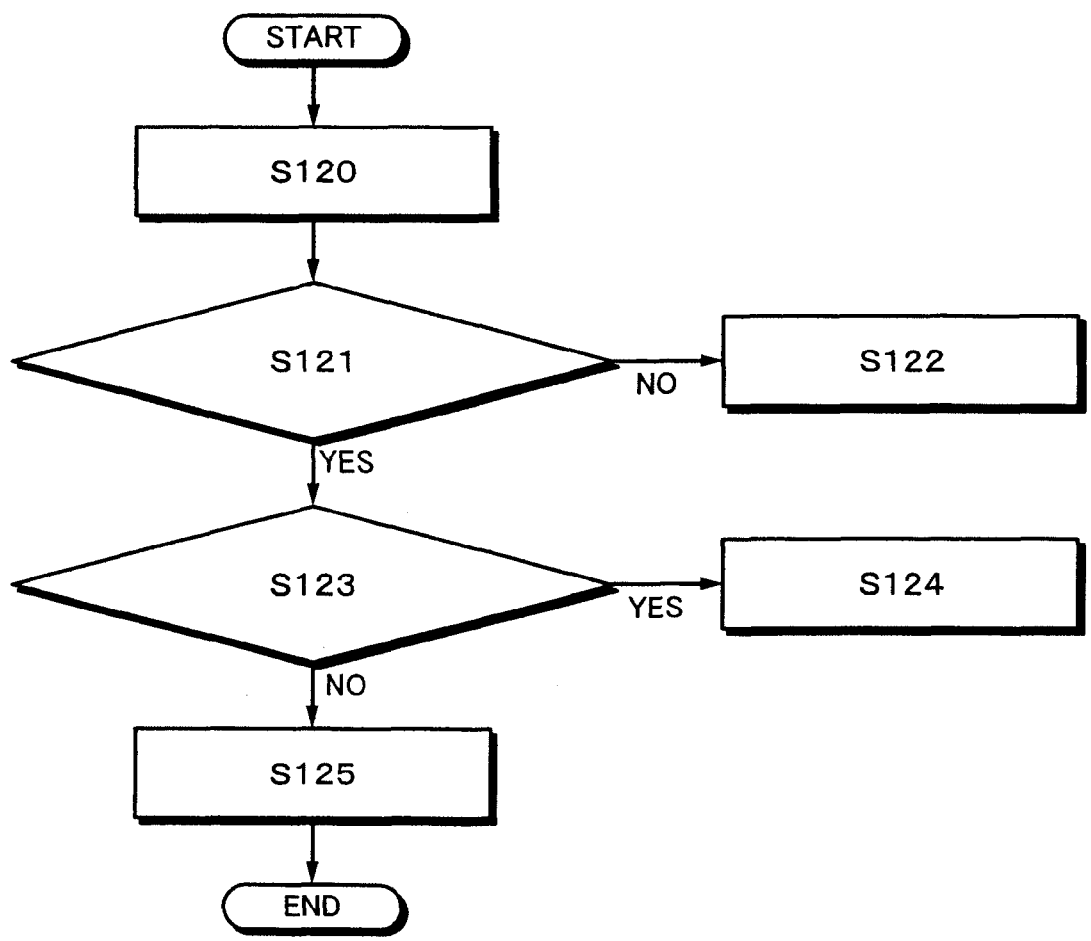
FIG. 46 is a flow chart describing in detail an example of a process of automatically setting property subtitleFlag.

In FIG. 46, at steps S123, S124, and S125, the display of a subtitle is turned on or off corresponding to the language code of a subtitle stream. Instead, with an attribute of a subtitle stream, the display of a subtitle may be turned on or off. For example, even if the language of a subtitle matches the language of audio, when an attribute of a subtitle stream represents a special subtitle such as the foregoing commentary subtitle, the display of the subtitle may not be suppressed (by setting the value of property subtitleFlag to "1"). When a subtitle stream is used for commentary, it is not necessary to suppress the display of the subtitle.

Figure 47:
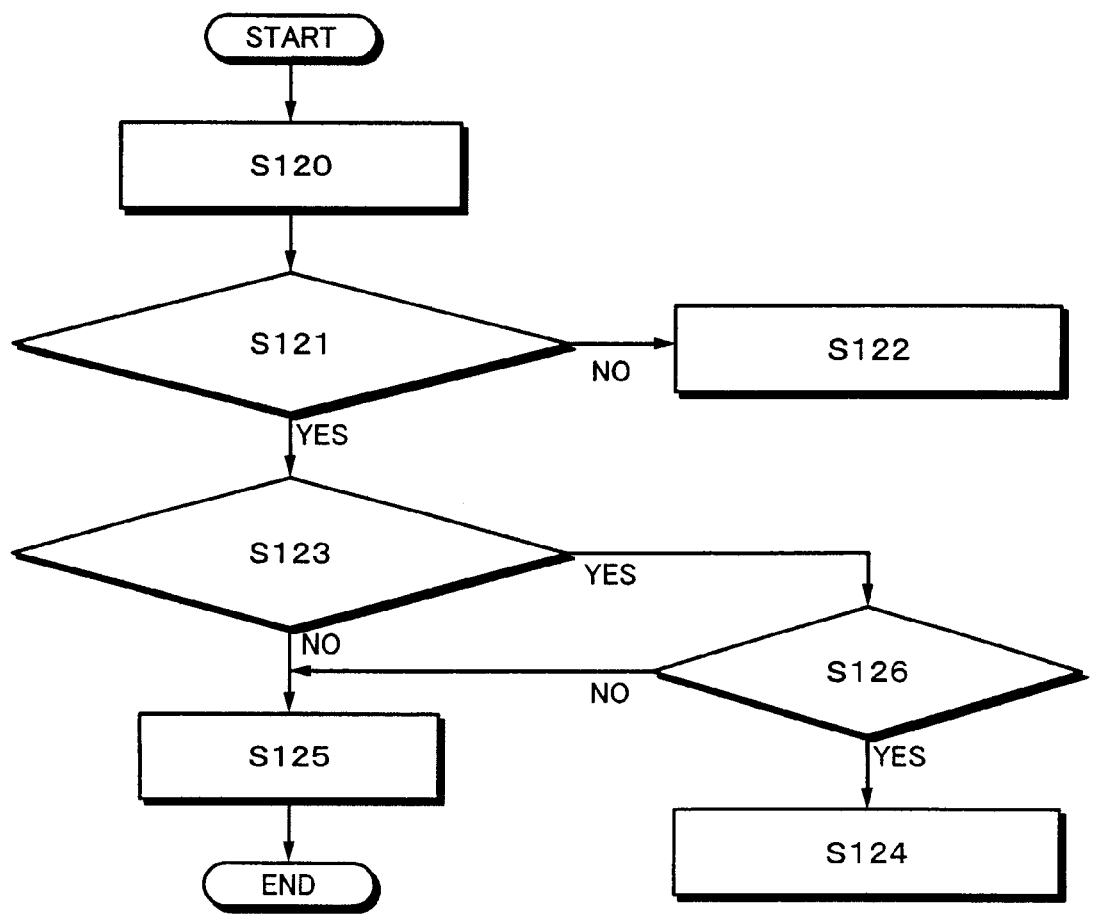
FIG. 47 is a flow chart describing another example of the process of automatically setting property subtitleFlag.

An attribute of a subtitle stream is represented by the value of field subtitle_presentation_type of block StaticInfo( ) of clip AV stream file "XXXXX.CLP" as was described with reference to FIG. 31. Next, an example of a process of setting on/off of display of a subtitle with an attribute of a subtitle stream will be described. In FIG. 47, portions similar to those in FIG. 46 are denoted by similar reference numerals and their description will be omitted. When the determined result at step S123 denotes that the language code identified by property subtitleLanguageCode of the movie player 300 matches the language code of an audio stream that is currently being selected and the value of property audioFlag has been set to other than "0", the flow advances to step S126.

At step S126, it is determined whether or not the attribute of the subtitle stream represents an attribute of a normal subtitle (Normal). When the determined result denotes that the attribute of the subtitle stream represents the attribute of a normal subtitle, the flow advances to step S124. At step S124, the value of property subtitleFlag is set to "0", causing the subtitle not to be displayed. When the determined result denotes that the attribute of the subtitle stream does not represent the attribute of a normal subtitle, the flow advances to step S125. At step S125, the value of property subtitleFlag is set to "1", causing the subtitle to be displayed.

As was described above, audio and a subtitle are properly and automatically selected according to an embodiment of the present invention.

In the foregoing example, audio streams of a plurality of different languages are multiplexed. However, the present invention is not limited to such an example. For instance, audio streams whose language is the same and whose contents are different may be able to be multiplexed. As an example, audio stream A and audio stream B whose languages are the same and whose contents are different may be multiplexed and one stream (for example audio stream A) may be used as an original language.

DESCRIPTION OF REFERENCE NUMERALS

101 DISC
112 CPU
113 MEMORY
115 INPUT INTERFACE
116 VIDEO DECODER
117 AUDIO DECODER
118 VIDEO OUTPUT INTERFACE
119 AUDIO OUTPUT INTERFACE
201 OPERATION SYSTEM
210 VIDEO CONTENT REPRODUCING SECTION
211 SCRIPT CONTROL MODULE
212 PLAYER CONTROL MODULE
214 DECODE CONTROL MODULE
215 BUFFER CONTROL MODULE
216 VIDEO DECODER CONTROL MODULE
217 AUDIO DECODER CONTROL MODULE
218 SUBTITLE DECODER CONTROL MODULE
219 GRAPHICS CONTROL MODULE
241 VIDEO OUTPUT MODULE
242 VIDEO OUTPUT MODULE
250 NONVOLATILE MEMORY CONTROL MODULE
300 MOVIE PLAYER
301 NATIVE IMPLEMENTATION PLATFORM
302 SCRIPT LAYER
310 USER INPUT
311 CONTROL COMMAND
312 EVENT
313 METHOD
320 DATABASE
321 PLAYBACK MODULE
322 DECODER ENGINE
323 PROPERTY
324 RESUME INFORMATION
S10 DURING REPRODUCTION, USER PRESSES "next" KEY.
S11 uo_playNextChapter( ) OCCURS.
S12 OBTAIN POSITION OF NEXT CHAPTER MARK FROM DATABASE OF PLAYLIST.
S13 DOES NEXT CHAPTER MARK EXIST?
S14 STOP CURRENT REPRODUCTION.
S15 JUMP TO POSITION REPRESENTED BY NEXT CHAPTER MARK AND STARTS REPRODUCING VIDEO.
S16 MARK EVENT OCCURS.
S17 START EXECUTING EVENT HANDLER CORRESPONDING TO MARK EVENT.
S18 OBTAIN CHAPTER NUMBER WITH INFORMATION INFORMED UPON OCCURRENCE OF EVENT.
S19 DISPLAY MESSAGE REPRESENTING BEGINNING OF CHAPTER.
S20 COMPLETE EXECUTION OF EVENT HANDLER.
S30 LOAD DISC.
S31 LOAD CONTINUOUS REPRODUCTION INFORMATION.
S32 DOES CONTINUOUS REPRODUCTION INFORMATION EXIST?
S33 on ContinuePlay
S34 on AutoPlay
S35 ACCEPT EVENT AND EXECUTE EVENT HANDLER.
S36 EXECUTE on Exit.
S37 STOP MOVIE PLAYER (STORE CONTINUOUS REPRODUCTION INFORMATION).
S38 COMPLETE REPRODUCTION.
S39 WILL YOU SEE CONTENT ONCE AGAIN?
S40 EJECT DISC.
S50 USER CAUSES MOVIE PLAYER TO PERFORM REPRODUCTION (FROM BEGINNING).
S51 DOES EVENT HANDLER on AutoPlay( ) EXIST?
S52 NATIVE IMPLEMENTATION PLATFORM INFORMS SCRIPT OF EVENT autoPlay.
S53 NATIVE IMPLEMENTATION PLATFORM INFORMS SCRIPT OF EVENT Exit.
S54 EXECUTE EVENT HANDLER on AutoPlay.
S60 USER CAUSES MOVIE PLAYER TO PERFORM REPRODUCTION (CONTINUOUS REPRODUCTION).
S61 DOES RESUME INFORMATION EXIST?
S62 PERFORM REPRODUCTION FROM BEGINNING.
S63 DOES SCRIPT CONTAIN EVENT HANDLER on ContinuePlay?
S64 EXECUTE EVENT HANDLER on ContinuePlay.
S65 EXECUTES DEFAULT EVENT HANDLER on ContinuePlay.
S70 USER CAUSES MOVIE PLAYER TO STOP REPRODUCTION.
S71 WHEN RECEIVING USER'S OPERATION, NATIVE IMPLEMENTATION PLATFORM STARTS EXIT PROCESS:

(1) RESTRAINS NEW EVENTS FROM OCCURRING,
(2) DISCARDS EVENT HANDLERS THAT HAVE BEEN QUEUED, AND
(3) ISSUES COMMAND uo_stop( ) TO MOVIE PLAYER.

S72 STOP EXECUTION OF CURRENT EVENT HANDLER.

S73 NATIVE IMPLEMENTATION PLATFORM INFORMS SCRIPT LAYER OF EVENT Exit.

S74 EXECUTE EVENT HANDLER on Exit (POST-PROCESS, EXECUTION OF METHOD setUserData, ETC.)

S75 NATIVE IMPLEMENTATION PLATFORM PERFORMS EXIT PROCESS (STORING CONTINUOUS INFORMATION TO NONVOLATILE MEMORY, CHANGING TO SYSTEM MENU, ETC).

S80 SELECT VIDEO STREAM.

S81 AUTOMATICALLY SELECT AUDIO STREAM.

S82 SET audioFlag.

S83 AUTOMATICALLY SELECT SUBTITLE STREAM.

S84 AUTOMATICALLY SET subtitleFlag.

S90 SELECT AUDIO STREAM.

S91 HAS VALUE OF ARGUMENT audio_strm IN METHOD BEEN SET TO "−1" (AUTOMATIC SELECTION) OR HAS ARGUMENT audio_strm BEEN OMITTED?

S92 SET ARGUMENT audio strm TO PROPERTY audioNumber AND SELECT AUDIO STREAM IDENTIFIED BY ARGUMENT audio_strm. WHEN AUDIO STREAM IS NOT ABLE TO BE SELECTED, PROCESS IS TERMINATED AS ERROR.

S93 IS THERE STREAM IDENTIFIED BY PROPERTY audioNumber OF MOVIE PLAYER OR IS audioNumber UNDEFINED?

S94 SELECT AUDIO STREAM IDENTIFIED BY audioNumber. WHEN AUDIO STREAM IS NOT ABLE TO BE SELECTED, PROCESS IS TERMINATED AS ERROR.

S95 START AUTOMATIC SELECTION FOR AUDIO STREAM.

S96 HAS PROPERTY audioLanguageCode OF MOVIE PLAYER BEEN SET TO "ORIGINAL LANGUAGE"?

S97 IS THERE STREAM WHOSE LANGUAGE CODE IS SAME AS THAT OF PROPERTY audioLanguageCode OF MOVIE PLAYER AND WHOSE NUMBER OF AUDIO CHANNELS IS EQUAL TO OR SMALLER THAN NUMBER OF AUDIO CHANNELS THAT HAS BEEN SET TO MOVIE PLAYER?

S98 SELECT STREAM WHOSE NUMBER OF AUDIO CHANNELS IS MAXIMUM IN THOSE THAT SATISFY PREDETERMINED CONDITIONS. WHEN THERE ARE A PLURALITY OF STREAMS WHOSE NUMBER OF AUDIO CHANNELS IS SAME, SELECT STREAM THAT COMES EARLIER IN StreamInfo( ) OF CLIP INFORMATION FILE.

S99 IS THERE STREAM WHOSE NUMBER OF AUDIO CHANNELS IS EQUAL TO OR SMALLER THAN NUMBER OF AUDIO CHANNELS THAT HAS BEEN SET TO UMD VIDEO PLAYER?

S100 SELECT STREAM WHOSE NUMBER OF AUDIO CHANNELS IS MAXIMUM IN THOSE. WHEN THERE ARE PLURALITY OF STREAMS WHOSE NUMBER OF AUDIO CHANNELS, SELECT STREAM THAT COMES EARLIER IN StreamInfo( ) OF CLIP INFORMATION FILE.

S101 IS THERE STREAM WHOSE LANGUAGE CODE IS SAME AS THAT OF AUDIO STREAM THAT COMES FIRST IN StreamInfo( ) AND WHOSE NUMBER OF AUDIO CHANNELS IS EQUAL TO OR SMALLER THAN NUMBER OF AUDIO CHANNELS THAT HAS BEEN SET TO UMD VIDEO PLAYER?

S102 SELECT STREAM WHOSE NUMBER OF AUDIO CHANNELS IS MAXIMUM IN THOSE THAT SATISFY PREDETERMINED CONDITIONS. WHEN THERE ARE PLURALITY OF STREAMS WHOSE NUMBER OF AUDIO CHANNELS IS SAME, SELECT STREAM THAT COMES EARLIER IN StreamInfo( ) OF CLIP INFORMATION FILE.

S103 IS THERE STREAMS WHOSE NUMBER OF AUDIO CHANNELS IS EQUAL TO OR SMALLER THAN NUMBER OF AUDIO CHANNELS THAT HAS BEEN SET TO UMD VIDEO PLAYER?

S104 SELECT STREAM WHOSE NUMBER OF AUDIO CHANNELS IS MAXIMUM IN THOSE. WHEN THERE ARE A PLURALITY OF STREAMS WHOSE NUMBER OF AUDIO CHANNELS IS SAME, SELECT STREAM THAT COMES EARLIER IN StreamInfo( ) OF CLIP INFORMATION FILE.

S110 SELECT SUBTITLE STREAM.

S111 HAS ARGUMENT subtitle_strm OF METHOD BEEN SET TO "1" (AUTOMATIC SELECTION) OR HAS ARGUMENT subtitle_strm BEEN OMITTED?

S112 SET ARGUMENT subtitle_strm TO PROPERTY subtitleNumber AND SELECT SUBTITLE STREAM IDENTIFIED BY ARGUMENT subtitle_strm. WHEN SUBTITLE STREAM IS NOT ABLE TO BE SELECTED, PROCESS IS TERMINATED AS ERROR.

S113 IS THERE NO STREAM IDENTIFIED BY PROPERTY subtitleNumber OF MOVIE PLAYER OR IS subtitleNumber UNDEFINED?

S114 SELECT SUBTITLE STREAM IDENTIFIED BY subtitleNumber. WHEN SUBTITLE STREAM IS NOT ABLE TO BE SELECTED, PROCESS IS TERMINATED AS ERROR.

S115 START AUTOMATIC SELECTION FOR SUBTITLE STREAM.

S116 IS THERE STREAM WHOSE LANGUAGE CODE IS SAME AS THAT OF PROPERTY SubtitleLanguageCode OF MOVIE PLAYER?

S117 SELECT STREAM. WHEN THERE ARE A PLURALITY OF SUBTITLE STREAMS THAT SATISFY PREDETERMINED CONDITION, SELECT STREAM THAT COMES EARLIER IN StreamInfo( ) IN CLIP INFORMATION FILE.

S118 SINCE THERE IS NO SUBTITLE STREAM THAT CAN BE SELECTED, SET subtitleFlag TO 0.

S120 AUTOMATICALLY SET subtitleFlag.

S121 HAS ARGUMENT subtitle_status OF METHOD BEEN SET TO "−1" (AUTOMATIC SETTING) OR HAS BEEN OMITTED?

S122 SET VALUE OF subtitle_status TO PROPERTY subtitleFlag.

S123 DOES LANGUAGE CODE OF subtitleLanguageCode MATCH LANGUAGE CODE (audioLanguageCode) OF AUDIO CURRENTLY BEING SELECTED AND VALUE OF audioFlag HAS BEEN SET TO OTHER THAN 0?

S124 SET subtitleFlag TO 0, CAUSING DISPLAY OF AUDIO TO BE TURNED OFF.

S125 SET subtitleFlag TO 1 (CAUSING DISPLAY OF SUBTITLE TO BE TURNED ON).

The invention claimed is:
1. A reproducing apparatus of reproducing content data from a disc-shaped recording medium, comprising:
read means for reading data from the recording medium on which content data containing at least a video stream, one or a plurality of audio streams corresponding to the video stream and a reproduction control program with which reproduction of the content data is controlled have been recorded;

player means for reproducing the content data according to the reproduction control program;

first mode setting means for setting a first mode to the player means such that it automatically selects an audio stream of an original language from the one or plurality of audio streams when the content data are reproduced;

wherein the content data also includes one or a plurality of subtitle streams, and wherein the reproducing apparatus further comprises:

second mode setting means for setting a second mode to the player means such that it selects whether or not to reproduce the one or a plurality of subtitle streams when the content data are reproduced;

further comprising:

audio stream automatic selection setting means for setting whether or not to automatically select one audio stream from the one or plurality of audio streams; and subtitle stream automatic selection setting means for setting whether or not to automatically select one subtitle stream from the one or plurality of subtitle streams, wherein a language of the audio stream automatically selected according to a setting of the audio stream automatic selection setting means matches a language of the subtitle stream automatically selected according to a setting of the subtitle stream automatic selection setting means, the second mode of the second mode setting means is automatically set such that the selected one or a plurality of subtitle streams is not reproduced.

2. The reproducing apparatus as set forth in claim 1, wherein in the automatic selection of the audio stream automatic selection setting means, when the first mode has been set by the first mode setting means, an audio stream of an original language is selected from the one or plurality of audio streams, and when the first mode has not been set by the first mode setting means, an audio stream of a language set by the player means is selected from the one or plurality of audio streams.

3. The reproducing apparatus as set forth in claim 1, wherein in the automatic selection of the subtitle stream automatic selection setting means, a subtitle stream of a language set by the player means is selected from the one or plurality of subtitle streams.

4. The reproducing apparatus as set forth in claim 1, wherein stream information has been also recorded on the recording medium, the stream information describing at least information which identifies each of the one or plurality of subtitle streams, and wherein when there are a plurality of subtitle streams whose language is the same, the player means selects the subtitle stream which comes earlier in the stream information from the one or plurality of subtitle streams.

5. The reproducing apparatus as set forth in claim 1, wherein stream information has been also recorded on the recording medium, the stream information describing at least information which identifies each of the one or plurality of audio streams, and wherein the player means determines that the audio stream at a position which comes first in the stream information of the one or plurality of audio streams be an audio stream of the original language.

6. The reproducing apparatus as set forth in claim 5, wherein the stream information also describes information representing a number of channels of an audio stream, wherein the player means automatically selects an audio stream whose language is the same as the original language and whose number of channels is maximum from the one or plurality of audio streams.

7. The reproducing apparatus as set forth in claim 6, wherein there are a plurality of audio streams whose language is the same as the original language and whose number of channels is the same, the player means selects an audio stream which comes first in the stream information from the one or plurality of audio streams.

8. A reproducing method of reproducing content data from a disc-shaped recording medium, comprising the steps of:

reading data from the recording medium on which content data containing at least a video stream, one or a plurality of audio streams corresponding to the video stream, and a reproduction control program with which reproduction of the content data is controlled have been recorded;

reproducing the content data according to the reproduction control program;

setting a first mode to the content reproduction step such that an audio stream of an original language is automatically selected from the one or plurality of audio streams when the content data are reproduced;

wherein the reproduction control program causes a reproducing apparatus which reproduces the content data to automatically select the original language based on the stream information;

wherein the content data also contain one or a plurality of subtitle streams corresponding to the video stream, and wherein the reproduction control program causes the reproducing apparatus to automatically select one audio stream from the one or plurality of audio streams, to automatically select one subtitle stream from the one or plurality of subtitle streams, and not to reproduce the selected subtitle stream when a language of the audio stream which has been automatically selected matches a language of the subtitle stream which has been automatically selected.

9. A reproducing method executed by a computer device, the reproducing method reproducing content data from a disc-shaped recording medium, the reproducing method comprising the steps of:

reading data from the recording medium on which content data containing at least a video stream, one or a plurality of audio streams corresponding to the video stream, and a reproduction control program with which reproduction of the content data is controlled have been recorded;

reproducing the content data according to the reproduction control program;

setting a first mode to the content reproduction step such that an audio stream of an original language is automatically selected from the one or plurality of audio streams when the content data are reproduced;

wherein the reproduction control program causes a reproducing apparatus which reproduces the content data to automatically select the original language based on the stream information;

wherein the content data also contain one or a plurality of subtitle streams corresponding to the video stream, and wherein the reproduction control program causes the reproducing apparatus to automatically select one audio stream from the one or plurality of audio streams, to automatically select one subtitle stream from the one or plurality of subtitle streams, and not to reproduce the selected subtitle stream when a language of the audio stream which has been automatically selected matches a language of the subtitle stream which has been automatically selected.

10. A non-transitory recording medium on which content data containing at least a video stream, one or a plurality of video streams corresponding to the video stream, a reproduction control program with which reproduction of the content data is controlled, and stream information describing at least information which identifies each of one or a plurality of audio streams such that the information which identifies the audio stream used as an original language comes first have been recorded;

wherein the reproduction control program causes a reproducing apparatus which reproduces the content data to automatically select the original language based on the stream information;

wherein the content data also contain one or a plurality of subtitle streams corresponding to the video stream, and wherein the reproduction control program causes the reproducing apparatus to automatically select one audio stream from the one or plurality of audio streams, to automatically select one subtitle stream from the one or plurality of subtitle streams, and not to reproduce the selected subtitle stream when a language of the audio stream which has been automatically selected matches a language of the subtitle stream which has been automatically selected.

11. The recording medium as set forth in claim 10,
wherein the stream information also contains at last information which identifies each of the one or plurality of subtitle streams, and
wherein when there are a plurality of subtitle streams whose language is the same in the one or plurality of subtitle streams, the subtitle stream to be selected comes earlier in the stream information.

12. The recording medium as set forth in claim 10,
wherein the stream information also describes information representing a number of channels of the audio streams, and
wherein the reproducing apparatus which reproduces the content data is caused to automatically select an audio stream whose number of channels is maximum and whose language is the same as the original language from the one or plurality of audio streams.

13. The recording medium as set forth in claim 12,
wherein when there are a plurality of audio streams whose language is the same as the original language and whose number of channels is the same in the one or plurality of audio streams, the audio stream to be selected comes earlier in the stream information.

14. A non-transitory recording medium storing a data structure comprising:
a video stream;
content data containing one or a plurality of audio streams corresponding to the video stream;
a reproduction control program with which reproduction of the content data is controlled;
stream information containing at least information which identifies each of the one or plurality of audio streams such that the information which identifies the audio stream used as an original language comes first;
wherein the reproduction control program causes a reproducing apparatus which reproduces the content data to automatically select the original language based on the stream information;
wherein the content data also contain one or a plurality of subtitle streams corresponding to the video stream, and
wherein the reproduction control program causes the reproducing apparatus to automatically select one audio stream from the one or plurality of audio streams, to automatically select one subtitle stream from the one or plurality of subtitle streams, and not to reproduce the selected subtitle stream when a language of the audio stream which has been automatically selected matches a language of the subtitle stream which has been automatically selected.

* * * * *